US012673988B2

(12) United States Patent
Shaheen et al.

(10) Patent No.: US 12,673,988 B2
(45) Date of Patent: *Jul. 7, 2026

(54) ALBUMIN BINDING PROTEINS AND METHODS OF USE

(71) Applicant: Paragon Therapeutics, Inc., Waltham, MA (US)

(72) Inventors: Hussam Hisham Shaheen, Vega Alta, PR (US); Yuqi Liu, Belmont, MA (US)

(73) Assignee: Paragon Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/353,476

(22) Filed: Oct. 8, 2025

(65) Prior Publication Data

US 2026/0035444 A1 Feb. 5, 2026

Related U.S. Application Data

(63) Continuation of application No. 19/180,749, filed on Apr. 16, 2025, now Pat. No. 12,459,994, which is a continuation of application No. PCT/US2025/024245, filed on Apr. 11, 2025.

(60) Provisional application No. 63/633,667, filed on Apr. 12, 2024, provisional application No. 63/633,665, filed on Apr. 12, 2024.

(51) Int. Cl.
*C07K 16/18* (2006.01)

(52) U.S. Cl.
CPC .......... *C07K 16/18* (2013.01); *C07K 2317/22* (2013.01); *C07K 2317/24* (2013.01); *C07K 2317/52* (2013.01); *C07K 2317/569* (2013.01); *C07K 2317/92* (2013.01); *C07K 2319/21* (2013.01)

(58) Field of Classification Search
None
See application file for complete search history.

(56) References Cited

U.S. PATENT DOCUMENTS 8,703,135 B2 * 4/2014 Beste ..................... G01N 33/53
530/387.9
9,573,992 B2 2/2017 Dombrecht et al.

9,920,115 B2 3/2018 Dubridge et al.
11,312,764 B2 4/2022 Buyse et al.
11,332,519 B2 5/2022 Buyse
12,344,678 B2 * 7/2025 Bobkov ............. C07K 16/4258
12,459,994 B2 * 11/2025 Shaheen ................ C07K 16/18
2011/0300158 A1 * 12/2011 De Angelis ...... C07K 14/57563
530/389.3
2014/0228546 A1 8/2014 Dombrecht et al.
2020/0407448 A1 12/2020 Kley et al.
2022/0089754 A1 3/2022 Macoin et al.

FOREIGN PATENT DOCUMENTS

WO WO-2004/041865 A2 5/2004
WO WO-2006/122787 A1 11/2006
WO WO-2008/096158 A2 8/2008
WO WO-2011/006915 A2 1/2011
WO WO-2012175400 A1 * 12/2012 ............. C07K 16/18
WO WO-2014/111550 A1 7/2014
WO WO-2015/173325 A2 11/2015
WO WO-2018/134235 A1 7/2018
WO WO-2023/186120 A1 10/2023
WO WO-2023/242362 A1 12/2023
WO WO-2024/051796 A1 3/2024
WO WO-2024/084203 A1 4/2024
WO 2025/217488 A1 10/2025
WO 2025/217497 A1 10/2025
WO 2025/217579 A1 10/2025

OTHER PUBLICATIONS

Chen et al. "Discovery of Novel Anti-Serum Albumin VHH as a Building Block for PK Prolongation" Antibody Therapeutics, vol. 6, Supplement 1, Jul. 24, 2023, 2 pages.
Crauwels et al. "Reshaping nanobodies for affinity purification on protein a", New Biotechnology, vol. 57, Jan. 2020, pp. 20-28.
Dennis et al. "Albumin Binding as a General Strategy for Improving the Pharmacokinetics of Proteins" The Journal of Biological Chemistry, vol. 277, No. 38, Issue of Sep. 20, 2002, pp. 35035-35043.
International Search Report and Written Opinion for PCT Application No. PCT/US2025/024245 dated Jul. 15, 2025.
International Search Report and Written Opinion for PCT Application No. PCT/US2025/024227 dated Jul. 14, 2025.
Kipriyanov et al., Generation and Production of Engineered Antibodies, Mol. Bio., 26:39-60 (2004).

* cited by examiner

*Primary Examiner* — Julie Wu
*Assistant Examiner* — Julia A Rossi
(74) *Attorney, Agent, or Firm* — GOODWIN PROCTER LLP

(57) ABSTRACT

Provided herein are albumin binding proteins and methods of making and using thereof.

9 Claims, No Drawings

Specification includes a Sequence Listing.

```
                         SEQUENCE LISTING

Sequence total quantity: 242
SEQ ID NO: 1              moltype = AA  length = 117
FEATURE                   Location/Qualifiers
source                    1..117
                          mol_type = protein
                          organism = synthetic construct
SEQUENCE: 1
QVQLVESGGG LVQPGGSLRL SCAASGFTFG QFGMSWVRQA PAKGPERVSA ISSDGSGTIY  60
ADSVKGRFTI SRDNAKNTLY LQMNSLKPED TAVYYCTIGS STTPSGPGQG TQVTVSS    117

SEQ ID NO: 2              moltype = AA  length = 5
FEATURE                   Location/Qualifiers
source                    1..5
                          mol_type = protein
                          organism = synthetic construct
SEQUENCE: 2
QFGMS                                                              5

SEQ ID NO: 3              moltype = AA  length = 17
FEATURE                   Location/Qualifiers
source                    1..17
                          mol_type = protein
                          organism = synthetic construct
SEQUENCE: 3
AISSDGSGTI YADSVKG                                                 17

SEQ ID NO: 4              moltype = AA  length = 8
FEATURE                   Location/Qualifiers
source                    1..8
                          mol_type = protein
                          organism = synthetic construct
SEQUENCE: 4
GSSTTPSG                                                           8

SEQ ID NO: 5              moltype = AA  length = 348
FEATURE                   Location/Qualifiers
source                    1..348
                          mol_type = protein
                          organism = synthetic construct
SEQUENCE: 5
QVQLVESGGG LVQPGGSLRL SCAASGFTFG QFGMSWVRQA PAKGPERVSA ISSDGSGTIY  60
ADSVKGRFTI SRDNAKNTLY LQMNSLKPED TAVYYCTIGS STTPSGPGQG TQVTVSSGGG  120
```

-continued

```
GSDKTHTCPP CPAPELLGGP SVFLFPPKPK DTLMISRTPE VTCVVVDVSH EDPEVKFNWY    180
VDGVEVHNAK TKPREEQYNS TYRVVSVLTV LHQDWLNGKE YKCKVSNKAL PAPIEKTISK    240
AKGQPREPQV YTLPPSRDEL TKNQVSLTCL VKGFYPSDIA VEWESNGQPE NNYKTTPPVL    300
DSDGSFFLYS KLTVDKSRWQ QGNVFSCSVM HEALHNHYTQ KSLSLSPG                 348

SEQ ID NO: 6              moltype = AA  length = 127
FEATURE                   Location/Qualifiers
source                    1..127
                          mol_type = protein
                          organism = synthetic construct
SEQUENCE: 6
QVQLVESGGG LVQPGGSLRL SCAASGFTFG QFGMSWVRQA PAKGPERVSA ISSDGSGTIY    60
ADSVKGRFTI SRDNAKNTLY LQMNSLKPED TAVYYCTIGS STTPSGPGQG TQVTVSSGGH    120
HHHHHHH                                                              127

SEQ ID NO: 7              moltype = AA  length = 117
FEATURE                   Location/Qualifiers
source                    1..117
                          mol_type = protein
                          organism = synthetic construct
SEQUENCE: 7
EVQLLESGGG LVQPGGSLRL SCAASGFTFG QFGMSWVRQA PGKGPERVSA ISSDGSGTIY    60
ADSVKGRFTI SRDNSKNTLY LQMNSLRPED TAVYYCTIGS STTPSGPGQG TLVTVSS       117

SEQ ID NO: 8              moltype = AA  length = 117
FEATURE                   Location/Qualifiers
source                    1..117
                          mol_type = protein
                          organism = synthetic construct
SEQUENCE: 8
EVQLLESGGG LVQPGGSLRL SCAASGFTFS QFGMSWVRQA PGKGPERVSA ISSDGSGTIY    60
ADSVKGRFTI SRDNSKNTLY LQMNSLRPED TAVYYCTIGS STTPSGPGQG TLVTVSS       117

SEQ ID NO: 9              moltype = AA  length = 117
FEATURE                   Location/Qualifiers
source                    1..117
                          mol_type = protein
                          organism = synthetic construct
SEQUENCE: 9
QVQLVESGGG LVQPGGSLRL SCAASGFTFG QFGMSWVRQA PAKGPERVSA ISSSGSGTIY    60
ADSVKGRFTI SRDNAKNTLY LQMNSLKPED TAVYYCTIGS STTPSGPGQG TQVTVSS       117

SEQ ID NO: 10             moltype = AA  length = 117
FEATURE                   Location/Qualifiers
source                    1..117
                          mol_type = protein
                          organism = synthetic construct
SEQUENCE: 10
QVQLVESGGG LVQPGGSLRL SCAASGFTFG QFGMSWVRQA PAKGPERVSA ISSGGSGTIY    60
ADSVKGRFTI SRDNAKNTLY LQMNSLKPED TAVYYCTIGS STTPSGPGQG TQVTVSS       117

SEQ ID NO: 11             moltype = AA  length = 117
FEATURE                   Location/Qualifiers
source                    1..117
                          mol_type = protein
                          organism = synthetic construct
SEQUENCE: 11
QVQLVESGGG LVQPGGSLRL SCAASGFTFG QFGMSWVRQA PAKGPERVSA ISSDASGTIY    60
ADSVKGRFTI SRDNAKNTLY LQMNSLKPED TAVYYCTIGS STTPSGPGQG TQVTVSS       117

SEQ ID NO: 12             moltype = AA  length = 117
FEATURE                   Location/Qualifiers
source                    1..117
                          mol_type = protein
                          organism = synthetic construct
SEQUENCE: 12
QVQLVESGGG LVQPGGSLRL SCAASGFTFG QFGMSWVRQA PAKGPERVSA ISSDSSGTIY    60
ADSVKGRFTI SRDNAKNTLY LQMNSLKPED TAVYYCTIGS STTPSGPGQG TQVTVSS       117

SEQ ID NO: 13             moltype = AA  length = 117
FEATURE                   Location/Qualifiers
source                    1..117
                          mol_type = protein
                          organism = synthetic construct
SEQUENCE: 13
EVQLVESGGG LVQPGGSLRL SCAASGFTFG QFGMSWVRQA PGKGLEWVSA ISSDGSGTIY    60
ADSVKGRFTI SRDNSKNTLY LQMNSLRAED TAVYYCTIGS STTPSGWGQG TTVTVSS       117

SEQ ID NO: 14             moltype = AA  length = 117
```

-continued

```
FEATURE                 Location/Qualifiers
source                  1..117
                        mol_type = protein
                        organism = synthetic construct
SEQUENCE: 14
EVQLVESGGG LVQPGGSLRL SCAASGFTFG QFGMSWVRQA PGKGLEWVSA ISSDGSGTIY   60
ADSVKGRFTI SRDNSKNTLY LQMNSLRAED TAVYYCTIGS STTPSGPGQG TTVTVSS     117

SEQ ID NO: 15          moltype = AA  length = 117
FEATURE                 Location/Qualifiers
source                  1..117
                        mol_type = protein
                        organism = synthetic construct
SEQUENCE: 15
EVQLVESGGG LVQPGGSLRL SCAASGFTFG QFGMSWFRQA PGKEREFVSA ISSDGSGTIY   60
ADSVKGRFTI SRDNSKNTLY LQMNSLRAED TAVYYCTIGS STTPSGWGQG TTVTVSS     117

SEQ ID NO: 16          moltype = AA  length = 117
FEATURE                 Location/Qualifiers
source                  1..117
                        mol_type = protein
                        organism = synthetic construct
SEQUENCE: 16
EVQLVESGGG LVQPGGSLRL SCAASGFTFG QFGMSWFRQA PGKEREFVSA ISSDGSGTIY   60
ADSVKGRFTI SRDNSKNTLY LQMNSLRAED TAVYYCTIGS STTPSGPGQG TTVTVSS     117

SEQ ID NO: 17          moltype = AA  length = 115
FEATURE                 Location/Qualifiers
source                  1..115
                        mol_type = protein
                        organism = synthetic construct
SEQUENCE: 17
EVQLLESGGG LVQPGGSLRL SCAASGFTFR SFGMSWVRQA PGKGPEWVSS ISGSGSDTLY   60
ADSVKGRFTI SRDNSKNTLY LQMNSLRPED TAVYYCTIGG SLSRSSQGTL VTVSS       115

SEQ ID NO: 18          moltype = AA  length = 5
FEATURE                 Location/Qualifiers
source                  1..5
                        mol_type = protein
                        organism = synthetic construct
SEQUENCE: 18
SFGMS                                                               5

SEQ ID NO: 19          moltype = AA  length = 17
FEATURE                 Location/Qualifiers
source                  1..17
                        mol_type = protein
                        organism = synthetic construct
SEQUENCE: 19
AISSDASGTI YADSVKG                                                  17

SEQ ID NO: 20          moltype = AA  length = 17
FEATURE                 Location/Qualifiers
source                  1..17
                        mol_type = protein
                        organism = synthetic construct
SEQUENCE: 20
AISSDSSGTI YADSVKG                                                  17

SEQ ID NO: 21          moltype = AA  length = 17
FEATURE                 Location/Qualifiers
source                  1..17
                        mol_type = protein
                        organism = synthetic construct
SEQUENCE: 21
SISGSGSDTL YADSVKG                                                  17

SEQ ID NO: 22          moltype = AA  length = 6
FEATURE                 Location/Qualifiers
source                  1..6
                        mol_type = protein
                        organism = synthetic construct
SEQUENCE: 22
GGSLSR                                                              6

SEQ ID NO: 23          moltype = AA  length = 348
FEATURE                 Location/Qualifiers
source                  1..348
                        mol_type = protein
```

-continued

```
                        organism = synthetic construct
SEQUENCE: 23
EVQLLESGGG LVQPGGSLRL SCAASGFTFG QFGMSWVRQA PGKGPERVSA ISSDGSGTIY   60
ADSVKGRFTI SRDNSKNTLY LQMNSLRPED TAVYYCTIGS STTPSGPGQG TLVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 24           moltype = AA  length = 348
FEATURE                 Location/Qualifiers
source                  1..348
                        mol_type = protein
                        organism = synthetic construct
SEQUENCE: 24
EVQLLESGGG LVQPGGSLRL SCAASGFTFS QFGMSWVRQA PGKGPERVSA ISSDGSGTIY   60
ADSVKGRFTI SRDNSKNTLY LQMNSLRPED TAVYYCTIGS STTPSGPGQG TLVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 25           moltype = AA  length = 348
FEATURE                 Location/Qualifiers
source                  1..348
                        mol_type = protein
                        organism = synthetic construct
SEQUENCE: 25
QVQLVESGGG LVQPGGSLRL SCAASGFTFG QFGMSWVRQA PAKGPERVSA ISSSGSGTIY   60
ADSVKGRFTI SRDNAKNTLY LQMNSLKPED TAVYYCTIGS STTPSGPGQG TQVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 26           moltype = AA  length = 348
FEATURE                 Location/Qualifiers
source                  1..348
                        mol_type = protein
                        organism = synthetic construct
SEQUENCE: 26
QVQLVESGGG LVQPGGSLRL SCAASGFTFG QFGMSWVRQA PAKGPERVSA ISSGGSGTIY   60
ADSVKGRFTI SRDNAKNTLY LQMNSLKPED TAVYYCTIGS STTPSGPGQG TQVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 27           moltype = AA  length = 348
FEATURE                 Location/Qualifiers
source                  1..348
                        mol_type = protein
                        organism = synthetic construct
SEQUENCE: 27
QVQLVESGGG LVQPGGSLRL SCAASGFTFG QFGMSWVRQA PAKGPERVSA ISSDASGTIY   60
ADSVKGRFTI SRDNAKNTLY LQMNSLKPED TAVYYCTIGS STTPSGPGQG TQVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 28           moltype = AA  length = 348
FEATURE                 Location/Qualifiers
source                  1..348
                        mol_type = protein
                        organism = synthetic construct
SEQUENCE: 28
QVQLVESGGG LVQPGGSLRL SCAASGFTFG QFGMSWVRQA PAKGPERVSA ISSDSSGTIY   60
ADSVKGRFTI SRDNAKNTLY LQMNSLKPED TAVYYCTIGS STTPSGPGQG TQVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 29           moltype = AA  length = 348
FEATURE                 Location/Qualifiers
source                  1..348
                        mol_type = protein
                        organism = synthetic construct
```

```
SEQUENCE: 29
EVQLVESGGG LVQPGGSLRL SCAASGFTFG QFGMSWVRQA PGKGLEWVSA ISSDGSGTIY  60
ADSVKGRFTI SRDNSKNTLY LQMNSLRAED TAVYYCTIGS STTPSGWGQG TTVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG            348

SEQ ID NO: 30       moltype = AA   length = 348
FEATURE             Location/Qualifiers
source              1..348
                    mol_type = protein
                    organism = synthetic construct
SEQUENCE: 30
EVQLVESGGG LVQPGGSLRL SCAASGFTFG QFGMSWVRQA PGKGLEWVSA ISSDGSGTIY  60
ADSVKGRFTI SRDNSKNTLY LQMNSLRAED TAVYYCTIGS STTPSGPGQG TTVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG            348

SEQ ID NO: 31       moltype = AA   length = 348
FEATURE             Location/Qualifiers
source              1..348
                    mol_type = protein
                    organism = synthetic construct
SEQUENCE: 31
EVQLVESGGG LVQPGGSLRL SCAASGFTFG QFGMSWFRQA PGKEREFVSA ISSDGSGTIY  60
ADSVKGRFTI SRDNSKNTLY LQMNSLRAED TAVYYCTIGS STTPSGWGQG TTVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG            348

SEQ ID NO: 32       moltype = AA   length = 348
FEATURE             Location/Qualifiers
source              1..348
                    mol_type = protein
                    organism = synthetic construct
SEQUENCE: 32
EVQLVESGGG LVQPGGSLRL SCAASGFTFG QFGMSWFRQA PGKEREFVSA ISSDGSGTIY  60
ADSVKGRFTI SRDNSKNTLY LQMNSLRAED TAVYYCTIGS STTPSGPGQG TTVTVSSGGG  120
GSDKTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG            348

SEQ ID NO: 33       moltype = AA   length = 346
FEATURE             Location/Qualifiers
source              1..346
                    mol_type = protein
                    organism = synthetic construct
SEQUENCE: 33
EVQLLESGGG LVQPGGSLRL SCAASGFTFR SFGMSWVRQA PGKGPEWVSS ISGSGSDTLY  60
ADSVKGRFTI SRDNSKNTLY LQMNSLRPED TAVYYCTIGG SLSRSSQGTL VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG            346

SEQ ID NO: 34       moltype = AA   length = 348
FEATURE             Location/Qualifiers
source              1..348
                    mol_type = protein
                    organism = synthetic construct
SEQUENCE: 34
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SQVQLVESGG  240
GLVQPGGSLR LSCAASGFTF GQFGMSWVRQ APAKGPERVS AISSDGSGTI YADSVKGRFT  300
ISRDNAKNTL YLQMNSLKPE DTAVYYCTIG SSTTPSGPGQ GTQVTVSS            348

SEQ ID NO: 35       moltype = AA   length = 348
FEATURE             Location/Qualifiers
source              1..348
                    mol_type = protein
                    organism = synthetic construct
SEQUENCE: 35
```

-continued

```
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF GQFGMSWVRQ APGKGPERVS AISSDGSGTI YADSVKGRFT  300
ISRDNSKNTL YLQMNSLRPE DTAVYYCTIG SSTTPSGPGQ GTLVTVSS              348

SEQ ID NO: 36           moltype = AA  length = 348
FEATURE                 Location/Qualifiers
source                  1..348
                        mol_type = protein
                        organism = synthetic construct
SEQUENCE: 36
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF SQFGMSWVRQ APGKGPERVS AISSDGSGTI YADSVKGRFT  300
ISRDNSKNTL YLQMNSLRPE DTAVYYCTIG SSTTPSGPGQ GTLVTVSS              348

SEQ ID NO: 37           moltype = AA  length = 348
FEATURE                 Location/Qualifiers
source                  1..348
                        mol_type = protein
                        organism = synthetic construct
SEQUENCE: 37
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SQVQLVESGG  240
GLVQPGGSLR LSCAASGFTF GQFGMSWVRQ APAKGPERVS AISSSGSGTI YADSVKGRFT  300
ISRDNAKNTL YLQMNSLKPE DTAVYYCTIG SSTTPSGPGQ GTQVTVSS              348

SEQ ID NO: 38           moltype = AA  length = 348
FEATURE                 Location/Qualifiers
source                  1..348
                        mol_type = protein
                        organism = synthetic construct
SEQUENCE: 38
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SQVQLVESGG  240
GLVQPGGSLR LSCAASGFTF GQFGMSWVRQ APAKGPERVS AISSGGSGTI YADSVKGRFT  300
ISRDNAKNTL YLQMNSLKPE DTAVYYCTIG SSTTPSGPGQ GTQVTVSS              348

SEQ ID NO: 39           moltype = AA  length = 348
FEATURE                 Location/Qualifiers
source                  1..348
                        mol_type = protein
                        organism = synthetic construct
SEQUENCE: 39
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SQVQLVESGG  240
GLVQPGGSLR LSCAASGFTF GQFGMSWVRQ APAKGPERVS AISSDASGTI YADSVKGRFT  300
ISRDNAKNTL YLQMNSLKPE DTAVYYCTIG SSTTPSGPGQ GTQVTVSS              348

SEQ ID NO: 40           moltype = AA  length = 348
FEATURE                 Location/Qualifiers
source                  1..348
                        mol_type = protein
                        organism = synthetic construct
SEQUENCE: 40
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SQVQLVESGG  240
GLVQPGGSLR LSCAASGFTF GQFGMSWVRQ APAKGPERVS AISSDSSGTI YADSVKGRFT  300
ISRDNAKNTL YLQMNSLKPE DTAVYYCTIG SSTTPSGPGQ GTQVTVSS              348

SEQ ID NO: 41           moltype = AA  length = 348
FEATURE                 Location/Qualifiers
source                  1..348
                        mol_type = protein
                        organism = synthetic construct
SEQUENCE: 41
DKTHTCPPCP APELLGGPSV FLFPPKPKDT LMISRTPEVT CVVVDVSHED PEVKFNWYVD   60
```

-continued

```
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GQFGMSWVRQ APGKGLEWVS AISSDGSGTI YADSVKGRFT   300
ISRDNSKNTL YLQMNSLRAE DTAVYYCTIG SSTTPSGWGQ GTTVTVSS             348

SEQ ID NO: 42              moltype = AA   length = 348
FEATURE                    Location/Qualifiers
source                     1..348
                           mol_type = protein
                           organism = synthetic construct
SEQUENCE: 42
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GQFGMSWVRQ APGKGLEWVS AISSDGSGTI YADSVKGRFT   300
ISRDNSKNTL YLQMNSLRAE DTAVYYCTIG SSTTPSGPGQ GTTVTVSS             348

SEQ ID NO: 43              moltype = AA   length = 348
FEATURE                    Location/Qualifiers
source                     1..348
                           mol_type = protein
                           organism = synthetic construct
SEQUENCE: 43
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GQFGMSWFRQ APGKEREFVS AISSDGSGTI YADSVKGRFT   300
ISRDNSKNTL YLQMNSLRAE DTAVYYCTIG SSTTPSGWGQ GTTVTVSS             348

SEQ ID NO: 44              moltype = AA   length = 348
FEATURE                    Location/Qualifiers
source                     1..348
                           mol_type = protein
                           organism = synthetic construct
SEQUENCE: 44
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GQFGMSWFRQ APGKEREFVS AISSDGSGTI YADSVKGRFT   300
ISRDNSKNTL YLQMNSLRAE DTAVYYCTIG SSTTPSGPGQ GTTVTVSS             348

SEQ ID NO: 45              moltype = AA   length = 346
FEATURE                    Location/Qualifiers
source                     1..346
                           mol_type = protein
                           organism = synthetic construct
SEQUENCE: 45
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLLESGG   240
GLVQPGGSLR LSCAASGFTF RSFGMSWVRQ APGKGPEWVS SISGSGSDTL YADSVKGRFT   300
ISRDNSKNTL YLQMNSLRPE DTAVYYCTIG GSLSRSSQGT LVTVSS              346

SEQ ID NO: 46              moltype = AA   length = 127
FEATURE                    Location/Qualifiers
source                     1..127
                           mol_type = protein
                           organism = synthetic construct
SEQUENCE: 46
EVQLLESGGG LVQPGGSLRL SCAASGFTFG QFGMSWVRQA PGKGPERVSA ISSDGSGTIY   60
ADSVKGRFTI SRDNSKNTLY LQMNSLRPED TAVYYCTIGS STTPSGPGQG TLVTVSSGGH   120
HHHHHHH                                                         127

SEQ ID NO: 47              moltype = AA   length = 127
FEATURE                    Location/Qualifiers
source                     1..127
                           mol_type = protein
                           organism = synthetic construct
SEQUENCE: 47
EVQLLESGGG LVQPGGSLRL SCAASGFTFS QFGMSWVRQA PGKGPERVSA ISSDGSGTIY   60
ADSVKGRFTI SRDNSKNTLY LQMNSLRPED TAVYYCTIGS STTPSGPGQG TLVTVSSGGH   120
HHHHHHH                                                         127

SEQ ID NO: 48              moltype = AA   length = 127
```

-continued

```
FEATURE              Location/Qualifiers
source               1..127
                     mol_type = protein
                     organism = synthetic construct
SEQUENCE: 48
QVQLVESGGG LVQPGGSLRL SCAASGFTFG QFGMSWVRQA PAKGPERVSA ISSSGSGTIY   60
ADSVKGRFTI SRDNAKNTLY LQMNSLKPED TAVYYCTIGS STTPSGPGQG TQVTVSSGGH   120
HHHHHHH                                                            127

SEQ ID NO: 49        moltype = AA  length = 127
FEATURE              Location/Qualifiers
source               1..127
                     mol_type = protein
                     organism = synthetic construct
SEQUENCE: 49
QVQLVESGGG LVQPGGSLRL SCAASGFTFG QFGMSWVRQA PAKGPERVSA ISSGGSGTIY   60
ADSVKGRFTI SRDNAKNTLY LQMNSLKPED TAVYYCTIGS STTPSGPGQG TQVTVSSGGH   120
HHHHHHH                                                            127

SEQ ID NO: 50        moltype = AA  length = 127
FEATURE              Location/Qualifiers
source               1..127
                     mol_type = protein
                     organism = synthetic construct
SEQUENCE: 50
QVQLVESGGG LVQPGGSLRL SCAASGFTFG QFGMSWVRQA PAKGPERVSA ISSDASGTIY   60
ADSVKGRFTI SRDNAKNTLY LQMNSLKPED TAVYYCTIGS STTPSGPGQG TQVTVSSGGH   120
HHHHHHH                                                            127

SEQ ID NO: 51        moltype = AA  length = 127
FEATURE              Location/Qualifiers
source               1..127
                     mol_type = protein
                     organism = synthetic construct
SEQUENCE: 51
QVQLVESGGG LVQPGGSLRL SCAASGFTFG QFGMSWVRQA PAKGPERVSA ISSDSSGTIY   60
ADSVKGRFTI SRDNAKNTLY LQMNSLKPED TAVYYCTIGS STTPSGPGQG TQVTVSSGGH   120
HHHHHHH                                                            127

SEQ ID NO: 52        moltype = AA  length = 127
FEATURE              Location/Qualifiers
source               1..127
                     mol_type = protein
                     organism = synthetic construct
SEQUENCE: 52
EVQLVESGGG LVQPGGSLRL SCAASGFTFG QFGMSWVRQA PGKGLEWVSA ISSDGSGTIY   60
ADSVKGRFTI SRDNSKNTLY LQMNSLRAED TAVYYCTIGS STTPSGWGQG TTVTVSSGGH   120
HHHHHHH                                                            127

SEQ ID NO: 53        moltype = AA  length = 127
FEATURE              Location/Qualifiers
source               1..127
                     mol_type = protein
                     organism = synthetic construct
SEQUENCE: 53
EVQLVESGGG LVQPGGSLRL SCAASGFTFG QFGMSWVRQA PGKGLEWVSA ISSDGSGTIY   60
ADSVKGRFTI SRDNSKNTLY LQMNSLRAED TAVYYCTIGS STTPSGPGQG TTVTVSSGGH   120
HHHHHHH                                                            127

SEQ ID NO: 54        moltype = AA  length = 127
FEATURE              Location/Qualifiers
source               1..127
                     mol_type = protein
                     organism = synthetic construct
SEQUENCE: 54
EVQLVESGGG LVQPGGSLRL SCAASGFTFG QFGMSWFRQA PGKEREFVSA ISSDGSGTIY   60
ADSVKGRFTI SRDNSKNTLY LQMNSLRAED TAVYYCTIGS STTPSGWGQG TTVTVSSGGH   120
HHHHHHH                                                            127

SEQ ID NO: 55        moltype = AA  length = 127
FEATURE              Location/Qualifiers
source               1..127
                     mol_type = protein
                     organism = synthetic construct
SEQUENCE: 55
EVQLVESGGG LVQPGGSLRL SCAASGFTFG QFGMSWFRQA PGKEREFVSA ISSDGSGTIY   60
ADSVKGRFTI SRDNSKNTLY LQMNSLRAED TAVYYCTIGS STTPSGPGQG TTVTVSSGGH   120
HHHHHHH                                                            127
```

-continued

```
SEQ ID NO: 56          moltype = AA   length = 226
FEATURE                Location/Qualifiers
source                 1..226
                       mol_type = protein
                       organism = synthetic construct
SEQUENCE: 56
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 57          moltype = AA   length = 16
FEATURE                Location/Qualifiers
source                 1..16
                       mol_type = protein
                       organism = synthetic construct
VARIANT                6
                       note = G, A, or S
SEQUENCE: 57
AISSDXSGTI YADVKG                                                   16

SEQ ID NO: 58          moltype = AA   length = 5
FEATURE                Location/Qualifiers
source                 1..5
                       mol_type = protein
                       organism = synthetic construct
SEQUENCE: 58
GGGGS                                                                5

SEQ ID NO: 59          moltype = AA   length = 5
FEATURE                Location/Qualifiers
source                 1..5
                       mol_type = protein
                       organism = synthetic construct
SEQUENCE: 59
GSGGS                                                                5

SEQ ID NO: 60          moltype = AA   length = 7
FEATURE                Location/Qualifiers
source                 1..7
                       mol_type = protein
                       organism = synthetic construct
SEQUENCE: 60
GSGGGGS                                                              7

SEQ ID NO: 61          moltype = AA   length = 10
FEATURE                Location/Qualifiers
source                 1..10
                       mol_type = protein
                       organism = synthetic construct
SEQUENCE: 61
GGGGSGGGGS                                                          10

SEQ ID NO: 62          moltype = AA   length = 15
FEATURE                Location/Qualifiers
source                 1..15
                       mol_type = protein
                       organism = synthetic construct
SEQUENCE: 62
GGGGSGGGGS GGGGS                                                    15

SEQ ID NO: 63          moltype = AA   length = 20
FEATURE                Location/Qualifiers
source                 1..20
                       mol_type = protein
                       organism = synthetic construct
SEQUENCE: 63
GGGGSGGGGS GGGGSGGGGS                                               20

SEQ ID NO: 64          moltype = AA   length = 25
FEATURE                Location/Qualifiers
source                 1..25
                       mol_type = protein
                       organism = synthetic construct
SEQUENCE: 64
GGGGSGGGGS GGGGSGGGGS GGGGS                                         25

SEQ ID NO: 65          moltype = AA   length = 7
FEATURE                Location/Qualifiers
```

-continued

```
source                      1..7
                            mol_type = protein
                            organism = synthetic construct
SEQUENCE: 65
GGGGSSA                                                                    7

SEQ ID NO: 66               moltype = AA   length = 12
FEATURE                     Location/Qualifiers
source                      1..12
                            mol_type = protein
                            organism = synthetic construct
SEQUENCE: 66
GSGGGGSGGG GS                                                              12

SEQ ID NO: 67               moltype = AA   length = 4
FEATURE                     Location/Qualifiers
source                      1..4
                            mol_type = protein
                            organism = synthetic construct
SEQUENCE: 67
GGGS                                                                       4

SEQ ID NO: 68               moltype = AA   length = 5
FEATURE                     Location/Qualifiers
source                      1..5
                            mol_type = protein
                            organism = synthetic construct
SEQUENCE: 68
GGGGG                                                                      5

SEQ ID NO: 69               moltype = AA   length = 6
FEATURE                     Location/Qualifiers
source                      1..6
                            mol_type = protein
                            organism = synthetic construct
SEQUENCE: 69
GGSGGD                                                                     6

SEQ ID NO: 70               moltype = AA   length = 6
FEATURE                     Location/Qualifiers
source                      1..6
                            mol_type = protein
                            organism = synthetic construct
SEQUENCE: 70
GGSGGE                                                                     6

SEQ ID NO: 71               moltype = AA   length = 11
FEATURE                     Location/Qualifiers
source                      1..11
                            mol_type = protein
                            organism = synthetic construct
SEQUENCE: 71
GGGSGSGGGG S                                                               11

SEQ ID NO: 72               moltype = AA   length = 11
FEATURE                     Location/Qualifiers
source                      1..11
                            mol_type = protein
                            organism = synthetic construct
SEQUENCE: 72
GGGGGPGGGG P                                                               11

SEQ ID NO: 73               moltype = AA   length = 12
FEATURE                     Location/Qualifiers
source                      1..12
                            mol_type = protein
                            organism = synthetic construct
SEQUENCE: 73
GGGGSGGGSA AA                                                              12

SEQ ID NO: 74               moltype = AA   length = 8
FEATURE                     Location/Qualifiers
source                      1..8
                            mol_type = protein
                            organism = synthetic construct
SEQUENCE: 74
HHHHHHHH                                                                   8

SEQ ID NO: 75               moltype = AA   length = 115
```

```
FEATURE                 Location/Qualifiers
source                  1..115
                        mol_type = protein
                        organism = synthetic construct
SEQUENCE: 75
QVQLVESGGG LVQPGGSLRL SCAASGFTFG RFGMSWVRQA PGKGPEWVSA IDSGGADTRY   60
AESVKGRFTI SRDNAKKTLY LQMNSLKPED TAVYYCTIGR STSRGSQGTQ VTVSS        115

SEQ ID NO: 76           moltype = AA  length = 115
FEATURE                 Location/Qualifiers
source                  1..115
                        mol_type = protein
                        organism = synthetic construct
SEQUENCE: 76
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGQ STSRGSQGTQ VTVSS        115

SEQ ID NO: 77           moltype = AA  length = 115
FEATURE                 Location/Qualifiers
source                  1..115
                        mol_type = protein
                        organism = synthetic construct
SEQUENCE: 77
QVQLQESGGG LVQPGGSLRL SCAASGFTFG SFGMSWVRQA PGKGPEWVSA IDSGGADTRY   60
AESVKGRFTI SRDNAKSTLY LQMNSLKPED TAVYYCTIGR SSSRGSQGTQ VTVSS        115

SEQ ID NO: 78           moltype = AA  length = 115
FEATURE                 Location/Qualifiers
source                  1..115
                        mol_type = protein
                        organism = synthetic construct
SEQUENCE: 78
EVQLVESGGG LVQPGGSLRL SCAASGFTFG SFGMSWVRQA PGKGPEWVSA IDSGGTDTRY   60
AESIKGRFTI SRDNAKKTLY LQMNSLKPED TAVYYCTIGQ STSRGSQGTQ VTVSS        115

SEQ ID NO: 79           moltype = AA  length = 115
FEATURE                 Location/Qualifiers
source                  1..115
                        mol_type = protein
                        organism = synthetic construct
SEQUENCE: 79
QVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGQ STSRGSQGTQ VTVSS        115

SEQ ID NO: 80           moltype = AA  length = 115
FEATURE                 Location/Qualifiers
source                  1..115
                        mol_type = protein
                        organism = synthetic construct
SEQUENCE: 80
EVQLVESGGG LVQSGGSLRL SCAASGFTFG SFGMSWVRQA PGKGPEWVSA IDGGGADTRY   60
AESVKGRFTI SRDNAKKTLY LQMNSLKPED TAVYYCTIGQ STSRGSQGTQ VTVSS        115

SEQ ID NO: 81           moltype = AA  length = 115
FEATURE                 Location/Qualifiers
source                  1..115
                        mol_type = protein
                        organism = synthetic construct
SEQUENCE: 81
EVQLVESGGG LVQPGGSLRL SCAASGFTFG SFGMSWVRQA PGKGPEWVSA IDSSGADTRY   60
AESVKGRFTI SRDNAKKTLY LQMNSLKPED TAVYYCTIGR STSRRNQGTQ VTVAS        115

SEQ ID NO: 82           moltype = AA  length = 115
FEATURE                 Location/Qualifiers
source                  1..115
                        mol_type = protein
                        organism = synthetic construct
SEQUENCE: 82
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGR STSRGSQGTQ VTVSS        115

SEQ ID NO: 83           moltype = AA  length = 115
FEATURE                 Location/Qualifiers
source                  1..115
                        mol_type = protein
                        organism = synthetic construct
SEQUENCE: 83
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGR SASRGSQGTQ VTVSS        115
```

-continued

```
SEQ ID NO: 84              moltype = AA   length = 115
FEATURE                    Location/Qualifiers
source                     1..115
                           mol_type = protein
                           organism = synthetic construct
SEQUENCE: 84
QVQLVESGGG LVQPGGSLRL SCAASGFTFG SFGMSWVRQA PGKGPEWVSA IDSGGADTRY    60
AETVKGRFTI SRDNLKKTLY LQMNSLKPED TAVYYCTIGR STSRGSQGTQ VTVSS         115

SEQ ID NO: 85              moltype = AA   length = 115
FEATURE                    Location/Qualifiers
source                     1..115
                           mol_type = protein
                           organism = synthetic construct
SEQUENCE: 85
QVQLVESGGG LVQPGGSLRL SCAASGFTFG SFGMSWVRQA PGKGPEWVSA IDSGGGDTRY    60
SDSVKGRFAI SRDNAKKTLY LQMNSLKPED TAAYYCTIGR STSRGSQGTQ VTVSS         115

SEQ ID NO: 86              moltype = AA   length = 115
FEATURE                    Location/Qualifiers
source                     1..115
                           mol_type = protein
                           organism = synthetic construct
SEQUENCE: 86
EVQLVESGGG LVQAGGSLRL SCAASGFTFG SFGMSWVRQV PGKGPEWVSA IDSGGTDTRY    60
AESIKGRFII SRDNAKKTLY LQMNSLKPED TAVYYCTIGQ STSRGSQGTQ VTVSS         115

SEQ ID NO: 87              moltype = AA   length = 115
FEATURE                    Location/Qualifiers
source                     1..115
                           mol_type = protein
                           organism = synthetic construct
SEQUENCE: 87
QVQLVESGGG LVQPGGSLRL SCAASGFTFG SFGMSWVRQA PGKGPEWVSA IDSGGGDTRY    60
AESVKGRFTI SRDNAKKTLY LQMNSLKPED TAVYYCTIGR STSRVGQGTQ VTVSS         115

SEQ ID NO: 88              moltype = AA   length = 115
FEATURE                    Location/Qualifiers
source                     1..115
                           mol_type = protein
                           organism = synthetic construct
SEQUENCE: 88
QVQLQESGGG LVQPGGSLTL SCAASGFTFG SFGMSWVRQA PGKGPEWVSA IDSSGADTRY    60
ADSVKGRFTI SRDNAKKTLY LQMNSLKPED TAVYYCTIGR STSRGSQGTQ VTVSS         115

SEQ ID NO: 89              moltype = AA   length = 115
FEATURE                    Location/Qualifiers
source                     1..115
                           mol_type = protein
                           organism = synthetic construct
SEQUENCE: 89
EVQLVESGGG LVQPGGSLRL SCAASGFTFG SFGMSWVRQA PGKGPEWVSA IDSGGADTRY    60
AESVKGRFTI SRDNAKKTLY LQMNNLKPED TAMYYCTIGR STSRGSQGTQ VTVSS         115

SEQ ID NO: 90              moltype = AA   length = 115
FEATURE                    Location/Qualifiers
source                     1..115
                           mol_type = protein
                           organism = synthetic construct
SEQUENCE: 90
QVQLQESGGG LVQPGDSLRL SCAASGFTFG SFGMSWVRQA PGREPEWVSA IDSGGADTRY    60
AESVKGRFTI SRDNAKKTLY LQMNTLKPED TAVYYCTIGR STSRGSQGTQ VTVSS         115

SEQ ID NO: 91              moltype = AA   length = 115
FEATURE                    Location/Qualifiers
source                     1..115
                           mol_type = protein
                           organism = synthetic construct
SEQUENCE: 91
QVQLVESGGG LVQPGGSLRL SCAASGFTFG SFGMSWVRQA PGKGPEWVSA IDSGGTDTRY    60
AESIKGRFTI SRDNAKKTLY LQMNSLKPED TAVYYCTIGQ STSRGSQGTQ VTVSS         115

SEQ ID NO: 92              moltype = AA   length = 115
FEATURE                    Location/Qualifiers
source                     1..115
                           mol_type = protein
                           organism = synthetic construct
SEQUENCE: 92
```

```
QVQLVESGGG LVQPGGSLRL SCAASGFTFG SFGMSWVRQA PGKGPEWVSA IDSGGGVTLY 60
AESVKGRFTI SRDNAKKTLY LQMNSLKSED TAVYYCTIGQ STSRGSQGTQ VTVSS       115

SEQ ID NO: 93            moltype = AA  length = 115
FEATURE                  Location/Qualifiers
source                   1..115
                         mol_type = protein
                         organism = synthetic construct
SEQUENCE: 93
QVQLVESGGG LVQPGGSLRL SCAASGFTFG SFGMSWVRQA PGKGPEWVSA IDGGGADTRY 60
AESVKGRFTI SRDNAKKTLY LQMNSLKPED TAVYYCTIGG STSRGSQGTQ VTVSS       115

SEQ ID NO: 94            moltype = AA  length = 115
FEATURE                  Location/Qualifiers
source                   1..115
                         mol_type = protein
                         organism = synthetic construct
SEQUENCE: 94
QVQLVESGGG LVQPGGSLRL SCAASGFSFG SFGMSWVRQA PGKGPEWVSA IDSGGADTRY 60
AETVKGRFTI SRDNAKKTLY LQMNSLKPED TAVYYCTIGR STSRGSQGTQ VTVSS       115

SEQ ID NO: 95            moltype = AA  length = 115
FEATURE                  Location/Qualifiers
source                   1..115
                         mol_type = protein
                         organism = synthetic construct
SEQUENCE: 95
QVQLVESGGG LVQAGGSLRL SCAASGFTFG SFGMSWVRQA PGKGPEWVSA IDSGGVDTRY 60
AESVKGRFTI SRDNAKKTLY LQMNSLKPED TAVYYCTIGQ STSRGSQGTQ VTVSS       115

SEQ ID NO: 96            moltype = AA  length = 115
FEATURE                  Location/Qualifiers
source                   1..115
                         mol_type = protein
                         organism = synthetic construct
SEQUENCE: 96
QVQLQESGGG LVQPGGSLRL SCAASGFTFG SFGMSWVRQA PGKGPEWVSA IDSSGADTRY 60
AESVKGRFTI SRDNAKKTLY LQMNSLNPDD TAVYYCTIGQ SISRGSQGTQ VTVSS       115

SEQ ID NO: 97            moltype = AA  length = 115
FEATURE                  Location/Qualifiers
source                   1..115
                         mol_type = protein
                         organism = synthetic construct
SEQUENCE: 97
QVQLVESGGG LVQPGGSLRL SCAASGFTFG SFGMSWVRQA PGKGPEWVSA IDSSGADTIY 60
AESVKGRFTI ARDNAKKTLY LQMNSLKPED TAVYYCTIGQ SISRGSQGTQ VTVSS       115

SEQ ID NO: 98            moltype = AA  length = 115
FEATURE                  Location/Qualifiers
source                   1..115
                         mol_type = protein
                         organism = synthetic construct
SEQUENCE: 98
EVQLVESGGG LVQSGGSLRL SCAASGFTFG SFGMSWVRQA PGKGPEWVSA VDSGGADTRY 60
AESVKGRFTI SRDNAKKTLY LQMNSLKPED TAVYYCTIGQ STTRGSQGTQ VTVSS       115

SEQ ID NO: 99            moltype = AA  length = 115
FEATURE                  Location/Qualifiers
source                   1..115
                         mol_type = protein
                         organism = synthetic construct
SEQUENCE: 99
EVQLVESGGG LVQPGGSLRL SCAASGFTFG SFGMGWSRQA PGKGPEWVAA INSGGDTTLY 60
ADSVKGRFTI SRDNAKNTLY LEMNSLKPED TAVYYCTIGR GSSRGSQGTQ VTVSS       115

SEQ ID NO: 100           moltype = AA  length = 115
FEATURE                  Location/Qualifiers
source                   1..115
                         mol_type = protein
                         organism = synthetic construct
SEQUENCE: 100
QVQLVESGGG LVQPGGSLRL SCAASGFTFG SFGMSWVRQA PGKGPEWVSA IDSGGADTRY 60
TESVKGRFTI SRDNAKKTLY LQMNSLKPED TAVYYCTIGR SISRGSQGTQ VTVSS       115

SEQ ID NO: 101           moltype = AA  length = 115
FEATURE                  Location/Qualifiers
source                   1..115
                         mol_type = protein
```

```
                        organism = synthetic construct
SEQUENCE: 101
QVQLVESGGG LVQPGGSLRL SCAASGFSFG SFGMSWVRQA PGKGPEWVSA IDSGGADTRY    60
AETVKGRFTI SRDNAKKTLY LQMNSLKPED TAVYYCTIGR STTRGSQGTQ VTVSS        115

SEQ ID NO: 102          moltype = AA  length = 17
FEATURE                 Location/Qualifiers
source                  1..17
                        mol_type = protein
                        organism = synthetic construct
VARIANT                 2
                        note = I or V
VARIANT                 3
                        note = D, N or S
VARIANT                 4
                        note = S or G
VARIANT                 5
                        note = G, S or D
VARIANT                 7
                        note = A, T, V, D, or G
VARIANT                 8
                        note = D, V, or T
VARIANT                 10
                        note = R, L, or I
VARIANT                 12
                        note = A, S, or T
VARIANT                 13
                        note = E or D
VARIANT                 14
                        note = S or T
VARIANT                 15
                        note = V or I
SEQUENCE: 102
AXXXXGXXTX YXXXXKG                                                   17

SEQ ID NO: 103          moltype = AA  length = 5
FEATURE                 Location/Qualifiers
source                  1..5
                        mol_type = protein
                        organism = synthetic construct
SEQUENCE: 103
RFGMS                                                                5

SEQ ID NO: 104          moltype = AA  length = 5
FEATURE                 Location/Qualifiers
source                  1..5
                        mol_type = protein
                        organism = synthetic construct
SEQUENCE: 104
SFGMS                                                                5

SEQ ID NO: 105          moltype = AA  length = 17
FEATURE                 Location/Qualifiers
source                  1..17
                        mol_type = protein
                        organism = synthetic construct
SEQUENCE: 105
AIDSGGADTR YAESVKG                                                   17

SEQ ID NO: 106          moltype = AA  length = 17
FEATURE                 Location/Qualifiers
source                  1..17
                        mol_type = protein
                        organism = synthetic construct
SEQUENCE: 106
AIDSGGTDTR YAESIKG                                                   17

SEQ ID NO: 107          moltype = AA  length = 17
FEATURE                 Location/Qualifiers
source                  1..17
                        mol_type = protein
                        organism = synthetic construct
SEQUENCE: 107
AIDGGGADTR YAESVKG                                                   17

SEQ ID NO: 108          moltype = AA  length = 17
FEATURE                 Location/Qualifiers
source                  1..17
                        mol_type = protein
```

```
                               organism = synthetic construct
SEQUENCE: 108
AIDSSGADTR YAESVKG                                                     17

SEQ ID NO: 109          moltype = AA  length = 17
FEATURE                 Location/Qualifiers
source                  1..17
                        mol_type = protein
                        organism = synthetic construct
SEQUENCE: 109
AIDSGGADTR YAETVKG                                                     17

SEQ ID NO: 110          moltype = AA  length = 17
FEATURE                 Location/Qualifiers
source                  1..17
                        mol_type = protein
                        organism = synthetic construct
SEQUENCE: 110
AIDSGGGDTR YSDSVKG                                                     17

SEQ ID NO: 111          moltype = AA  length = 17
FEATURE                 Location/Qualifiers
source                  1..17
                        mol_type = protein
                        organism = synthetic construct
SEQUENCE: 111
AIDSGGGDTR YAESVKG                                                     17

SEQ ID NO: 112          moltype = AA  length = 17
FEATURE                 Location/Qualifiers
source                  1..17
                        mol_type = protein
                        organism = synthetic construct
SEQUENCE: 112
AIDSSGADTR YADSVKG                                                     17

SEQ ID NO: 113          moltype = AA  length = 17
FEATURE                 Location/Qualifiers
source                  1..17
                        mol_type = protein
                        organism = synthetic construct
SEQUENCE: 113
AIDSGGGVTL YAESVKG                                                     17

SEQ ID NO: 114          moltype = AA  length = 17
FEATURE                 Location/Qualifiers
source                  1..17
                        mol_type = protein
                        organism = synthetic construct
SEQUENCE: 114
AIDSGGVDTR YAESVKG                                                     17

SEQ ID NO: 115          moltype = AA  length = 17
FEATURE                 Location/Qualifiers
source                  1..17
                        mol_type = protein
                        organism = synthetic construct
SEQUENCE: 115
AIDSSGADTI YAESVKG                                                     17

SEQ ID NO: 116          moltype = AA  length = 17
FEATURE                 Location/Qualifiers
source                  1..17
                        mol_type = protein
                        organism = synthetic construct
SEQUENCE: 116
AVDSGGADTR YAESVKG                                                     17

SEQ ID NO: 117          moltype = AA  length = 17
FEATURE                 Location/Qualifiers
source                  1..17
                        mol_type = protein
                        organism = synthetic construct
SEQUENCE: 117
AINSGGDTTL YADSVKG                                                     17

SEQ ID NO: 118          moltype = AA  length = 17
FEATURE                 Location/Qualifiers
source                  1..17
```

-continued

```
                              mol_type = protein
                              organism = synthetic construct
SEQUENCE: 118
AIDSGGADTR YTESVKG                                            17

SEQ ID NO: 119      moltype = AA   length = 6
FEATURE             Location/Qualifiers
source              1..6
                    mol_type = protein
                    organism = synthetic construct
SEQUENCE: 119
GRSTSR                                                        6

SEQ ID NO: 120      moltype = AA   length = 6
FEATURE             Location/Qualifiers
source              1..6
                    mol_type = protein
                    organism = synthetic construct
SEQUENCE: 120
GQSTSR                                                        6

SEQ ID NO: 121      moltype = AA   length = 6
FEATURE             Location/Qualifiers
source              1..6
                    mol_type = protein
                    organism = synthetic construct
SEQUENCE: 121
GRSSSR                                                        6

SEQ ID NO: 122      moltype = AA   length = 6
FEATURE             Location/Qualifiers
source              1..6
                    mol_type = protein
                    organism = synthetic construct
SEQUENCE: 122
GRSASR                                                        6

SEQ ID NO: 123      moltype = AA   length = 6
FEATURE             Location/Qualifiers
source              1..6
                    mol_type = protein
                    organism = synthetic construct
SEQUENCE: 123
GGSTSR                                                        6

SEQ ID NO: 124      moltype = AA   length = 6
FEATURE             Location/Qualifiers
source              1..6
                    mol_type = protein
                    organism = synthetic construct
SEQUENCE: 124
GQSISR                                                        6

SEQ ID NO: 125      moltype = AA   length = 6
FEATURE             Location/Qualifiers
source              1..6
                    mol_type = protein
                    organism = synthetic construct
SEQUENCE: 125
GQSTTR                                                        6

SEQ ID NO: 126      moltype = AA   length = 6
FEATURE             Location/Qualifiers
source              1..6
                    mol_type = protein
                    organism = synthetic construct
SEQUENCE: 126
GRGSSR                                                        6

SEQ ID NO: 127      moltype = AA   length = 6
FEATURE             Location/Qualifiers
source              1..6
                    mol_type = protein
                    organism = synthetic construct
SEQUENCE: 127
GRSISR                                                        6

SEQ ID NO: 128      moltype = AA   length = 6
FEATURE             Location/Qualifiers
```

-continued

```
source                 1..6
                       mol_type = protein
                       organism = synthetic construct
SEQUENCE: 128
GRSTTR                                                               6

SEQ ID NO: 129         moltype = AA  length = 5
FEATURE                Location/Qualifiers
source                 1..5
                       mol_type = protein
                       organism = synthetic construct
SEQUENCE: 129
SFGMG                                                                5

SEQ ID NO: 130         moltype = AA  length = 115
FEATURE                Location/Qualifiers
source                 1..115
                       mol_type = protein
                       organism = synthetic construct
SEQUENCE: 130
EVQLLESGGG LVQPGGSLRL SCAASGFTFG SFGMSWVRQA PGKGPEWVSA IDSGGADTRY   60
AESVKGRFTI SRDNSKNTLY LQMNSLRPED TAVYYCTIGR SASRGSQGTL VTVSS        115

SEQ ID NO: 131         moltype = AA  length = 115
FEATURE                Location/Qualifiers
source                 1..115
                       mol_type = protein
                       organism = synthetic construct
SEQUENCE: 131
EVQLLESGGG LVQPGGSLRL SCAASGFTFS SFGMSWVRQA PGKGPEWVSA IDSGGADTRY   60
AESVKGRFTI SRDNSKNTLY LQMNSLRPED TAVYYCTIGR SASRGSQGTL VTVSS        115

SEQ ID NO: 132         moltype = AA  length = 115
FEATURE                Location/Qualifiers
source                 1..115
                       mol_type = protein
                       organism = synthetic construct
SEQUENCE: 132
EVQLLESGGG LVQPGGSLRL SCAASGFTFG SFGMSWVRQA PGKGPEWVSA IDSGGADTRY   60
AESVKGRFTI SRDNSKNTLY LQMNSLRPED TAVYYCTIGR SASRSSQGTL VTVSS        115

SEQ ID NO: 133         moltype = AA  length = 115
FEATURE                Location/Qualifiers
source                 1..115
                       mol_type = protein
                       organism = synthetic construct
SEQUENCE: 133
EVQLVESGGG LVQPGGSLRL SCAASGFTFG SFGMSWVRQA PGKGLEWVSA IDSGGADTRY   60
AESVKGRFTI SRDNSKNTLY LQMNSLRAED TAVYYCTIGR SASRWGQGTT VTVSS        115

SEQ ID NO: 134         moltype = AA  length = 115
FEATURE                Location/Qualifiers
source                 1..115
                       mol_type = protein
                       organism = synthetic construct
SEQUENCE: 134
EVQLVESGGG LVQPGGSLRL SCAASGFTFG SFGMSWVRQA PGKGLEWVSA IDSGGADTRY   60
AESVKGRFTI SRDNSKNTLY LQMNSLRAED TAVYYCTIGR SASRGGQGTT VTVSS        115

SEQ ID NO: 135         moltype = AA  length = 115
FEATURE                Location/Qualifiers
source                 1..115
                       mol_type = protein
                       organism = synthetic construct
SEQUENCE: 135
EVQLVESGGG LVQPGGSLRL SCAASGFTFG SFGMSWFRQA PGKEREFVSA IDSGGADTRY   60
AESVKGRFTI SRDNSKNTLY LQMNSLRAED TAVYYCTIGR SASRWGQGTT VTVSS        115

SEQ ID NO: 136         moltype = AA  length = 115
FEATURE                Location/Qualifiers
source                 1..115
                       mol_type = protein
                       organism = synthetic construct
SEQUENCE: 136
EVQLVESGGG LVQPGGSLRL SCAASGFTFG SFGMSWFRQA PGKEREFVSA IDSGGADTRY   60
AESVKGRFTI SRDNSKNTLY LQMNSLRAED TAVYYCTIGR SASRGGQGTT VTVSS        115

SEQ ID NO: 137         moltype = AA  length = 115
FEATURE                Location/Qualifiers
```

-continued

```
source                  1..115
                        mol_type = protein
                        organism = synthetic construct
SEQUENCE: 137
EVQLLESGGG LVQPGGSLRL SCAASGFSFG SFGMSWVRQA PGKGPEWVSA IDSGGADTRY   60
AETVKGRFTI SRDNSKNTLY LQMNSLRPED TAVYYCTIGR STSRGSQGTL VTVSS         115

SEQ ID NO: 138          moltype = AA  length = 115
FEATURE                 Location/Qualifiers
source                  1..115
                        mol_type = protein
                        organism = synthetic construct
SEQUENCE: 138
EVQLLESGGG LVQPGGSLRL SCAASGFTFG SFGMSWVRQA PGKGPEWVSA IDSGGADTRY   60
AETVKGRFTI SRDNSKNTLY LQMNSLRPED TAVYYCTIGR STSRGSQGTL VTVSS         115

SEQ ID NO: 139          moltype = AA  length = 115
FEATURE                 Location/Qualifiers
source                  1..115
                        mol_type = protein
                        organism = synthetic construct
SEQUENCE: 139
EVQLLESGGG LVQPGGSLRL SCAASGFTFS SFGMSWVRQA PGKGPEWVSA IDSGGADTRY   60
AETVKGRFTI SRDNSKNTLY LQMNSLRPED TAVYYCTIGR STSRGSQGTL VTVSS         115

SEQ ID NO: 140          moltype = AA  length = 115
FEATURE                 Location/Qualifiers
source                  1..115
                        mol_type = protein
                        organism = synthetic construct
SEQUENCE: 140
EVQLLESGGG LVQPGGSLRL SCAASGFSFG SFGMSWVRQA PGKGPEWVSA IDSGGADTRY   60
AETVKGRFTI SRDNSKNTLY LQMNSLRPED TAVYYCTIGR STSRSSQGTL VTVSS         115

SEQ ID NO: 141          moltype = AA  length = 17
FEATURE                 Location/Qualifiers
source                  1..17
                        mol_type = protein
                        organism = synthetic construct
VARIANT                 14
                        note = S or T
SEQUENCE: 141
AIDSGGADTR YAEXVKG                                                    17

SEQ ID NO: 142          moltype = AA  length = 6
FEATURE                 Location/Qualifiers
source                  1..6
                        mol_type = protein
                        organism = synthetic construct
VARIANT                 4
                        note = T or A
SEQUENCE: 142
GRSXSR                                                                6

SEQ ID NO: 143          moltype = AA  length = 346
FEATURE                 Location/Qualifiers
source                  1..346
                        mol_type = protein
                        organism = synthetic construct
SEQUENCE: 143
QVQLVESGGG LVQPGGSLRL SCAASGFTFG RFGMSWVRQA PGKGPEWVSA IDSGGADTRY   60
AESVKGRFTI SRDNAKKTLY LQMNSLKPED TAVYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG               346

SEQ ID NO: 144          moltype = AA  length = 346
FEATURE                 Location/Qualifiers
source                  1..346
                        mol_type = protein
                        organism = synthetic construct
SEQUENCE: 144
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGQ STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG               346
```

```
SEQ ID NO: 145              moltype = AA   length = 346
FEATURE                     Location/Qualifiers
source                      1..346
                            mol_type = protein
                            organism = synthetic construct
SEQUENCE: 145
QVQLQESGGG LVQPGGSLRL SCAASGFTFG SFGMSWVRQA PGKGPEWVSA IDSGGADTRY   60
AESVKGRFTI SRDNAKSTLY LQMNSLKPED TAVYYCTIGR SSSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 146              moltype = AA   length = 346
FEATURE                     Location/Qualifiers
source                      1..346
                            mol_type = protein
                            organism = synthetic construct
SEQUENCE: 146
EVQLVESGGG LVQPGGSLRL SCAASGFTFG SFGMSWVRQA PGKGPEWVSA IDSGGTDTRY   60
AESIKGRFTI SRDNAKKTLY LQMNSLKPED TAVYYCTIGQ STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 147              moltype = AA   length = 346
FEATURE                     Location/Qualifiers
source                      1..346
                            mol_type = protein
                            organism = synthetic construct
SEQUENCE: 147
QVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGQ STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 148              moltype = AA   length = 346
FEATURE                     Location/Qualifiers
source                      1..346
                            mol_type = protein
                            organism = synthetic construct
SEQUENCE: 148
EVQLVESGGG LVQSGGSLRL SCAASGFTFG SFGMSWVRQA PGKGPEWVSA IDGGGADTRY   60
AESVKGRFTI SRDNAKKTLY LQMNSLKPED TAVYYCTIGQ STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 149              moltype = AA   length = 346
FEATURE                     Location/Qualifiers
source                      1..346
                            mol_type = protein
                            organism = synthetic construct
SEQUENCE: 149
EVQLVESGGG LVQPGGSLRL SCAASGFTFG SFGMSWVRQA PGKGPEWVSA IDSSGADTRY   60
AESVKGRFTI SRDNAKKTLY LQMNSLKPED TAVYYCTIGR STSRRNQGTQ VTVASGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 150              moltype = AA   length = 346
FEATURE                     Location/Qualifiers
source                      1..346
                            mol_type = protein
                            organism = synthetic construct
SEQUENCE: 150
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346
```

-continued

```
SEQ ID NO: 151          moltype = AA   length = 346
FEATURE                 Location/Qualifiers
source                  1..346
                        mol_type = protein
                        organism = synthetic construct
SEQUENCE: 151
EVQLVESGGG LVQPGGSLRL SCAASGFTFG SFGMSWVRQA PGKGPEWVSA IDSGGADTRY   60
AESVKGRFTI SRDNAKKTLY LQMNSLKPED TAVYYCTIGR SASRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 152          moltype = AA   length = 346
FEATURE                 Location/Qualifiers
source                  1..346
                        mol_type = protein
                        organism = synthetic construct
SEQUENCE: 152
QVQLVESGGG LVQPGGSLRL SCAASGFTFG SFGMSWVRQA PGKGPEWVSA IDSGGADTRY   60
AETVKGRFTI SRDNLKKTLY LQMNSLKPED TAVYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 153          moltype = AA   length = 346
FEATURE                 Location/Qualifiers
source                  1..346
                        mol_type = protein
                        organism = synthetic construct
SEQUENCE: 153
QVQLVESGGG LVQPGGSLRL SCAASGFTFG SFGMSWVRQA PGKGPEWVSA IDSGGGDTRY   60
SDSVKGRFAI SRDNAKKTLY LQMNSLKPED TAAYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 154          moltype = AA   length = 346
FEATURE                 Location/Qualifiers
source                  1..346
                        mol_type = protein
                        organism = synthetic construct
SEQUENCE: 154
EVQLVESGGG LVQAGGSLRL SCAASGFTFG SFGMSWVRQV PGKGPEWVSA IDSGGTDTRY   60
AESIKGRFII SRDNAKKTLY LQMNSLKPED TAVYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 155          moltype = AA   length = 346
FEATURE                 Location/Qualifiers
source                  1..346
                        mol_type = protein
                        organism = synthetic construct
SEQUENCE: 155
QVQLVESGGG LVQPGGSLRL SCAASGFTFG SFGMSWVRQA PGKGPEWVSA IDSGGGDTRY   60
AESVKGRFTI SRDNAKKTLY LQMNSLKPED TAVYYCTIGR STSRVGQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 156          moltype = AA   length = 346
FEATURE                 Location/Qualifiers
source                  1..346
                        mol_type = protein
                        organism = synthetic construct
SEQUENCE: 156
QVQLQESGGG LVQPGGSLTL SCAASGFTFG SFGMSWVRQA PGKGPEWVSA IDSSGADTRY   60
ADSVKGRFTI SRDNAKKTLY LQMNSLKPED TAVYYCTIGR STSRGSQGTQ VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG             346

SEQ ID NO: 157          moltype = AA   length = 346
```

-continued

```
FEATURE                 Location/Qualifiers
source                  1..346
                        mol_type = protein
                        organism = synthetic construct
SEQUENCE: 157
EVQLVESGGG LVQPGGSLRL SCAASGFTFG SFGMSWVRQA PGKGPEWVSA IDSGGADTRY    60
AESVKGRFTI SRDNAKKTLY LQMNNLKPED TAMYYCTIGR STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 158          moltype = AA  length = 346
FEATURE                 Location/Qualifiers
source                  1..346
                        mol_type = protein
                        organism = synthetic construct
SEQUENCE: 158
QVQLQESGGG LVQPGDSLRL SCAASGFTFG SFGMSWVRQA PGREPEWVSA IDSGGADTRY    60
AESVKGRFTI SRDNAKKTLY LQMNTLKPED TAVYYCTIGR STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 159          moltype = AA  length = 346
FEATURE                 Location/Qualifiers
source                  1..346
                        mol_type = protein
                        organism = synthetic construct
SEQUENCE: 159
QVQLVESGGG LVQPGGSLRL SCAASGFTFG SFGMSWVRQA PGKGPEWVSA IDSGGTDTRY    60
AESIKGRFTI SRDNAKKTLY LQMNSLKPED TAVYYCTIGQ STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 160          moltype = AA  length = 346
FEATURE                 Location/Qualifiers
source                  1..346
                        mol_type = protein
                        organism = synthetic construct
SEQUENCE: 160
QVQLVESGGG LVQPGGSLRL SCAASGFTFG SFGMSWVRQA PGKGPEWVSA IDSGGGVTLY    60
AESVKGRFTI SRDNAKKTLY LQMNSLKSED TAVYYCTIGQ STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 161          moltype = AA  length = 346
FEATURE                 Location/Qualifiers
source                  1..346
                        mol_type = protein
                        organism = synthetic construct
SEQUENCE: 161
QVQLVESGGG LVQPGGSLRL SCAASGFTFG SFGMSWVRQA PGKGPEWVSA IDGGGADTRY    60
AESVKGRFTI SRDNAKKTLY LQMNSLKPED TAVYYCTIGG STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 162          moltype = AA  length = 346
FEATURE                 Location/Qualifiers
source                  1..346
                        mol_type = protein
                        organism = synthetic construct
SEQUENCE: 162
QVQLVESGGG LVQPGGSLRL SCAASGFSFG SFGMSWVRQA PGKGPEWVSA IDSGGADTRY    60
AETVKGRFTI SRDNAKKTLY LQMNSLKPED TAVYYCTIGR STSRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 163          moltype = AA  length = 346
FEATURE                 Location/Qualifiers
```

-continued

```
source                   1..346
                         mol_type = protein
                         organism = synthetic construct
SEQUENCE: 163
QVQLVESGGG LVQAGGSLRL SCAASGFTFG SFGMSWVRQA PGKGPEWVSA IDSGGVDTRY  60
AESVKGRFTI SRDNAKKTLY LQMNSLKPED TAVYYCTIGQ STSRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 164           moltype = AA  length = 346
FEATURE                  Location/Qualifiers
source                   1..346
                         mol_type = protein
                         organism = synthetic construct
SEQUENCE: 164
QVQLQESGGG LVQPGGSLRL SCAASGFTFG SFGMSWVRQA PGKGPEWVSA IDSSGADTRY  60
AESVKGRFTI SRDNAKKTLY LQMNSLNPDD TAVYYCTIGQ SISRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 165           moltype = AA  length = 346
FEATURE                  Location/Qualifiers
source                   1..346
                         mol_type = protein
                         organism = synthetic construct
SEQUENCE: 165
QVQLVESGGG LVQPGGSLRL SCAASGFTFG SFGMSWVRQA PGKGPEWVSA IDSSGADTIY  60
AESVKGRFTI ARDNAKKTLY LQMNSLKPED TAVYYCTIGQ SISRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 166           moltype = AA  length = 346
FEATURE                  Location/Qualifiers
source                   1..346
                         mol_type = protein
                         organism = synthetic construct
SEQUENCE: 166
EVQLVESGGG LVQSGGSLRL SCAASGFTFG SFGMSWVRQA PGKGPEWVSA VDSGGADTRY  60
AESVKGRFTI SRDNAKKTLY LQMNSLKPED TAVYYCTIGQ STTRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 167           moltype = AA  length = 346
FEATURE                  Location/Qualifiers
source                   1..346
                         mol_type = protein
                         organism = synthetic construct
SEQUENCE: 167
EVQLVESGGG LVQPGGSLRL SCAASGFTFG SFGMGWSRQA PGKGPEWVAA INSGGDTTLY  60
ADSVKGRFTI SRDNAKNTLY LEMNSLKPED TAVYYCTIGR GSSRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 168           moltype = AA  length = 346
FEATURE                  Location/Qualifiers
source                   1..346
                         mol_type = protein
                         organism = synthetic construct
SEQUENCE: 168
QVQLVESGGG LVQPGGSLRL SCAASGFTFG SFGMSWVRQA PGKGPEWVSA IDSGGADTRY  60
TESVKGRFTI SRDNAKKTLY LQMNSLKPED TAVYYCTIGR SISRGSQGTQ VTVSSGGGGS 120
DKTHTCPPCP APELLGGPSV FLFPPKPKDT LMISRTPEVT CVVVDVSHED PEVKFNWYVD 180
GVEVHNAKTK PREEQYNSTY RVVSVLTVLH QDWLNGKEYK CKVSNKALPA PIEKTISKAK 240
GQPREPQVYT LPPSRDELTK NQVSLTCLVK GFYPSDIAVE WESNGQPENN YKTTPPVLDS 300
DGSFFLYSKL TVDKSRWQQG NVFSCSVMHE ALHNHYTQKS LSLSPG                 346

SEQ ID NO: 169           moltype = AA  length = 346
FEATURE                  Location/Qualifiers
source                   1..346
```

-continued

```
                              mol_type = protein
                              organism = synthetic construct
SEQUENCE: 169
QVQLVESGGG LVQPGGSLRL SCAASGFSFG SFGMSWVRQA PGKGPEWVSA IDSGGADTRY    60
AETVKGRFTI SRDNAKKTLY LQMNSLKPED TAVYYCTIGR STTRGSQGTQ VTVSSGGGGS   120
DKTHTCPPCP APELLGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSRDELTK NQVSLTCLVK GFYPSDIAVE WESNGQPENN YKTTPPVLDS   300
DGSFFLYSKL TVDKSRWQQG NVFSCSVMHE ALHNHYTQKS LSLSPG               346

SEQ ID NO: 170            moltype = AA  length = 125
FEATURE                   Location/Qualifiers
source                    1..125
                          mol_type = protein
                          organism = synthetic construct
SEQUENCE: 170
QVQLVESGGG LVQPGGSLRL SCAASGFTFG RFGMSWVRQA PGKGPEWVSA IDSGGADTRY    60
AESVKGRFTI SRDNAKKTLY LQMNSLKPED TAVYYCTIGR STSRGSQGTQ VTVSSGGHHH   120
HHHHH                                                               125

SEQ ID NO: 171            moltype = AA  length = 125
FEATURE                   Location/Qualifiers
source                    1..125
                          mol_type = protein
                          organism = synthetic construct
SEQUENCE: 171
EVQLVESGGG LVQPGGSLRL SCAASGFTFG SFGMSWVRQA PGKGPEWVSA IDSGGADTRY    60
AESVKGRFTI SRDNAKKTLY LQMNSLKPED TAVYYCTIGQ STSRGSQGTQ VTVSSGGHHH   120
HHHHH                                                               125

SEQ ID NO: 172            moltype = AA  length = 125
FEATURE                   Location/Qualifiers
source                    1..125
                          mol_type = protein
                          organism = synthetic construct
SEQUENCE: 172
QVQLQESGGG LVQPGGSLRL SCAASGFTFG SFGMSWVRQA PGKGPEWVSA IDSGGADTRY    60
AESVKGRFTI SRDNAKSTLY LQMNSLKPED TAVYYCTIGR SSSRGSQGTQ VTVSSGGHHH   120
HHHHH                                                               125

SEQ ID NO: 173            moltype = AA  length = 125
FEATURE                   Location/Qualifiers
source                    1..125
                          mol_type = protein
                          organism = synthetic construct
SEQUENCE: 173
EVQLVESGGG LVQPGGSLRL SCAASGFTFG SFGMSWVRQA PGKGPEWVSA IDSGGTDTRY    60
AESIKGRFTI SRDNAKKTLY LQMNSLKPED TAVYYCTIGQ STSRGSQGTQ VTVSSGGHHH   120
HHHHH                                                               125

SEQ ID NO: 174            moltype = AA  length = 125
FEATURE                   Location/Qualifiers
source                    1..125
                          mol_type = protein
                          organism = synthetic construct
SEQUENCE: 174
QVQLVESGGG LVQPGGSLRL SCAASGFTFG SFGMSWVRQA PGKGPEWVSA IDSGGADTRY    60
AESVKGRFTI SRDNAKKTLY LQMNSLKPED TAVYYCTIGQ STSRGSQGTQ VTVSSGGHHH   120
HHHHH                                                               125

SEQ ID NO: 175            moltype = AA  length = 125
FEATURE                   Location/Qualifiers
source                    1..125
                          mol_type = protein
                          organism = synthetic construct
SEQUENCE: 175
EVQLVESGGG LVQSGGSLRL SCAASGFTFG SFGMSWVRQA PGKGPEWVSA IDGGGADTRY    60
AESVKGRFTI SRDNAKKTLY LQMNSLKPED TAVYYCTIGQ STSRGSQGTQ VTVSSGGHHH   120
HHHHH                                                               125

SEQ ID NO: 176            moltype = AA  length = 125
FEATURE                   Location/Qualifiers
source                    1..125
                          mol_type = protein
                          organism = synthetic construct
SEQUENCE: 176
EVQLVESGGG LVQPGGSLRL SCAASGFTFG SFGMSWVRQA PGKGPEWVSA IDSSGADTRY    60
AESVKGRFTI SRDNAKKTLY LQMNSLKPED TAVYYCTIGR STSRRNQGTQ VTVASGGHHH   120
HHHHH                                                               125
```

-continued

```
SEQ ID NO: 177            moltype = AA   length = 125
FEATURE                   Location/Qualifiers
source                    1..125
                          mol_type = protein
                          organism = synthetic construct
SEQUENCE: 177
EVQLVESGGG LVQPGGSLRL SCAASGFTFG SFGMSWVRQA PGKGPEWVSA IDSGGADTRY    60
AESVKGRFTI SRDNAKKTLY LQMNSLKPED TAVYYCTIGR STSRGSQGTQ VTVSSGGHHH   120
HHHHH                                                                125

SEQ ID NO: 178            moltype = AA   length = 125
FEATURE                   Location/Qualifiers
source                    1..125
                          mol_type = protein
                          organism = synthetic construct
SEQUENCE: 178
EVQLVESGGG LVQPGGSLRL SCAASGFTFG SFGMSWVRQA PGKGPEWVSA IDSGGADTRY    60
AESVKGRFTI SRDNAKKTLY LQMNSLKPED TAVYYCTIGR SASRGSQGTQ VTVSSGGHHH   120
HHHHH                                                                125

SEQ ID NO: 179            moltype = AA   length = 125
FEATURE                   Location/Qualifiers
source                    1..125
                          mol_type = protein
                          organism = synthetic construct
SEQUENCE: 179
QVQLVESGGG LVQPGGSLRL SCAASGFTFG SFGMSWVRQA PGKGPEWVSA IDSGGADTRY    60
AETVKGRFTI SRDNLKKTLY LQMNSLKPED TAVYYCTIGR STSRGSQGTQ VTVSSGGHHH   120
HHHHH                                                                125

SEQ ID NO: 180            moltype = AA   length = 125
FEATURE                   Location/Qualifiers
source                    1..125
                          mol_type = protein
                          organism = synthetic construct
SEQUENCE: 180
QVQLVESGGG LVQPGGSLRL SCAASGFTFG SFGMSWVRQA PGKGPEWVSA IDSGGGDTRY    60
SDSVKGRFAI SRDNAKKTLY LQMNSLKPED TAAYYCTIGR STSRGSQGTQ VTVSSGGHHH   120
HHHHH                                                                125

SEQ ID NO: 181            moltype = AA   length = 125
FEATURE                   Location/Qualifiers
source                    1..125
                          mol_type = protein
                          organism = synthetic construct
SEQUENCE: 181
EVQLVESGGG LVQAGGSLRL SCAASGFTFG SFGMSWVRQV PGKGPEWVSA IDSGGTDTRY    60
AESIKGRFII SRDNAKKTLY LQMNSLKPED TAVYYCTIGQ STSRGSQGTQ VTVSSGGHHH   120
HHHHH                                                                125

SEQ ID NO: 182            moltype = AA   length = 125
FEATURE                   Location/Qualifiers
source                    1..125
                          mol_type = protein
                          organism = synthetic construct
SEQUENCE: 182
QVQLVESGGG LVQPGGSLRL SCAASGFTFG SFGMSWVRQA PGKGPEWVSA IDSGGGDTRY    60
AESVKGRFTI SRDNAKKTLY LQMNSLKPED TAVYYCTIGR STSRVGQGTQ VTVSSGGHHH   120
HHHHH                                                                125

SEQ ID NO: 183            moltype = AA   length = 125
FEATURE                   Location/Qualifiers
source                    1..125
                          mol_type = protein
                          organism = synthetic construct
SEQUENCE: 183
QVQLQESGGG LVQPGGSLTL SCAASGFTFG SFGMSWVRQA PGKGPEWVSA IDSSGADTRY    60
ADSVKGRFTI SRDNAKKTLY LQMNSLKPED TAVYYCTIGR STSRGSQGTQ VTVSSGGHHH   120
HHHHH                                                                125

SEQ ID NO: 184            moltype = AA   length = 125
FEATURE                   Location/Qualifiers
source                    1..125
                          mol_type = protein
                          organism = synthetic construct
SEQUENCE: 184
EVQLVESGGG LVQPGGSLRL SCAASGFTFG SFGMSWVRQA PGKGPEWVSA IDSGGADTRY    60
AESVKGRFTI SRDNAKKTLY LQMNNLKPED TAMYYCTIGR STSRGSQGTQ VTVSSGGHHH   120
```

-continued
```
HHHHH                                                                          125

SEQ ID NO: 185            moltype = AA  length = 125
FEATURE                   Location/Qualifiers
source                    1..125
                          mol_type = protein
                          organism = synthetic construct
SEQUENCE: 185
QVQLQESGGG LVQPGDSLRL SCAASGFTFG SFGMSWVRQA PGREPEWVSA IDSGGADTRY   60
AESVKGRFTI SRDNAKKTLY LQMNTLKPED TAVYYCTIGR STSRGSQGTQ VTVSSGGHHH   120
HHHHH                                                                          125

SEQ ID NO: 186            moltype = AA  length = 125
FEATURE                   Location/Qualifiers
source                    1..125
                          mol_type = protein
                          organism = synthetic construct
SEQUENCE: 186
QVQLVESGGG LVQPGGSLRL SCAASGFTFG SFGMSWVRQA PGKGPEWVSA IDSGGTDTRY   60
AESIKGRFTI SRDNAKKTLY LQMNSLKPED TAVYYCTIGQ STSRGSQGTQ VTVSSGGHHH   120
HHHHH                                                                          125

SEQ ID NO: 187            moltype = AA  length = 125
FEATURE                   Location/Qualifiers
source                    1..125
                          mol_type = protein
                          organism = synthetic construct
SEQUENCE: 187
QVQLVESGGG LVQPGGSLRL SCAASGFTFG SFGMSWVRQA PGKGPEWVSA IDSGGGVTLY   60
AESVKGRFTI SRDNAKKTLY LQMNSLKSED TAVYYCTIGQ STSRGSQGTQ VTVSSGGHHH   120
HHHHH                                                                          125

SEQ ID NO: 188            moltype = AA  length = 125
FEATURE                   Location/Qualifiers
source                    1..125
                          mol_type = protein
                          organism = synthetic construct
SEQUENCE: 188
QVQLVESGGG LVQPGGSLRL SCAASGFTFG SFGMSWVRQA PGKGPEWVSA IDGGGADTRY   60
AESVKGRFTI SRDNAKKTLY LQMNSLKPED TAVYYCTIGG STSRGSQGTQ VTVSSGGHHH   120
HHHHH                                                                          125

SEQ ID NO: 189            moltype = AA  length = 125
FEATURE                   Location/Qualifiers
source                    1..125
                          mol_type = protein
                          organism = synthetic construct
SEQUENCE: 189
QVQLVESGGG LVQPGGSLRL SCAASGFSFG SFGMSWVRQA PGKGPEWVSA IDSGGADTRY   60
AETVKGRFTI SRDNAKKTLY LQMNSLKPED TAVYYCTIGR STSRGSQGTQ VTVSSGGHHH   120
HHHHH                                                                          125

SEQ ID NO: 190            moltype = AA  length = 125
FEATURE                   Location/Qualifiers
source                    1..125
                          mol_type = protein
                          organism = synthetic construct
SEQUENCE: 190
QVQLVESGGG LVQAGGSLRL SCAASGFTFG SFGMSWVRQA PGKGPEWVSA IDSGGVDTRY   60
AESVKGRFTI SRDNAKKTLY LQMNSLKPED TAVYYCTIGQ STSRGSQGTQ VTVSSGGHHH   120
HHHHH                                                                          125

SEQ ID NO: 191            moltype = AA  length = 125
FEATURE                   Location/Qualifiers
source                    1..125
                          mol_type = protein
                          organism = synthetic construct
SEQUENCE: 191
QVQLQESGGG LVQPGGSLRL SCAASGFTFG SFGMSWVRQA PGKGPEWVSA IDSSGADTRY   60
AESVKGRFTI SRDNAKKTLY LQMNSLNPDD TAVYYCTIGQ SISRGSQGTQ VTVSSGGHHH   120
HHHHH                                                                          125

SEQ ID NO: 192            moltype = AA  length = 125
FEATURE                   Location/Qualifiers
source                    1..125
                          mol_type = protein
                          organism = synthetic construct
SEQUENCE: 192
QVQLVESGGG LVQPGGSLRL SCAASGFTFG SFGMSWVRQA PGKGPEWVSA IDSSGADTIY   60
```

```
AESVKGRFTI ARDNAKKTLY LQMNSLKPED TAVYYCTIGQ SISRGSQGTQ VTVSSGGHHH    120
HHHHH                                                                125

SEQ ID NO: 193          moltype = AA   length = 125
FEATURE                 Location/Qualifiers
source                  1..125
                        mol_type = protein
                        organism = synthetic construct
SEQUENCE: 193
EVQLVESGGG LVQSGGSLRL SCAASGFTFG SFGMSWVRQA PGKGPEWVSA VDSGGADTRY    60
AESVKGRFTI SRDNAKKTLY LQMNSLKPED TAVYYCTIGQ STTRGSQGTQ VTVSSGGHHH    120
HHHHH                                                                125

SEQ ID NO: 194          moltype = AA   length = 125
FEATURE                 Location/Qualifiers
source                  1..125
                        mol_type = protein
                        organism = synthetic construct
SEQUENCE: 194
EVQLVESGGG LVQPGGSLRL SCAASGFTFG SFGMGWSRQA PGKGPEWVAA INSGGDTTLY    60
ADSVKGRFTI SRDNAKNTLY LEMNSLKPED TAVYYCTIGR GSSRGSQGTQ VTVSSGGHHH    120
HHHHH                                                                125

SEQ ID NO: 195          moltype = AA   length = 125
FEATURE                 Location/Qualifiers
source                  1..125
                        mol_type = protein
                        organism = synthetic construct
SEQUENCE: 195
QVQLVESGGG LVQPGGSLRL SCAASGFTFG SFGMSWVRQA PGKGPEWVSA IDSGGADTRY    60
TESVKGRFTI SRDNAKKTLY LQMNSLKPED TAVYYCTIGR SISRGSQGTQ VTVSSGGHHH    120
HHHHH                                                                125

SEQ ID NO: 196          moltype = AA   length = 125
FEATURE                 Location/Qualifiers
source                  1..125
                        mol_type = protein
                        organism = synthetic construct
SEQUENCE: 196
QVQLVESGGG LVQPGGSLRL SCAASGFSFG SFGMSWVRQA PGKGPEWVSA IDSGGADTRY    60
AETVKGRFTI SRDNAKKTLY LQMNSLKPED TAVYYCTIGR STTRGSQGTQ VTVSSGGHHH    120
HHHHH                                                                125

SEQ ID NO: 197          moltype = AA   length = 346
FEATURE                 Location/Qualifiers
source                  1..346
                        mol_type = protein
                        organism = synthetic construct
SEQUENCE: 197
EVQLLESGGG LVQPGGSLRL SCAASGFTFG SFGMSWVRQA PGKGPEWVSA IDSGGADTRY    60
AESVKGRFTI SRDNSKNTLY LQMNSLRPED TAVYYCTIGR SASRGSQGTL VTVSSGGGGS    120
DKTHTCPPCP APELLGGPSV FLFPPKPKDT LMISRTPEVT CVVVDVSHED PEVKFNWYVD    180
GVEVHNAKTK PREEQYNSTY RVVSVLTVLH QDWLNGKEYK CKVSNKALPA PIEKTISKAK    240
GQPREPQVYT LPPSRDELTK NQVSLTCLVK GFYPSDIAVE WESNGQPENN YKTTPPVLDS    300
DGSFFLYSKL TVDKSRWQQG NVFSCSVMHE ALHNHYTQKS LSLSPG                   346

SEQ ID NO: 198          moltype = AA   length = 346
FEATURE                 Location/Qualifiers
source                  1..346
                        mol_type = protein
                        organism = synthetic construct
SEQUENCE: 198
EVQLLESGGG LVQPGGSLRL SCAASGFTFS SFGMSWVRQA PGKGPEWVSA IDSGGADTRY    60
AESVKGRFTI SRDNSKNTLY LQMNSLRPED TAVYYCTIGR SASRGSQGTL VTVSSGGGGS    120
DKTHTCPPCP APELLGGPSV FLFPPKPKDT LMISRTPEVT CVVVDVSHED PEVKFNWYVD    180
GVEVHNAKTK PREEQYNSTY RVVSVLTVLH QDWLNGKEYK CKVSNKALPA PIEKTISKAK    240
GQPREPQVYT LPPSRDELTK NQVSLTCLVK GFYPSDIAVE WESNGQPENN YKTTPPVLDS    300
DGSFFLYSKL TVDKSRWQQG NVFSCSVMHE ALHNHYTQKS LSLSPG                   346

SEQ ID NO: 199          moltype = AA   length = 346
FEATURE                 Location/Qualifiers
source                  1..346
                        mol_type = protein
                        organism = synthetic construct
SEQUENCE: 199
EVQLLESGGG LVQPGGSLRL SCAASGFTFG SFGMSWVRQA PGKGPEWVSA IDSGGADTRY    60
AESVKGRFTI SRDNSKNTLY LQMNSLRPED TAVYYCTIGR SASRSSQGTL VTVSSGGGGS    120
DKTHTCPPCP APELLGGPSV FLFPPKPKDT LMISRTPEVT CVVVDVSHED PEVKFNWYVD    180
GVEVHNAKTK PREEQYNSTY RVVSVLTVLH QDWLNGKEYK CKVSNKALPA PIEKTISKAK    240
```

-continued

```
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 200           moltype = AA  length = 346
FEATURE                  Location/Qualifiers
source                   1..346
                         mol_type = protein
                         organism = synthetic construct
SEQUENCE: 200
EVQLVESGGG LVQPGGSLRL SCAASGFTFG SFGMSWVRQA PGKGLEWVSA IDSGGADTRY  60
AESVKGRFTI SRDNSKNTLY LQMNSLRAED TAVYYCTIGR SASRWGQGTT VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 201           moltype = AA  length = 346
FEATURE                  Location/Qualifiers
source                   1..346
                         mol_type = protein
                         organism = synthetic construct
SEQUENCE: 201
EVQLVESGGG LVQPGGSLRL SCAASGFTFG SFGMSWVRQA PGKGLEWVSA IDSGGADTRY  60
AESVKGRFTI SRDNSKNTLY LQMNSLRAED TAVYYCTIGR SASRGGQGTT VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 202           moltype = AA  length = 346
FEATURE                  Location/Qualifiers
source                   1..346
                         mol_type = protein
                         organism = synthetic construct
SEQUENCE: 202
EVQLVESGGG LVQPGGSLRL SCAASGFTFG SFGMSWFRQA PGKEREFVSA IDSGGADTRY  60
AESVKGRFTI SRDNSKNTLY LQMNSLRAED TAVYYCTIGR SASRWGQGTT VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 203           moltype = AA  length = 346
FEATURE                  Location/Qualifiers
source                   1..346
                         mol_type = protein
                         organism = synthetic construct
SEQUENCE: 203
EVQLVESGGG LVQPGGSLRL SCAASGFTFG SFGMSWFRQA PGKEREFVSA IDSGGADTRY  60
AESVKGRFTI SRDNSKNTLY LQMNSLRAED TAVYYCTIGR SASRGGQGTT VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 204           moltype = AA  length = 346
FEATURE                  Location/Qualifiers
source                   1..346
                         mol_type = protein
                         organism = synthetic construct
SEQUENCE: 204
EVQLLESGGG LVQPGGSLRL SCAASGFSFG SFGMSWVRQA PGKGPEWVSA IDSGGADTRY  60
AETVKGRFTI SRDNSKNTLY LQMNSLRPED TAVYYCTIGR STSRGSQGTL VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 205           moltype = AA  length = 346
FEATURE                  Location/Qualifiers
source                   1..346
                         mol_type = protein
                         organism = synthetic construct
SEQUENCE: 205
EVQLLESGGG LVQPGGSLRL SCAASGFTFG SFGMSWVRQA PGKGPEWVSA IDSGGADTRY  60
AETVKGRFTI SRDNSKNTLY LQMNSLRPED TAVYYCTIGR STSRGSQGTL VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
```

```
DGSFFLYSKL TVDKSRWQQG NVFSCSVMHE ALHNHYTQKS LSLSPG                 346

SEQ ID NO: 206          moltype = AA  length = 346
FEATURE                 Location/Qualifiers
source                  1..346
                        mol_type = protein
                        organism = synthetic construct
SEQUENCE: 206
EVQLLESGGG LVQPGGSLRL SCAASGFTFS SFGMSWVRQA PGKGPEWVSA IDSGGADTRY   60
AETVKGRFTI SRDNSKNTLY LQMNSLRPED TAVYYCTIGR STSRGSQGTL VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 207          moltype = AA  length = 346
FEATURE                 Location/Qualifiers
source                  1..346
                        mol_type = protein
                        organism = synthetic construct
SEQUENCE: 207
EVQLLESGGG LVQPGGSLRL SCAASGFSFG SFGMSWVRQA PGKGPEWVSA IDSGGADTRY   60
AETVKGRFTI SRDNSKNTLY LQMNSLRPED TAVYYCTIGR STSRSSQGTL VTVSSGGGGS  120
DKTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 208          moltype = AA  length = 346
FEATURE                 Location/Qualifiers
source                  1..346
                        mol_type = protein
                        organism = synthetic construct
SEQUENCE: 208
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLVESGG  240
GLVQPGGSLR LSCAASGFTF GSFGMSWVRQ APGKGPEWVS AIDSGGADTR YAESVKGRFT  300
ISRDNAKKTL YLQMNSLKPE DTAVYYCTIG RSASRGSQGT QVTVSS                 346

SEQ ID NO: 209          moltype = AA  length = 346
FEATURE                 Location/Qualifiers
source                  1..346
                        mol_type = protein
                        organism = synthetic construct
SEQUENCE: 209
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF GSFGMSWVRQ APGKGPEWVS AIDSGGADTR YAESVKGRFT  300
ISRDNSKNTL YLQMNSLRPE DTAVYYCTIG RSASRGSQGT LVTVSS                 346

SEQ ID NO: 210          moltype = AA  length = 346
FEATURE                 Location/Qualifiers
source                  1..346
                        mol_type = protein
                        organism = synthetic construct
SEQUENCE: 210
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF SSFGMSWVRQ APGKGPEWVS AIDSGGADTR YAESVKGRFT  300
ISRDNSKNTL YLQMNSLRPE DTAVYYCTIG RSASRGSQGT LVTVSS                 346

SEQ ID NO: 211          moltype = AA  length = 346
FEATURE                 Location/Qualifiers
source                  1..346
                        mol_type = protein
                        organism = synthetic construct
SEQUENCE: 211
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF GSFGMSWVRQ APGKGPEWVS AIDSGGADTR YAESVKGRFT  300
ISRDNSKNTL YLQMNSLRPE DTAVYYCTIG RSASRSSQGT LVTVSS                 346
```

```
SEQ ID NO: 212               moltype = AA   length = 346
FEATURE                      Location/Qualifiers
source                       1..346
                             mol_type = protein
                             organism = synthetic construct
SEQUENCE: 212
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GSFGMSWVRQ APGKGLEWVS AIDSGGADTR YAESVKGRFT   300
ISRDNSKNTL YLQMNSLRAE DTAVYYCTIG RSASRWGQGT TVTVSS                  346

SEQ ID NO: 213               moltype = AA   length = 346
FEATURE                      Location/Qualifiers
source                       1..346
                             mol_type = protein
                             organism = synthetic construct
SEQUENCE: 213
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GSFGMSWVRQ APGKGLEWVS AIDSGGADTR YAESVKGRFT   300
ISRDNSKNTL YLQMNSLRAE DTAVYYCTIG RSASRGGQGT TVTVSS                  346

SEQ ID NO: 214               moltype = AA   length = 346
FEATURE                      Location/Qualifiers
source                       1..346
                             mol_type = protein
                             organism = synthetic construct
SEQUENCE: 214
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GSFGMSWFRQ APGKEREFVS AIDSGGADTR YAESVKGRFT   300
ISRDNSKNTL YLQMNSLRAE DTAVYYCTIG RSASRWGQGT TVTVSS                  346

SEQ ID NO: 215               moltype = AA   length = 346
FEATURE                      Location/Qualifiers
source                       1..346
                             mol_type = protein
                             organism = synthetic construct
SEQUENCE: 215
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLVESGG   240
GLVQPGGSLR LSCAASGFTF GSFGMSWFRQ APGKEREFVS AIDSGGADTR YAESVKGRFT   300
ISRDNSKNTL YLQMNSLRAE DTAVYYCTIG RSASRGGQGT TVTVSS                  346

SEQ ID NO: 216               moltype = AA   length = 346
FEATURE                      Location/Qualifiers
source                       1..346
                             mol_type = protein
                             organism = synthetic construct
SEQUENCE: 216
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SQVQLVESGG   240
GLVQPGGSLR LSCAASGFSF GSFGMSWVRQ APGKGPEWVS AIDSGGADTR YAETVKGRFT   300
ISRDNAKKTL YLQMNSLKPE DTAVYYCTIG RSTSRGSQGT QVTVSS                  346

SEQ ID NO: 217               moltype = AA   length = 346
FEATURE                      Location/Qualifiers
source                       1..346
                             mol_type = protein
                             organism = synthetic construct
SEQUENCE: 217
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGG SEVQLLESGG   240
GLVQPGGSLR LSCAASGFSF GSFGMSWVRQ APGKGPEWVS AIDSGGADTR YAETVKGRFT   300
ISRDNSKNTL YLQMNSLRPE DTAVYYCTIG RSTSRGSQGT LVTVSS                  346
```

```
SEQ ID NO: 218            moltype = AA   length = 346
FEATURE                   Location/Qualifiers
source                    1..346
                          mol_type = protein
                          organism = synthetic construct
SEQUENCE: 218
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF GSFGMSWVRQ APGKGPEWVS AIDSGGADTR YAETVKGRFT  300
ISRDNSKNTL YLQMNSLRPE DTAVYYCTIG RSTSRGSQGT LVTVSS            346

SEQ ID NO: 219            moltype = AA   length = 346
FEATURE                   Location/Qualifiers
source                    1..346
                          mol_type = protein
                          organism = synthetic construct
SEQUENCE: 219
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFTF SSFGMSWVRQ APGKGPEWVS AIDSGGADTR YAETVKGRFT  300
ISRDNSKNTL YLQMNSLRPE DTAVYYCTIG RSTSRGSQGT LVTVSS            346

SEQ ID NO: 220            moltype = AA   length = 346
FEATURE                   Location/Qualifiers
source                    1..346
                          mol_type = protein
                          organism = synthetic construct
SEQUENCE: 220
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SEVQLLESGG  240
GLVQPGGSLR LSCAASGFSF GSFGMSWVRQ APGKGPEWVS AIDSGGADTR YAETVKGRFT  300
ISRDNSKNTL YLQMNSLRPE DTAVYYCTIG RSTSRSSQGT LVTVSS            346

SEQ ID NO: 221            moltype = AA   length = 125
FEATURE                   Location/Qualifiers
source                    1..125
                          mol_type = protein
                          organism = synthetic construct
SEQUENCE: 221
EVQLLESGGG LVQPGGSLRL SCAASGFTFG SFGMSWVRQA PGKGPEWVSA IDSGGADTRY   60
AESVKGRFTI SRDNSKNTLY LQMNSLRPED TAVYYCTIGR SASRGSQGTL VTVSSGGHHH  120
HHHHH                                                            125

SEQ ID NO: 222            moltype = AA   length = 125
FEATURE                   Location/Qualifiers
source                    1..125
                          mol_type = protein
                          organism = synthetic construct
SEQUENCE: 222
EVQLLESGGG LVQPGGSLRL SCAASGFTFS SFGMSWVRQA PGKGPEWVSA IDSGGADTRY   60
AESVKGRFTI SRDNSKNTLY LQMNSLRPED TAVYYCTIGR SASRGSQGTL VTVSSGGHHH  120
HHHHH                                                            125

SEQ ID NO: 223            moltype = AA   length = 125
FEATURE                   Location/Qualifiers
source                    1..125
                          mol_type = protein
                          organism = synthetic construct
SEQUENCE: 223
EVQLLESGGG LVQPGGSLRL SCAASGFTFG SFGMSWVRQA PGKGPEWVSA IDSGGADTRY   60
AESVKGRFTI SRDNSKNTLY LQMNSLRPED TAVYYCTIGR SASRSSQGTL VTVSSGGHHH  120
HHHHH                                                            125

SEQ ID NO: 224            moltype = AA   length = 125
FEATURE                   Location/Qualifiers
source                    1..125
                          mol_type = protein
                          organism = synthetic construct
SEQUENCE: 224
EVQLVESGGG LVQPGGSLRL SCAASGFTFG SFGMSWVRQA PGKGLEWVSA IDSGGADTRY   60
AESVKGRFTI SRDNSKNTLY LQMNSLRAED TAVYYCTIGR SASRWGQGTT VTVSSGGHHH  120
HHHHH                                                            125
```

-continued

```
SEQ ID NO: 225          moltype = AA   length = 125
FEATURE                 Location/Qualifiers
source                  1..125
                        mol_type = protein
                        organism = synthetic construct
SEQUENCE: 225
EVQLVESGGG LVQPGGSLRL SCAASGFTFG SFGMSWVRQA PGKGLEWVSA IDSGGADTRY    60
AESVKGRFTI SRDNSKNTLY LQMNSLRAED TAVYYCTIGR SASRGGQGTT VTVSSGGHHH   120
HHHHH                                                               125

SEQ ID NO: 226          moltype = AA   length = 125
FEATURE                 Location/Qualifiers
source                  1..125
                        mol_type = protein
                        organism = synthetic construct
SEQUENCE: 226
EVQLVESGGG LVQPGGSLRL SCAASGFTFG SFGMSWFRQA PGKEREFVSA IDSGGADTRY    60
AESVKGRFTI SRDNSKNTLY LQMNSLRAED TAVYYCTIGR SASRWGQGTT VTVSSGGHHH   120
HHHHH                                                               125

SEQ ID NO: 227          moltype = AA   length = 125
FEATURE                 Location/Qualifiers
source                  1..125
                        mol_type = protein
                        organism = synthetic construct
SEQUENCE: 227
EVQLVESGGG LVQPGGSLRL SCAASGFTFG SFGMSWFRQA PGKEREFVSA IDSGGADTRY    60
AESVKGRFTI SRDNSKNTLY LQMNSLRAED TAVYYCTIGR SASRGGQGTT VTVSSGGHHH   120
HHHHH                                                               125

SEQ ID NO: 228          moltype = AA   length = 125
FEATURE                 Location/Qualifiers
source                  1..125
                        mol_type = protein
                        organism = synthetic construct
SEQUENCE: 228
EVQLLESGGG LVQPGGSLRL SCAASGFSFG SFGMSWVRQA PGKGPEWVSA IDSGGADTRY    60
AETVKGRFTI SRDNSKNTLY LQMNSLRPED TAVYYCTIGR STSRGSQGTL VTVSSGGHHH   120
HHHHH                                                               125

SEQ ID NO: 229          moltype = AA   length = 125
FEATURE                 Location/Qualifiers
source                  1..125
                        mol_type = protein
                        organism = synthetic construct
SEQUENCE: 229
EVQLLESGGG LVQPGGSLRL SCAASGFTFG SFGMSWVRQA PGKGPEWVSA IDSGGADTRY    60
AETVKGRFTI SRDNSKNTLY LQMNSLRPED TAVYYCTIGR STSRGSQGTL VTVSSGGHHH   120
HHHHH                                                               125

SEQ ID NO: 230          moltype = AA   length = 125
FEATURE                 Location/Qualifiers
source                  1..125
                        mol_type = protein
                        organism = synthetic construct
SEQUENCE: 230
EVQLLESGGG LVQPGGSLRL SCAASGFTFS SFGMSWVRQA PGKGPEWVSA IDSGGADTRY    60
AETVKGRFTI SRDNSKNTLY LQMNSLRPED TAVYYCTIGR STSRGSQGTL VTVSSGGHHH   120
HHHHH                                                               125

SEQ ID NO: 231          moltype = AA   length = 125
FEATURE                 Location/Qualifiers
source                  1..125
                        mol_type = protein
                        organism = synthetic construct
SEQUENCE: 231
EVQLLESGGG LVQPGGSLRL SCAASGFSFG SFGMSWVRQA PGKGPEWVSA IDSGGADTRY    60
AETVKGRFTI SRDNSKNTLY LQMNSLRPED TAVYYCTIGR STSRSSQGTL VTVSSGGHHH   120
HHHHH                                                               125

SEQ ID NO: 232          moltype = AA   length = 40
FEATURE                 Location/Qualifiers
source                  1..40
                        mol_type = protein
                        organism = synthetic construct
VARIANT                 5..40
                        note = GS repeats may be deleted
SEQUENCE: 232
GSGSGSGSGS GSGSGSGSGS GSGSGSGSGS GSGSGSGSGS                          40
```

-continued

```
SEQ ID NO: 233          moltype = AA  length = 60
FEATURE                 Location/Qualifiers
source                  1..60
                        mol_type = protein
                        organism = synthetic construct
VARIANT                 7..60
                        note = GGS repeats may be deleted
SEQUENCE: 233
GGSGGSGGSG GSGGSGGSGG SGGSGGSGGS GGSGGSGGSG GSGGSGGSGG SGGSGGSGGS  60

SEQ ID NO: 234          moltype = AA  length = 80
FEATURE                 Location/Qualifiers
source                  1..80
                        mol_type = protein
                        organism = synthetic construct
VARIANT                 9..80
                        note = GGGS repeats may be deleted
SEQUENCE: 234
GGGSGGGSGG GSGGGSGGGS GGGSGGGSGG GSGGGSGGGS GGGSGGGSGG GSGGGSGGGS  60
GGGSGGGSGG GSGGGSGGGS                                              80

SEQ ID NO: 235          moltype = AA  length = 100
FEATURE                 Location/Qualifiers
source                  1..100
                        mol_type = protein
                        organism = synthetic construct
VARIANT                 11..100
                        note = GGGGS repeats may be deleted
SEQUENCE: 235
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS                        100

SEQ ID NO: 236          moltype = AA  length = 20
FEATURE                 Location/Qualifiers
source                  1..20
                        mol_type = protein
                        organism = synthetic construct
VARIANT                 2..20
                        note = Residues may be deleted
SEQUENCE: 236
GGGGGGGGGG GGGGGGGGGG                                              20

SEQ ID NO: 237          moltype = AA  length = 30
FEATURE                 Location/Qualifiers
source                  1..30
                        mol_type = protein
                        organism = synthetic construct
VARIANT                 6..30
                        note = GGGGG repeats may be deleted
SEQUENCE: 237
GGGGGGGGGG GGGGGGGGGG GGGGGGGGGG                                   30

SEQ ID NO: 238          moltype = AA  length = 36
FEATURE                 Location/Qualifiers
source                  1..36
                        mol_type = protein
                        organism = synthetic construct
VARIANT                 7..36
                        note = GGSGGD repeats may be deleted
SEQUENCE: 238
GGSGGDGGSG GDGGSGGDGG SGGDGGSGGD GGSGGD                            36

SEQ ID NO: 239          moltype = AA  length = 36
FEATURE                 Location/Qualifiers
source                  1..36
                        mol_type = protein
                        organism = synthetic construct
VARIANT                 7..36
                        note = GGSGGE repeats may be deleted
SEQUENCE: 239
GGSGGEGGSG GEGGSGGEGG SGGEGGSGGE GGSGGE                            36

SEQ ID NO: 240          moltype = AA  length = 33
FEATURE                 Location/Qualifiers
source                  1..33
                        mol_type = protein
                        organism = synthetic construct
VARIANT                 12..33
```

-continued

```
                            note = GGGSGSGGGGS repeats may be deleted
SEQUENCE: 240
GGGSGSGGGG SGGGSGSGGG GSGGGSGSGG GGS                              33

SEQ ID NO: 241          moltype = AA  length = 33
FEATURE                 Location/Qualifiers
source                  1..33
                        mol_type = protein
                        organism = synthetic construct
VARIANT                 12..33
                        note = GGGGGPGGGGP repeats may be deleted
SEQUENCE: 241
GGGGGPGGGG PGGGGGPGGG GPGGGGGPGG GGP                              33

SEQ ID NO: 242          moltype = AA  length = 17
FEATURE                 Location/Qualifiers
source                  1..17
                        mol_type = protein
                        organism = synthetic construct
VARIANT                 2
                        note = I or V
VARIANT                 3
                        note = D or N
VARIANT                 4
                        note = S or G
VARIANT                 5
                        note = G or S
VARIANT                 7
                        note = A, T, V, D, or G
VARIANT                 8
                        note = D, V, or T
VARIANT                 10
                        note = R, L, or I
VARIANT                 12
                        note = A, S, or T
VARIANT                 13
                        note = E or D
VARIANT                 14
                        note = S or T
VARIANT                 15
                        note = V or I
SEQUENCE: 242
AXXXXGXXTX YXXXXKG                                                17
```

ALBUMIN BINDING PROTEINS AND METHODS OF USE

CROSS-REFERENCE TO RELATED APPLICATIONS

This application is a continuation of U.S. patent application Ser. No. 19/180,749, filed on Apr. 16, 2025, which is a continuation of International Application No. PCT/US2025/024245, filed on Apr. 11, 2025, which claims the benefit of and priority to U.S. Provisional Patent Application No. 63/633,665, filed on Apr. 12, 2024 and U.S. Provisional Patent Application No. 63/633,667, filed on Apr. 12, 2024, the disclosure of each of which is hereby incorporated by reference in its entirety for all purposes.

SEQUENCE LISTING

This application contains a Sequence Listing XML, which has been submitted electronically and is hereby incorporated by reference in its entirety. The XML copy of the Sequence Listing, created on Apr. 8, 2025, is named PRG-043WO-_SL.xml and is 258,400 bytes in size.

BACKGROUND

Efficacy and convenience of administration of therapeutics depends on many factors including serum half-life. Serum half-life ($t^{1/2}$) of biotherapeutics can be impacted by many factors including rate and completeness of clearance through cellular recycling mechanisms. Albumin is an abundant, water-soluble protein in mammalian plasma, where, among other functions, it can act as a carrier protein and a protein to stabilize extracellular fluid volume. The circulatory half-life of albumin proteins is very long, including as compared to other serum proteins. Accordingly, albumin represents a therapeutic target to leverage for extension of half-lives of molecules, e.g., therapeutic molecules.

SUMMARY OF THE DISCLOSURE

The present disclosure, among other things, addresses certain unmet needs in making and using biotherapeutics. Compositions of the disclosure provide and leverage albumin binding proteins to extend length of serum-half lives of therapeutic molecules. The disclosure also provides methods of making and using such albumin binding proteins and fusions thereof.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 2; (b) the CDR2 has an amino acid sequence comprising or consisting of SEQ ID NO: 57, wherein $X_{55}$ can be G, A, or S; and (c) the CDR3 has an amino acid sequence comprising or consisting of SEQ ID NO: 4.

In one aspect, the disclosure provides an albumin binding protein comprising: a VHH domain, the VHH domain comprising three complementarity determining regions (CDRs). CDR1, CDR2, and CDR3, wherein: (a) the CDR1 has an amino acid sequence comprising or consisting of SEQ ID NO: 2; (b) the CDR2 has an amino acid sequence comprising or consisting of SEQ ID NO: 3; and (c) the CDR3 has an amino acid sequence comprising or consisting of SEQ ID NO: 4.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 2; (b) the CDR2 has an amino acid sequence comprising or consisting of SEQ ID NOs: 3, 19, or 20; and (c) the CDR3 has an amino acid sequence comprising or consisting of SEQ ID NO: 4.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 2, the CDR2 has an amino acid sequence comprising or consisting of SEQ ID NO: 3, and the CDR3 has an amino acid sequence comprising or consisting of SEQ ID NO: 4; (b) the CDR1 has an amino acid sequence comprising or consisting of SEQ ID NO: 2, the CDR2 has an amino acid sequence comprising or consisting of SEQ ID NO: 19, and the CDR3 has an amino acid sequence comprising or consisting of SEQ ID NO: 4; or (c) the CDR I has an amino acid sequence comprising or consisting of SEQ ID NO: 2, the CDR2 has an amino acid sequence comprising or consisting of SEQ ID NO: 20, and the CDR3 has an amino acid sequence comprising or consisting of SEQ ID NO: 4.

In one aspect, the disclosure provides an albumin binding protein comprising: a VHH domain of SEQ ID NO: 1, the VHH domain comprising three complementarity determining regions (CDRs), CDR1, CDR2, and CDR3, wherein: (a) the CDR1 has an amino acid sequence comprising or consisting of SEQ ID NO: 2; (b) the CDR2 has an amino acid sequence comprising or consisting of SEQ ID NO: 3; and (c) the CDR3 has an amino acid sequence comprising or consisting of SEQ ID NO: 4.

In one aspect, the disclosure provides an albumin binding protein comprising: a VHH domain of any of SEQ ID NOs: 7-16, the VHH domain comprising three complementarity determining regions (CDRs), CDR1, CDR2, and CDR3, wherein: (a) the CDR1 has an amino acid sequence comprising or consisting of SEQ ID NO: 2; (b) the CDR2 comprises or consists of an amino acid sequence selected from any of SEQ ID NOs: 3, 19, or 20; and (c) the CDR3 comprises or consists of an amino acid sequence of SEQ ID NO: 4.

In one aspect, the disclosure provides an albumin binding protein comprising: (a) the VHH domain having an amino acid sequence comprising or consisting of SEQ ID NO: 7 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; (b) the VHH domain having an amino acid sequence comprising or consisting of SEQ ID NO: 8 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; (c) the VHH domain having an amino acid sequence comprising or consisting of SEQ ID NO: 9 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; (d) the VHH domain having an amino acid sequence comprising or consisting of SEQ ID NO: 10 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; (e) the VHH domain having an amino acid sequence comprising or consisting of SEQ ID NO: 11 comprises the CDR1 having an amino acid sequence comprising or consisting of SEQ ID NO: 2, the CDR2 having an amino acid sequence comprising or consisting of SEQ ID NO: 19, and the CDR3 having an amino acid sequence comprising or consisting of SEQ ID NO: 4; (f) the VHH domain having an amino acid sequence comprising or consisting of SEQ ID NO: 12 comprises the CDR1 having an amino acid sequence comprising or consisting of SEQ ID NO: 2, the CDR2 having an amino acid sequence comprising or consisting of SEQ ID NO: 20, and the CDR3 having an amino acid sequence comprising or consisting of SEQ ID NO: 4; (g) the VHH domain having an amino acid sequence comprising or consisting of SEQ ID NO: 13 comprises the CDR1 having an amino acid sequence comprising or consisting of SEQ ID NO: 2, the CDR2 having an amino acid sequence comprising or consisting of SEQ ID NO: 20, and the CDR3 having an amino acid sequence comprising or consisting of SEQ ID NO: 4; (h) the VHH domain having an amino acid sequence comprising or consisting of SEQ ID NO: 14 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; (i) the VHH domain having an amino acid sequence comprising or consisting of SEQ ID NO: 15 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4; or (j) the VHH domain having an amino acid sequence comprising or consisting of SEQ ID NO: 16 comprises the CDR1 having an amino acid sequence comprising or consisting of SEQ ID NO: 2, the CDR2 having an amino acid sequence comprising or consisting of SEQ ID NO: 3, and the CDR3 having an amino acid sequence comprising or consisting of SEQ ID NO: 4.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 2; (b) the CDR2 has an amino acid sequence comprising or consisting of SEQ ID NO: 141, wherein $X_{63}$ can be S or T; and (c) the CDR3 has an amino acid sequence comprising or consisting of SEQ ID NO: 142, wherein $X_{101}$ can be T or A.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 104; (b) the CDR2 has an amino acid sequence comprising or consisting of SEQ ID NOs: 105 or 109; and (c) the CDR3 has an amino acid sequence comprising or consisting of SEQ ID NOs: 119 or 122.

In one aspect, the disclosure provides an albumin binding protein comprising: a VHH domain, the VHH domain comprising three complementarity determining regions (CDRs), CDR1, CDR2, and CDR3, wherein: (a) the CDR1 has an amino acid sequence comprising or consisting of SEQ ID NO: 104, the CDR2 has an amino acid sequence comprising or consisting of SEQ ID NO: 105, and the CDR3 has an amino acid sequence comprising or consisting of SEQ ID NO: 122; or (b) the CDR1 has an amino acid sequence comprising or consisting of SEQ ID NO: 104, the CDR2 has an amino acid sequence comprising or consisting of SEQ ID NO: 109, and the CDR3 has an amino acid sequence comprising or consisting of SEQ ID NO: 119.

In one aspect, the disclosure provides an albumin binding protein comprising: a VHH domain of SEQ ID NO: 1, the VHH domain comprising three complementarity determining regions (CDRs), CDR1, CDR2, and CDR3, wherein: (a) the CDR1 has an amino acid sequence comprising or consisting of SEQ ID NO: 104; (b) the CDR2 has an amino acid sequence comprising or consisting of SEQ ID NO: 105; and (c) the CDR3 has an amino acid sequence comprising or consisting of SEQ ID NO: 122.

In one aspect, the disclosure provides an albumin binding protein comprising: a VHH domain of SEQ ID NO: 1, the VHH domain comprising three complementarity determining regions (CDRs), CDR1, CDR2, and CDR3, wherein: (a) the CDR1 has an amino acid sequence comprising or consisting of SEQ ID NO: 104; (b) the CDR2 has an amino acid sequence comprising or consisting of SEQ ID NO: 109; and (c) the CDR3 has an amino acid sequence comprising or consisting of SEQ ID NO: 119.

In one aspect, the disclosure provides an albumin binding protein comprising: a VHH domain of any of SEQ ID NOs: 130-140, the VHH domain comprising three complementarity determining regions (CDRs), CDR1, CDR2, and CDR3, wherein: (a) the CDR1 has an amino acid sequence comprising or consisting of SEQ ID NO: 104; (b) the CDR2 has an amino acid sequence comprising or consisting of SEQ ID NOs: 105 or 109; and (c) the CDR3 has an amino acid sequence comprising or consisting of SEQ ID NOs: 119 or 122.

In one aspect, the disclosure provides an albumin binding protein comprising: (a) the VHH domain having an amino acid sequence comprising or consisting of SEQ ID NO: 130 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (b) the VHH domain having an amino acid sequence comprising or consisting of SEQ ID NO: 131 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (c) the VHH domain having an amino acid sequence comprising or consisting of SEQ ID NO: 132 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (d) the VHH domain having an amino acid sequence comprising or consisting of SEQ ID NO: 133 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (e) the VHH domain having an amino acid sequence comprising or consisting of SEQ ID NO: 134 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (f) the VHH domain having an amino acid sequence comprising or consisting of SEQ ID NO: 135 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (g) the VHH domain having an amino acid sequence comprising or consisting of SEQ ID NO: 136 comprises the CDR1 having an amino acid sequence comprising or consisting of SEQ ID NO: 104, the CDR2 having an amino acid sequence comprising or consisting of SEQ ID NO: 105, and the CDR3 having an amino acid sequence comprising or consisting of SEQ ID NO: 122; (h) the VHH domain having an amino acid sequence comprising or consisting of SEQ ID NO: 137 comprises the CDR1 having an amino acid sequence comprising or consisting of SEQ ID NO: 104, the CDR2 having an amino acid sequence comprising or consisting of SEQ ID NO: 109, and the CDR3 having an amino acid sequence comprising or consisting of SEQ ID NO: 119; (i) the VHH domain having an amino acid sequence comprising or consisting of SEQ ID NO: 138 comprises the CDR1 having an amino acid sequence comprising or consisting of SEQ ID NO: 104, the CDR2 having an amino acid sequence comprising or consisting of SEQ ID NO: 109, and the CDR3 having an amino acid sequence comprising or consisting of SEQ ID NO: 119: (j) the VHH domain having an amino acid sequence comprising or consisting of SEQ ID NO: 139 comprises the CDR1 having an amino acid sequence comprising or consisting of SEQ ID NO: 104, the CDR2 having an amino acid sequence comprising or consisting of SEQ ID NO: 109, and the CDR3 having an amino acid sequence comprising or consisting of SEQ ID NO: 119; or (k) the VHH domain having an amino acid sequence comprising or consisting of SEQ ID NO: 140 comprises the CDR1 having an amino acid sequence comprising or consisting of SEQ ID NO: 104, the CDR2 having an amino acid sequence comprising or consisting of SEQ ID NO: 109, and the CDR3 having an amino acid sequence comprising or consisting of SEQ ID NO: 119.

In certain embodiments, the albumin binding protein further comprises at least one additional component (D2), linked to the albumin binding protein (D1) according to a formula, from N-to-C terminus, of: (a) D1-L-D2, or (b) D2-L-D1, wherein D1 comprises the albumin binding protein provided herein; D2 comprises the at least one additional component; and L comprises a linker. In some embodiments. D2 comprises a second antigen binding protein or a non-antigen binding moiety. In some embodiments, the albumin binding protein further comprises one, two, three, four or more additional antigen-binding proteins or non-antigen binding moieties, wherein each additional antigen binding protein or non-antigen binding moiety is optionally linked to D1 or another additional antigen binding protein or non-antigen binding moiety by a linker.

In some embodiments, the linker is or comprises a peptide linker. For example, in some embodiments, the linker has an amino acid sequence comprising any one of SEQ ID NOs: 58-73. In certain embodiments, the linker has an amino acid sequence comprising, consisting essentially of, or consisting of SEQ ID NO: 58.

In some embodiments, D2 comprises an antigen binding protein selected from a single chain antibody or binding fragment thereof (e.g., scFv (e.g., a bispecific scFv), e.g., a single heavy chain, a single light chain, a variable heavy-chain domain (e.g., a VHH), a variable light-chain domain, a variable NAR domain, a single chain polypeptide), an F(ab') an F(ab')2 (e.g., a bi-specific F(ab')2), an F(Ab')3 (e.g., a tri-specific F(Ab')3), an Fv, a DARPin, an Fc domain (e.g., an entire Fc, a modified Fc domain, an Fc domain with one or more substitutions relative to wild-type, an Fc fragment, etc.), a minibody, a diabody, a dAb fragment, an antibody (e.g., a monoclonal antibody), a multispecific binding protein (e.g., bispecific antibody), and combinations thereof. For example, in some embodiments, the antigen binding protein of D2 comprises a variable heavy chain domain comprising or consisting of a VHH domain. In some embodiments. D2 comprises a non-antigen binding moiety selected from a detectable tag (e.g., a His tag, a Flag tag, a fluorescent tag), and an Fc domain (e.g., an entire Fc, a modified Fc domain, an Fc domain with one or more substitutions relative to wild-type, an Fc fragment, etc.).

In some embodiments, the binding affinity of the albumin binding protein for albumin is stronger than about 10 μM, about 7.5 μM, about 5 μM, about 2.5 μM, about 1 μM, about 0.75 μM, about 0.5 μM, about 0.25 μM, about 0.1 μM, about 75 nM, about 50) nM, about 25 nM, about 10) nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, about 0.01 nM, or about 0.001 nM. In some embodiments, the binding affinity of the albumin binding protein for albumin is stronger than about 0.1 μM, about 75 nM, about 50 nM, about 25 nM, about 10 nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, or about 0.01 nM.

In some embodiments, the albumin binding protein binds to albumin with a KD of less than or equal to about $1\times10^{-6}$ M at pH 6.0 or pH 7.4 as measured by surface plasmon resonance (SPR). In certain embodiments, the albumin binding protein binds to albumin with a KD of less than or equal to about $1\times10^{-7}$ M at pH 6.0 or pH 7.4 as measured by SPR. In certain embodiments, the albumin binding protein binds to albumin with a KD of less than or equal to about $1\times10^{-8}$ M at pH 6.0 or pH 7.4 as measured by SPR. In certain embodiments, the albumin binding protein binds to albumin with a KD of less than or equal to about $1\times10^{-9}$ M at pH 6.0 or pH 7.4 as measured by SPR.

In some embodiments, the albumin binding protein has been humanized.

In certain embodiments, the binding affinity of the albumin binding protein for albumin is stronger at pH 6.0 than at pH 7.4. In certain embodiments, the binding affinity of the albumin binding protein for albumin is stronger at pH 7.4 than at pH 6.0. In certain embodiments, the binding affinity of the albumin binding protein for albumin is substantially unchanged between pH 6.0 and pH 7.4.

In one aspect, the disclosure provides an albumin binding protein comprising a VHH domain comprising an amino acid sequence selected from any of SEQ ID NOs: 7-16 and 130-140.

In one aspect, the disclosure provides an albumin binding protein comprising a VHH domain comprising an amino acid sequence selected from the group consisting of SEQ ID NOS: 7-16 and 130-140.

In one aspect, the disclosure provides an albumin binding protein having an amino acid sequence selected from the group consisting of SEQ ID NOs: 7-16 and 130-140.

In one aspect, the disclosure provides a pharmaceutical composition comprising: (a) a fusion protein comprising two domains, D1, and D2, wherein: (i) D1 comprises an albumin binding protein provided herein; and (ii) D2 comprises at least one additional component comprising an antigen binding protein or a non-antigen binding moiety; and (b) a pharmaceutically acceptable excipient.

In some embodiments, the fusion protein further comprises one, two, three, four or more additional antigen binding proteins or non-antigen binding moieties.

In some embodiments, the D1 and the D2 domains of the fusion protein are linked by a linker according to a formula, from N-to-C terminus, of: (a) D1-L-D2, or (b) D2-L-D1, wherein L is the linker.

In certain embodiments, the linker is or comprises a peptide linker. For example, in some embodiments, the linker has an amino acid sequence comprising any one of SEQ ID NOs: 58-73. In some embodiments, the linker has an amino acid sequence comprising, consisting essentially of, or consisting of SEQ ID NO: 58.

In some embodiments, D2 comprises a second antigen binding fragment selected from a single chain antibody or binding fragment thereof (e.g., scFv (e.g., a bispecific scFv), e.g., a single heavy chain, a single light chain, a variable heavy-chain domain (e.g., a VHH), a variable light-chain domain, a variable NAR domain, a single chain polypeptide), an F(ab'), an F(ab')2 (e.g., a bi-specific F(ab')2), an F(Ab')3 (e.g., a tri-specific F(Ab')3), an Fv, a DARPin, an Fc domain (e.g., an entire Fc, a modified Fc domain, an Fc domain with one or more substitutions relative to wild-type, an Fc fragment, etc.), a minibody, a diabody, a dAb fragment, an antibody (e.g., a monoclonal antibody), a multi-specific binding protein (e.g., bispecific antibody), and combinations thereof. For example, in some embodiments. D2 comprises a variable heavy chain domain comprising or consisting of a VHH domain. In some embodiments. D2 comprises a non-antigen binding moiety selected from a detectable tag (e.g., a His tag, a Flag tag, a fluorescent tag), and an Fc domain (e.g., an entire Fc, a modified Fc domain, an Fc domain with one or more substitutions relative to wild-type, an Fc fragment, etc.).

In some embodiments, a binding affinity of the albumin binding protein of D1 for albumin is stronger than about 10 µM, about 7.5 µM, about 5 µM, about 2.5 µM, about 1 µM, about 0.75 µM, about 0.5 µM, about 0.25 µM, about 0.1 µM, about 75 nM, about 50 nM, about 25 nM, about 100 nM, about 90 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, about 0.01 nM, or about 0.001 nM. In some embodiments, the binding affinity of the albumin binding protein of D1 for albumin is stronger than about 0.1 µM, about 75 nM, about 50) nM, about 25 nM, about 10 nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, or about 0.01 nM.

In certain embodiments, the albumin binding protein of D1 binds to albumin with a KD of less than or equal to about $1 \times 10^{-7}$ M at pH 6.0 or pH 7.4 as measured by SPR. In certain embodiments, the albumin binding protein of D1 binds to albumin with a KD of less than or equal to about $1 \times 10^{-8}$ M at pH 6.0 or pH 7.4 as measured by SPR. In certain embodiments, the albumin binding protein of D1 binds to albumin with a KD of less than or equal to about $1 \times 10^{-9}$ M at pH 6.0 or pH 7.4 as measured by SPR.

In some embodiments, the albumin binding protein of D1 has been humanized.

In certain embodiments, the binding affinity of the albumin binding protein of D1 for albumin is stronger at pH 6.0 than at pH 7.4. In certain embodiments, the binding affinity of the albumin binding protein of D1 for albumin is stronger at pH 7.4 than at pH 6.0. In certain embodiments, the binding affinity of the albumin binding protein of D1 for albumin is substantially unchanged between pH 6.0 and pH 7.4.

In one aspect, the disclosure provides a fusion protein comprising at least two domains according to a formula, from N-to-C terminus, of: (a) Orientation I: D1-L-D2; or (b) Orientation II: D2-L-D1, wherein D1 is the albumin binding protein provided herein; L is a linker; and D2 is an additional protein binding domain or non-antigen binding domain. In some embodiments, the albumin binding protein binds with a stronger affinity when arranged in a configuration comprising D1-L-D2 as compared to D2-L-D1 when measured by SPR. In some embodiments, the albumin binding protein binds with a stronger affinity when arranged in a configuration comprising D2-L-D1 as compared to D1-L-D2 when measured by SPR.

In some embodiments, the albumin binding affinity of the albumin binding protein in orientation I is stronger than that of the albumin binding protein in orientation II at pH 6.0 and/or pH 7.4. In some embodiments, the albumin binding affinity of the albumin binding protein in orientation I is substantially unchanged as compared to that of the albumin binding protein in orientation II at pH 6.0 and/or pH 7.4.

In one aspect, the disclosure provides a method of generating a fusion protein comprising linking an albumin binding protein (D1) as provided herein to at least one additional component (D2), wherein when D2 is linked to D1 it shows one or more improvements on measures of half-life.

In one aspect, the disclosure provides a method of increasing a half-life of a therapeutic molecule, the method comprising administering a fusion protein comprising: an albumin binding protein. (D1) as provided herein, linked to at least one additional component comprising or consisting of a therapeutic molecule. (D2), wherein a half-life of the therapeutic molecule is greater when administered as the fusion protein comprising D1 and D2 than when administered as D2 not linked to D1.

In one aspect, the disclosure provides a method of increasing a half-life of a therapeutic molecule in a subject in need thereof, the method comprising administering an effective amount of a fusion protein comprising an albumin binding protein (D1) as provided herein, linked to at least one additional component comprising or consisting of a therapeutic molecule (D2), wherein a half-life of the therapeutic molecule is greater when administered as the fusion protein comprising D1 and D2 than when administered as D2 not linked to D1.

In some embodiments, the half-life of the therapeutic molecule in the fusion protein is increased by at least about 1.05-fold, 1.1-fold, 1.15-fold, 1.2-fold, 1.25-fold, 1.3-fold, 1.35-fold. 1.4-fold, 1.45-fold, 1.50-fold, 1.55-fold, 1.6-fold, 1.65-fold, 1.7-fold, 1.75-fold, 1.8-fold, 1.85-fold, 1.9-fold, 1.95-fold, 2-fold, 2.5-fold, 3-fold, 3.5-fold, 4-fold, 4.5-fold, 5-fold, 6-fold, 7-fold. 8-fold, 9-fold, 10-fold, 15-fold, 20-fold, 25-fold, 30-fold, 40-fold, 50-fold, 75-fold, 100-fold. 200-fold, 250-fold, 300-fold, 350-fold, 400-fold, 450-fold, 500-fold, 550-fold, 600-fold, 650-fold, 700-fold, 750-fold, 1.000-fold, 1.250-fold, 1.500-fold, 1.750-fold, 2.000-fold, 2.250-fold. 2.500-fold, 2.750-fold, 3.000-fold, 3.250)-fold, 3.500-fold, 3.750-fold, 4.000-fold, 4.250-fold. 4.500-fold, 4.750-fold, 5.000-fold or greater as compared to the therapeutic molecule not in the fusion protein.

In some embodiments, the effective amount is lower when the subject is administered the fusion protein as compared to D2 not linked to D1.

In some embodiments, the frequency of administration is reduced when the subject is administered the fusion protein as compared to D2 not linked to D1.

In one aspect, the disclosure provides a method of treating a subject in need thereof, the method comprising administering an effective amount of a fusion protein comprising an albumin binding protein, D1, as provided herein linked to at least one additional component, D2, comprising or consisting of a therapeutic molecule, wherein a half-life of the therapeutic molecule is greater when administered as the fusion protein comprising D1 and D2 than when administered as D2 not linked to D1.

In one aspect, the disclosure provides a method of increasing a half-life of a therapeutic molecule, the method comprising linking an albumin binding protein, D1, as provided herein to at least one additional component, D2, comprising or consisting of a therapeutic molecule, wherein the half-life of the therapeutic molecule after the linking is greater than before the linking.

In certain embodiments, administration of the fusion protein is subcutaneous. In certain embodiments, administration of the albumin binding protein is intravenous.

In one aspect, the disclosure provides a method of treating a disease or disorder in a patient in need thereof, the method comprising subcutaneously or intravenously administering to the patient an effective amount of a pharmaceutical composition as provided herein.

In some embodiments, D1 and D2 are linked by a linker that is or comprises a peptide linker. For example, in some embodiments, the linker has an amino acid sequence comprising any one of SEQ ID NOs: 58-73. In some embodiments, the linker has an amino acid sequence comprising, consisting essentially of, or consisting of SEQ ID NO: 58.

In one aspect, the disclosure provides a polynucleotide encoding an albumin binding protein as provided herein.

In one aspect, the disclosure provides a polynucleotide encoding a fusion protein comprising, from N-to-C terminus, D1-L-D2, wherein D1 comprises or consists of an albumin binding protein as provided herein; L is a linker; and D2 is at least one additional component comprising or consisting of a therapeutic molecule or a detectable molecule.

In one aspect, the disclosure provides a polynucleotide encoding a fusion protein comprising, from N-to-C terminus, D2-L-D1, wherein D1 comprises or consists of an albumin binding protein as provided herein; L is a linker; and D2 is at least one additional component comprising or consisting of a therapeutic molecule or a detectable molecule.

In some embodiments, the linker is or comprises a peptide linker. For example, in some embodiments, the linker has an amino acid sequence comprising any one of SEQ ID NOs: 58-73. In certain embodiments, the linker has an amino acid sequence comprising, consisting essentially of, or consisting of SEQ ID NO: 58.

In some embodiments, the therapeutic molecule is selected from a single chain antibody or binding fragment thereof (e.g., scFv (e.g., a bispecific scFv), e.g., a single heavy chain, a single light chain, a variable heavy-chain domain (e.g., a VHH), a variable light-chain domain, a variable NAR domain, a single chain polypeptide), an F(ab'), an F(ab')2 (e.g., a bi-specific F(ab')2), an F(Ab')3 (e.g., a tri-specific F(Ab')3), an Fv, a DARPin, an Fc domain (e.g., an entire Fc, a modified Fc domain, an Fc domain with one or more substitutions relative to wild-type, an Fc fragment, etc.), a minibody, a diabody, a dAb fragment, a multispecific binding protein (e.g., bispecific antibody), and combinations thereof. In some embodiments, the detectable molecule is a his tag, a flag tag, a fluorescent tag, or an Fc domain (e.g., an entire Fc, a modified Fc domain, an Fc domain with one or more substitutions relative to wild-type, an Fc fragment, etc.).

In one aspect, the disclosure provides a host cell comprising a polynucleotide as provided herein.

DETAILED DESCRIPTION

Definitions

To facilitate an understanding of the present disclosure, a number of terms and phrases are defined below.

The terms "a" and "an" as used herein mean "one or more" and include the plural unless the context is inappropriate.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000-fold includes 1, 2, 3, 4, 5, 6, 7, 8, 9, 10, 11, 12, 13, 14, 15, 16, 17, 18, 19, 20-fold, etc., as well as 1.1, 1.2, 1.3, 1.4, 1.5-fold, etc., 2.1, 2.2, 2.3, 2.4, 2.5-fold, etc., and so forth.

As used herein, the terms "about," "approximately," and "comparable to," when used herein in reference to a value, refer to a value that is similar to the referenced value in the context of that referenced value. In general, those skilled in the art, familiar with the context, will appreciate the relevant degree of variance encompassed by "about." "approximately," and "comparable to" in that context. For example, in some embodiments, the terms "about," "approximately," and "comparable to" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

"Percent (%) identity" refers to the extent to which two sequences (nucleotide or amino acid) have the same residue at the same positions in an alignment. For example. "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

As used herein, unless otherwise indicated, the term "antibody" is understood to mean an intact antibody (e.g., an intact monoclonal antibody), or a fragment thereof, an antigen-binding fragment (e.g., an antigen-binding fragment of a monoclonal antibody, e.g., a VHH or nanobody), or an Fc domain (e.g., an entire Fc, a modified Fc domain, an Fc domain with one or more substitutions relative to wild-type, an Fc fragment, etc.) that has been modified, engineered, or chemically conjugated. In some embodiments, an antibody is a polypeptide whose amino acid sequence includes immunoglobulins and fragments thereof which specifically bind to a designated antigen, or fragments thereof. Antibodies in accordance with the present disclosure may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acids found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains, and may include sequence elements found in the same polypeptide chain or in different polypeptide chains. Antibodies can refer to multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region (VL) and one constant region (CL). The heavy chain consists of one variable region (VH) and at least three constant regions (CH1, CH2 and CH3). The variable regions determine the binding specificity of the antibody. Antibodies can also refer to and encompass variable regions, e.g., VHH or VNAR regions such as from heavy-chain only antibodies, including those naturally produced by certain species (e.g., camelids or sharks, respectively, etc.) and those engineered therefrom (e.g., humanized VHH proteins). Each variable region contains three hypervariable regions known as complementarity determining regions (CDRs) flanked by four relatively conserved regions known as framework regions (FRs). The term "CDR" denotes a complementarity determining region as defined by at least one manner of identification to one of skill in the art. In some embodiments. CDRs can be defined in accordance with any known numbering schemes or definitions including, e.g., Chothia (see Chothia and Lesk. J Mol Biol. 1987, 196:901-917), the Kabat (see Kabat et al., 1992, Sequences of Proteins of Immunological Interest, DIANE Publishing: 2719; see also Kabat et al., 1991, Sequences of Proteins of Immunological Interest, 5th Ed., United States Public Health Service, National Institutes of Health, Bethesda and Edelman et al. 1969, Proc. Natl. Acad. Sci. USA 63(1):78-85, as set forth in Kabat 1991 for refence to "EU index as set forth in Kabat" or "EU index of Kabat" and "position . . . according to the EU index as set forth in Kabat." and grammatical variants thereof refer to the residue numbering system based on the human IgG1 EU antibody description therein), a combination of Kabat and Chothia or modified Chothia ("AbM") (see Whitelegg & Rees, Protein Eng. 2000, 13:819-824; Whitelegg & Rees, Methods Mol Biol. 2004, 248:51-91), IMGT (see Lefranc, (1999) The Immunologist, 7, 132-136), and/or the Contact (see MacCallum et al., J. Mol. Biol. 1996, 262:732-745). The extent of the FRs and CDRs has been defined (Kabat, E. A., et al. (1991) Sequences of Proteins of Immunological Interest, Fifth Edition, U.S. Department of Health and Human Services, NIH Publication No. 91-3242; and Chothia, C, et al. (1987) J. Mol. Biol. 196:901-917). The three CDRs, referred to as CDR1, CDR2, and CDR3, contribute to the antibody binding specificity. CDR sequences provided herein are according to Kabat, but one of ordinary skill in the art will understand how to adapt such CDRs to other definitions and/or numbering schemes (e.g., Chothia, AbM, IMGT, etc.). Naturally occurring antibodies have been used as starting material for engineered antibodies, such as chimeric antibodies and humanized antibodies. Examples of antibody-based antigen-binding fragments include Fab, Fab', (Fab')2, Fv, single chain (e.g., scFv, VHH, etc.) or single-domain antibodies (sdAbs, comprising, e.g., at least one VHH domain and an Fc region), VHH-containing polypeptides (polypeptides comprising at least one VHH domain), minibodies, and diabodies, and portions and/or binding fragments of any of the foregoing. Examples of antibodies that have been modified or engineered include chimeric antibodies, humanized antibodies, antibodies of various species (e.g., camelid (llama), shark, human, cynomolgus monkey, mouse, rat, etc.), and multispecific antibodies (e.g., bispecific antibodies); such modified or engineered antibodies are also understood to encompass fragments thereof including, for example, single chain antibodies or fragments. Antibodies may be produced as fusion proteins and/or conjugated to another entity. An example of an antibody fusion protein is an antibody linked to another binding entity (e.g., another antibody fragment) or a tag (e.g., a his tag) via a linker. An example of a chemically conjugated antibody is an antibody conjugated to a toxin moiety.

The terms "variable domain" and "variable region" are used interchangeably and refer to the portions of the antibody or immunoglobulin domains that exhibit variability in their sequence and that are involved in determining the specificity and binding affinity of a particular antibody. Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three-dimensional space to form an antigen-binding surface.

As used herein, the term "VHH" or "VHH domain" or "nanobody" refers to an antigen binding protein of a heavy-chain-only single chain or single domain antibody, such as from a camelid (i.e., heavy chain only) antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprises only a partial FR1 and/or FR4, or lacks one or both of those framework regions, so long as the VHH substantially maintains antigen binding and specificity. A "single domain antibody" or "sdAb" refers to a binding protein (e.g., antibody, fragment thereof) comprising at least one monomeric domain, such as a VHH domain, devoid of a light chain, and, optionally, an Fc region. In some embodiments, an sdAb is a dimer of two polypeptides wherein each polypeptide comprises at least one VHH domain and an Fc region. In some such embodiments, the at least one VHH domain can be linked to the N-terminus of the Fc region. In certain embodiments, the at least one VHH domain can be linked to the C-terminus of the Fc region. As used herein, the terms "single domain antibody" and "sdAb" encompass polypeptides that comprise multiple tandem VHH domains, such as a polypeptide having the structure $VHH_1$-$VHH_2$-Fc or $VHH_1$-$VHH_2$-$VHH_3$-Fc, wherein the VHH domains may be the same or different and, in some embodiments, may be linked by a linker.

The terms "antigen-binding domain" as well as "antigen-binding fragment" or "antibody fragment" as used herein refers to a binding protein that can be an antibody as defined herein or portion thereof (e.g., of an antibody, e.g., of an intact antibody such as a monoclonal antibody, e.g., of a heavy chain only antibody, etc.) sufficient to bind to a given antigen. The portion of the antibody can include e.g., a fragment of an intact antibody, e.g., a heavy chain only antibody, such as, e.g., a VHH, etc. In some embodiments, if the antigen-binding domain is, for example, a fragment that is a component of a larger protein such as an intact antibody (e.g., a monoclonal antibody), and the intact antibody has a function, the domain or fragment also retains that function. In some embodiments, an antigen-binding fragment comprises the variable region of the antibody (e.g., of a monoclonal antibody, e.g., of a heavy chain only antibody, etc.).

An antigen-binding protein comprises or consists of an antigen-binding domain. In some embodiments, an antigen binding domain of a conventional antibody comprises three heavy chain CDRs and three light chain CDRs. Thus, in some embodiments, an antigen binding domain comprises a heavy chain variable region comprising CDR1-FR2-CDR2-FR3-CDR3, and any portions of FR1 and/or FR4 required to maintain binding to antigen, and a light chain variable region comprising CDR1-FR2-CDR2-FR3-CDR3, and any portions of FR1 and/or FR4 required to maintain binding to antigen. In some embodiments, an antigen-binding domain comprises a heavy chain variable region and a light chain variable region. Nonlimiting such antigen-binding domains include Fabs and scFvs. In some embodiments, an antigen-binding protein or antigen binding domain comprises or consists of a VHH domain. In some such embodiments, the binding protein or binding domain comprises three CDRs, e.g., of a VHH domain, e.g., CDR1, CDR2, and CDR3. Thus, in some embodiments, an antigen binding domain of, for example, a binding protein comprising or consisting of a VHH may comprise, e.g., CDR1-FR2-CDR2-FR3-CDR3, and any portions of FR1 and/or FR4 required to maintain binding to antigen, or, alternatively FR1-CDR1-FR2-CDR2-FR3-CDR3-FR4, and fragments and binding portions thereof.

A "non-antigen" binding domain or moiety refers to a component such as a detectable label (e.g., a flag tag, a his tag, a fluorescent tag) or another protein component (e.g., an Fc domain, e.g., an Fc or fragment thereof, a modified Fc, etc.) that itself is not intended to bind to a target (e.g., an antigen, an epitope of an antigen, e.g., a target antigen such as albumin), but can be used, for example, to detect, identify, isolate, separate an entity (e.g., an antigen binding protein or domain such as an albumin binding protein) to which the non-antigen binding domain is linked (e.g., fused, such as through a linker).

As used herein, a "target antigen" refers to an antigen that is intended to be bound by a molecule of the disclosure. For example, a target antigen for the albumin binding proteins herein is albumin (e.g., mammalian albumin, e.g., human albumin). A target antigen for a second antigen binding domain may include a target that a therapeutic molecule is designed to bind to, such that two target antigens exist in an albumin protein fusion described herein, albumin and a target of an additional component of the albumin fusion (e.g., a target of a therapeutic molecule, which molecule is linked to an albumin binding protein).

As used herein, the term "epitope" is an antigenic determinant that interacts with a specific antigen binding site in the variable region of an antibody molecule, known as the paratope, and which is comprised of the six complementary-determining regions of the antibody or the three complementary-determining regions of a single-domain antibody (VHH). A single antigen may have more than one epitope. Epitopes may be conformational or linear. A conformational epitope is comprised of spatially juxtaposed amino acids from different segments of a linear polypeptide chain. A linear epitope is comprised of adjacent amino acid residues in a polypeptide chain.

As used herein, the term "humanized," when used in reference to an antibody, refers to a form of a non-human (e.g., murine) antibody that is chimeric. A "humanized antibody" contains minimal sequences derived from non-human immunoglobulin. Typically, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having a desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the framework regions are those of a human immunoglobulin sequence although the framework regions may include one or more amino acid substitutions that improve binding affinity. In some embodiments, no more than six amino acid substitutions in the heavy chain and no more than three amino acid substitutions are used in the light chain in the framework region. The humanized antibody optionally also will comprise at least a portion of an immunoglobulin constant region (Fc), typically that of a human immunoglobulin.

As used herein, the term "isolated" (e.g., with reference to a nucleic acid molecule (polynucleotide), an amino acid molecule (polypeptide), etc.) is a molecule that is identified and separated from at least one contaminant molecule with which it is ordinarily associated in the natural source of the molecule. An isolated molecule is other than in the form or setting in which it is found in nature. For example, isolated nucleic acid molecules can be distinguished from nucleic acid molecules as they exists in natural cells.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys, etc. In some embodiments, the mammal is human. None of these terms require the supervision of medical personnel.

As used herein, the term "effective amount" or "therapeutically effective amount" may be used interchangeably and refer to the amount (e.g., of a composition, e.g., as provided herein) effective, at dosages and for periods of time necessary, to achieve a desired result, e.g., a desired beneficial result, a desired therapeutic result. An effective amount can be administered in one or more administrations, applications or dosages and is not intended to be limited to a particular formulation or administration route. A therapeutically effective amount may vary according to factors such as the type of disease (e.g., disease state, age, sex, and/or weight of the individual, and the ability of an antibody (or pharmaceutical composition thereof) to elicit a desired response in the individual. An effective amount may also be an amount for which any toxic or detrimental effects of the antibody or pharmaceutical composition thereof are outweighed by therapeutically beneficial effects.

As used herein, the term "treating" includes any effect, e.g., lessening, reducing, modulating, preventing, ameliorating or eliminating, that results in the stabilization, improvement, or prevention of a condition, disease, disorder, and the like, or ameliorating a symptom thereof. To "treat" a condition or "treatment" of a condition is an approach for obtaining beneficial or desired results, such as clinical results. Beneficial or desired results can include, but are not limited to, alleviation or amelioration of one or more symptoms or conditions; diminishment of extent of disease, disorder, or condition: stabilized (i.e., not worsening) state of disease, disorder, or condition: preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. A "therapeutic molecule" refers to a molecule that can be used to treat, as described herein.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton. PA (1975).

Albumin Binding Proteins

The disclosure provides albumin binding proteins, and methods, making and using such binding proteins. Albumin represents a target that can be leveraged to address an unmet need in the field of therapeutics. Serum albumin is a water soluble blood protein produced by the liver. It is considered the most abundant mammalian blood protein. Albumin is known to naturally function as a carrier protein in the blood, and is considered to have a very long half-life. Accordingly, and without wishing to be bound by theory, this disclosure contemplates that, in some embodiments, linking (e.g., fusing, e.g., through a linker) a therapeutic molecule to serum albumin using albumin binding VHHs provided herein represents an advance in improving half-life of therapeutics. VHHs are single antigen binding domains that originate from heavy chain antibodies of other species such as camelids and sharks. These variable domain binding fragments are small and stable and, as such, may be better positioned to penetrate tissues or physiological barriers than larger binding proteins (e.g., monoclonal antibodies).

Albumin binding proteins provided herein comprise a VHH binding domain. Such albumin proteins were discovered by immunizing llamas with human serum albumin. Resulting binding proteins were isolated, purified, and sequenced as provided and described herein (see exemplary sequences of VHH and CDR proteins at least in TABLES 1-3). A selected llama-generated albumin binding protein was subsequently humanized (see, e.g., TABLES 4-6 for exemplary amino acid sequences of exemplary humanized binding proteins).

Among other things, provided herein are albumin binding proteins comprising an antigen binding domain of a heavy chain variable region (VHH). In certain embodiments, an albumin binding protein comprises a VHH domain of SEQ ID NO: 1, and 75-101 as set forth in TABLE 1.

In some embodiments, the albumin binding protein comprises or consists of a VHH domain comprising or consisting of an amino acid sequence of SEQ ID NO: 1. In some embodiments, the albumin binding protein comprises or consists of a VHH domain comprising or consisting of an amino acid sequence of SEQ ID NO: 75. In some embodiments, the albumin binding protein comprises or consists of a VHH domain comprising or consisting of an amino acid sequence of SEQ ID NO: 76. In some embodiments, the albumin binding protein comprises or consists of a VHH domain comprising or consisting of an amino acid sequence of SEQ ID NO: 77. In some embodiments, the albumin binding protein comprises or consists of a VHH domain comprising or consisting of an amino acid sequence of SEQ ID NO: 78. In some embodiments, the albumin binding protein comprises or consists of a VHH domain comprising or consisting of an amino acid sequence of SEQ ID NO: 79. In some embodiments, the albumin binding protein comprises or consists of a VHH domain comprising or consisting of an amino acid sequence of SEQ ID NO: 80. In some embodiments, the albumin binding protein comprises or consists of a VHH domain comprising or consisting of an amino acid sequence of SEQ ID NO: 81. In some embodiments, the albumin binding protein comprises or consists of a VHH domain comprising or consisting of an amino acid sequence of SEQ ID NO: 82. In some embodiments, the albumin binding protein comprises or consists of a VHH domain comprising or consisting of an amino acid sequence of SEQ ID NO: 83. In some embodiments, the albumin binding protein comprises or consists of a VHH domain comprising or consisting of an amino acid sequence of SEQ ID NO: 84. In some embodiments, the albumin binding protein comprises or consists of a VHH domain comprising or consisting of an amino acid sequence of SEQ ID NO: 85. In some embodiments, the albumin binding protein comprises or consists of a VHH domain comprising or consisting of an amino acid sequence of SEQ ID NO: 86. In some embodiments, the albumin binding protein comprises or consists of a VHH domain comprising or consisting of an amino acid sequence of SEQ ID NO: 87. In some embodiments, the albumin binding protein comprises or consists of a VHH domain comprising or consisting of an amino acid sequence of SEQ ID NO: 88. In some embodiments, the albumin binding protein comprises or consists of a VHH domain comprising or consisting of an amino acid sequence of SEQ ID NO: 89. In some embodiments, the albumin binding protein comprises or consists of a VHH domain comprising or consisting of an amino acid sequence of SEQ ID NO: 90. In some embodiments, the albumin binding protein comprises or consists of a VHH domain comprising or consisting of an amino acid sequence of SEQ ID NO: 91. In some embodiments, the albumin binding protein comprises or consists of a VHH domain comprising or consisting of an amino acid sequence of SEQ ID NO: 92. In some embodiments, the albumin binding protein comprises or consists of a VHH domain comprising or consisting of an amino acid sequence of SEQ ID NO: 93. In some embodiments, the albumin binding protein comprises or consists of a VHH domain comprising or consisting of an amino acid sequence of SEQ ID NO: 94. In some embodiments, the albumin binding protein comprises or consists of a VHH domain comprising or consisting of an amino acid sequence of SEQ ID NO: 95. In some embodiments, the albumin binding protein comprises or consists of a VHH domain comprising or consisting of an amino acid sequence of SEQ ID NO: 96. In some embodiments, the albumin binding protein comprises or consists of a VHH domain comprising or consisting of an amino acid sequence of SEQ ID NO: 97. In some embodiments, the albumin binding protein comprises or consists of a VHH domain comprising or consisting of an amino acid sequence of SEQ ID NO: 98. In some embodiments, the albumin binding protein comprises or consists of a VHH domain comprising or consisting of an amino acid sequence of SEQ ID NO: 99. In some embodiments, the albumin binding protein comprises or consists of a VHH domain comprising or consisting of an amino acid sequence of SEQ ID NO: 100. In some embodiments, the albumin binding protein comprises or consists of a VHH domain comprising or consisting of an amino acid sequence of SEQ ID NO: 101.

In some embodiments, an albumin binding protein of the disclosure may have one or more amino acid modifications to one or more regions (e.g., CDRs. FR regions) relative to a protein comprising or consisting of the amino acid sequences disclosed in TABLE 1. For example, in some embodiments, the VHH may have one, two, three, four, five, six, seven, eight, nine, ten or more substitutions in one or more framework regions (independently or cumulatively across framework regions). For example, in some embodiments, the VHH may have one, two, three, four, five, six, seven, eight, nine, ten or more substitutions (e.g., amino acid substitutions, deletions, etc.) in one or more framework regions (independently or cumulatively across framework regions). In certain embodiments, the VHH may have no more than four, three, two, or one substitutions in one or more framework regions (independently or cumulatively). In some embodiments, the VHH may have no more than four, three, two, or one substitutions in any given framework region. In some embodiments, the VHH may have no more than four, three, two, or one substitutions across all framework regions relative to any of those disclosed in TABLE 1.

In some embodiments, the albumin binding protein comprises a heavy chain variable region (VHH) comprising a CDR1, CDR2, and CDR3, such as listed in TABLE 2 or TABLE 3.

In certain embodiments, the VHH may have no more than four, three, two, or one substitutions in one or more CDRs (independently or cumulatively). In certain embodiments, the CDRs of the VHH (CDR1, CDR2, and CDR3) have sequences that can each independently differ by at most two amino acids from the CDRs provided herein. In some embodiments, the CDRs have sequences that are identical to those of the CDRs of any VHH, except for one or two amino acid substitutions total across all three CDRs.

In certain embodiments, the VHH domain comprises (a) a CDR1 having an amino acid sequence according to SEQ ID NO: 2, (b) a CDR2 having an amino acid sequence according to SEQ ID NO: 3, and (c) a CDR3 having an amino acid sequence according to SEQ ID NO: 4.

In some embodiments, the albumin binding protein comprises a VHH domain comprising or consisting of (a) a CDR1 having an amino acid sequence comprising or consisting of SEQ ID NO: 2, (b) a CDR2 having an amino acid sequence comprising or consisting of SEQ ID NO: 3, and (c) a CDR3 having an amino acid sequence comprising or consisting of SEQ ID NO: 4.

In some embodiments, the albumin binding protein comprises a VHH domain having an amino acid sequence comprising or consisting of SEQ ID NO: 1, having three CDR sequences therein wherein: (a) CDR1 can have an amino acid sequence comprising or consisting of SEQ ID NO: 2, (b) CDR2 can have an amino acid sequence comprising or consisting of SEQ ID NOs: 3, and (c) CDR3 can have an amino acid sequence comprising or consisting of SEQ ID NOs: 4.

In certain embodiments, the disclosure provides a VHH domain comprising (a) a CDR1 comprising or consisting of an amino acid sequence represented by $X_1FGMX_5$, where $X_1$ can be R or S; and $X_5$ can be S or G; (b) a CDR2 comprising or consisting of an amino acid sequence represented by $AX_{51}X_{52}X_{53}X_{54}GX_{56}X_{57}TX_{59}YX_{61}X_{62}X_{63}X_{64}KG$, where $X_{51}$ can be I or V; $X_{52}$ can be D or N; $X_{53}$ can be S or G; $X_{54}$ can be G or S; $X_{56}$ can be A, T, V, D, or G; $X_{57}$ can be D, V, or T; $X_{59}$ can be R, L, or I; $X_{61}$ can be A, S, or T; $X_{62}$ can be E or D; $X_{63}$ can be S or T; and $X_{64}$ can be V or I (SEQ ID NO: 242); and (c) a CDR3 comprising or consisting of an amino acid sequence represented by $GX_{99}X_{100}X_{101}X_{102}R$, where $X_{99}$ can be R, G, or Q; $X_{100}$ can be S or G; $X_{101}$ can be S, T, A, or I; and $X_{102}$ can be S or T.

In certain embodiments, the VHH domain comprises (a) a CDR1 having an amino acid sequence according to SEQ ID NOs: 103, 104, or 129, (b) a CDR2 having an amino acid sequence according to any one of SEQ ID NOs: 105-118, and (c) a CDR3 having an amino acid sequence according to any one of SEQ ID NOs: 119-128.

In some embodiments, the albumin binding protein comprises a VHH domain comprising or consisting of (a) a CDR1 having an amino acid sequence comprising or consisting of SEQ ID NO: 103, 104, or 129, (b) a CDR2 having an amino acid sequence comprising or consisting of any of SEQ ID NOs: 105-118, and (c) a CDR3 having an amino acid sequence comprising or consisting any of SEQ ID NOs: 119-128.

In some embodiments, the albumin binding protein comprises a VHH domain comprising or consisting of (a) a CDR1 having an amino acid sequence of SEQ ID NO: 103, (b) a CDR2 having an amino acid sequence of SEQ ID NO: 105, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 105, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 105, and (c) a CDR3 having an amino acid sequence of SEQ ID NO: 121.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 106, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 107, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 108, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 105, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 105, and (c) a CDR3 having an amino acid sequence of SEQ ID NO: 122.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 109, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 110, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 106, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 111, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 112, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 113, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 107, and (c) a CDR3 having an amino acid sequence of SEQ ID NO: 123.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 109, and (c) a CDR3 having an amino acid sequence of SEQ ID NO: 119.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 114, and (c) a CDR3 having an amino acid sequence of SEQ ID NO: 120.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 108, and (c) a CDR3 having an amino acid sequence of SEQ ID NO: 124.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 115, and (c) a CDR3 having an amino acid sequence of SEQ ID NO: 124.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 116, and (c) a CDR3 having an amino acid sequence of SEQ ID NO: 125.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 117, and (c) a CDR3 having an amino acid sequence of SEQ ID NO: 126.

In some embodiments, the albumin binding protein comprises a VHH domain comprising or consisting of (a) a CDR1 having an amino acid sequence of SEQ ID NO: 129, (b) a CDR2 having an amino acid sequence of SEQ ID NO: 117, and (c) a CDR3 having an amino acid sequence of SEQ ID NO: 126.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 118, and (c) a CDR3 having an amino acid sequence of SEQ ID NO: 127.

In some embodiments, the albumin binding protein comprises a VHH domain comprising or consisting of (a) a CDR1 having an amino acid sequence of SEQ ID NO: 104, (b) a CDR2 having an amino acid sequence of SEQ ID NO: 109, and (c) a CDR3 having an amino acid sequence of SEQ ID NO: 128.

In some embodiments, the albumin binding protein comprises a VHH domain having an amino acid sequence comprising or consisting of any of SEQ ID NOs: 75-101, having three CDR sequences therein, wherein: (a) CDR1 can comprise or consist of an amino acid sequence represented by $X_1FGMX_5$, where $X_1$ can be R or S; and $X_5$ can be S or G; (b) CDR2 can comprise or consist of an amino acid sequence represented by $AX_{51}X_{52}X_{53}X_{54}GX_{56}X_{57}TX_{59}YX_{61}X_{62}X_{63}X_{64}KG$, where $X_{51}$ can be I or V; $X_{52}$ can be D or N; $X_{53}$ can be S or G; $X_{54}$ can be G or S; $X_{56}$ can be A, T, V, D, or G; $X_{57}$ can be D, V, or T; $X_{59}$ can be R, L, or I; $X_{61}$ can be A, S, or T; $X_{62}$ can be E or D; $X_{63}$ can be S or T; and $X_{64}$ can be V or I (SEQ ID NO: 242); and (c) CDR3 can comprise or consist of an amino acid sequence represented by $GX_{99}X_{100}X_{101}X_{102}R$, where $X_{99}$ can be R, G, or Q; $X_{100}$ can be S or G; $X_{101}$ can be S, T, A, or I; and $X_{102}$ can be S or T.

In some embodiments, the albumin binding protein comprises a VHH domain having an amino acid sequence comprising or consisting of any of SEQ ID NOs: 75-101, having three CDR sequences therein wherein: (a) CDR1 can have an amino acid sequence comprising or consisting of SEQ ID NO: 103, 104, or 129, (b) CDR2 can have an amino acid sequence comprising or consisting of any of SEQ ID NOs: 105-118, and (c) CDR3 can have an amino acid sequence comprising or consisting of any of SEQ ID NOs: 119-128.

In some embodiments, the albumin binding protein comprises a VHH domain having an amino acid sequence comprising or consisting of SEQ ID NO: 75, having three CDR sequences therein wherein: (a) CDR1 can have an amino acid sequence comprising or consisting of SEQ ID NO: 103, (b) CDR2 can have an amino acid sequence comprising or consisting of SEQ ID NO: 105, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 76, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 77, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 121.

In some embodiments, the albumin binding protein comprises a VHH domain having an amino acid sequence comprising or consisting of SEQ ID NO: 78, having three CDR sequences therein wherein: (a) CDR1 can have an amino acid sequence comprising or consisting of SEQ ID NO: 104, (b) CDR2 can have an amino acid sequence comprising or consisting of SEQ ID NO: 106, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 79, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 80, having three CDR sequences therein wherein: (a) CDR1 can have an amino acid sequence comprising or consisting of SEQ ID NO: 104, (b) CDR2 can have an amino acid sequence comprising or consisting of SEQ ID NO: 107, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 81, having three CDR sequences therein wherein: (a) CDR1 can have an amino acid sequence comprising or consisting of SEQ ID NO: 104, (b) CDR2 can have an amino acid sequence comprising or consisting of SEQ ID NO: 108, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 82, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 83, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the albumin binding protein comprises a VHH domain having an amino acid sequence comprising or consisting of SEQ ID NO: 84, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 85, having three CDR sequences therein wherein: (a) CDR1 can have an amino acid sequence comprising or consisting of SEQ ID NO: 104, (b) CDR2 can have an amino acid sequence comprising or consisting of SEQ ID NO: 110, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 86, having three CDR sequences therein wherein: (a) CDR1 can have an amino acid sequence comprising or consisting of SEQ ID NO: 104, (b) CDR2 can have an amino acid sequence comprising or consisting of SEQ ID NO: 106, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 87, having three CDR sequences therein wherein: (a) CDR1 can have an amino acid sequence comprising or consisting of SEQ ID NO: 104, (b) CDR2 can have an amino acid sequence comprising or consisting of SEQ ID NO: 111, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 88, having three CDR sequences therein wherein: (a) CDR1 can have an amino acid sequence comprising or consisting of SEQ ID NO: 104, (b) CDR2 can have an amino acid sequence comprising or consisting of SEQ ID NO: 112, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 89, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 90, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 91, having three CDR sequences therein wherein: (a) CDR1 can have an amino acid sequence comprising or consisting of SEQ ID NO: 104, (b) CDR2 can have an amino acid sequence comprising or consisting of SEQ ID NO: 106, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 92, having three CDR sequences therein wherein: (a) CDR1 can have an amino acid sequence comprising or consisting of SEQ ID NO: 104, (b) CDR2 can have an amino acid sequence comprising or consisting of SEQ ID NO: 113, and (c) CDR3 can have an amino acid sequence comprising or consisting of SEQ ID NO: 120.

In some embodiments, the albumin binding protein comprises a VHH domain having an amino acid sequence comprising or consisting of SEQ ID NO: 93, having three CDR sequences therein wherein: (a) CDR1 can have an amino acid sequence comprising or consisting of SEQ ID NO: 104, (b) CDR2 can have an amino acid sequence comprising or consisting of SEQ ID NO: 107, and (c) CDR3 can have an amino acid sequence comprising or consisting of SEQ ID NO: 123.

In some embodiments, the albumin binding protein comprises a VHH domain having an amino acid sequence comprising or consisting of SEQ ID NO: 94, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

In some embodiments, the albumin binding protein comprises a VHH domain having an amino acid sequence comprising or consisting of SEQ ID NO: 95, having three CDR sequences therein wherein: (a) CDR1 can have an amino acid sequence comprising or consisting of SEQ ID NO: 104, (b) CDR2 can have an amino acid sequence comprising or consisting of SEQ ID NO: 114, and (c) CDR3 can have an amino acid sequence comprising or consisting of SEQ ID NO:

In some embodiments, the albumin binding protein comprises a VHH domain having an amino acid sequence comprising or consisting of SEQ ID NO: 96, having three CDR sequences therein wherein: (a) CDR1 can have an amino acid sequence comprising or consisting of SEQ ID NO: 104, (b) CDR2 can have an amino acid sequence comprising or consisting of SEQ ID NO: 108, and (c) CDR3 can have an amino acid sequence comprising or consisting of SEQ ID NO: 124.

In some embodiments, the albumin binding protein comprises a VHH domain having an amino acid sequence comprising or consisting of SEQ ID NO: 97, having three CDR sequences therein wherein: (a) CDR1 can have an amino acid sequence comprising or consisting of SEQ ID NO: 104, (b) CDR2 can have an amino acid sequence comprising or consisting of SEQ ID NO: 115, and (c) CDR3 can have an amino acid sequence comprising or consisting of SEQ ID NO: 124.

In some embodiments, the albumin binding protein comprises a VHH domain having an amino acid sequence comprising or consisting of SEQ ID NO: 98, having three CDR sequences therein wherein: (a) CDR1 can have an amino acid sequence comprising or consisting of SEQ ID NO: 104, (b) CDR2 can have an amino acid sequence comprising or consisting of SEQ ID NO: 116, and (c) CDR3 can have an amino acid sequence comprising or consisting of SEQ ID NO: 125.

In some embodiments, the albumin binding protein comprises a VHH domain having an amino acid sequence comprising or consisting of SEQ ID NO: 99, having three CDR sequences therein wherein: (a) CDR1 can have an amino acid sequence comprising or consisting of SEQ ID NO: 129, (b) CDR2 can have an amino acid sequence comprising or consisting of SEQ ID NO: 117, and (c) CDR3 can have an amino acid sequence comprising or consisting of SEQ ID NO: 126.

In some embodiments, the albumin binding protein comprises a VHH domain having an amino acid sequence comprising or consisting of SEQ ID NO: 100, having three CDR sequences therein wherein: (a) CDR1 can have an amino acid sequence comprising or consisting of SEQ ID NO: 104, (b) CDR2 can have an amino acid sequence comprising or consisting of SEQ ID NO: 118, and (c) CDR3 can have an amino acid sequence comprising or consisting of SEQ ID NO: 127.

In some embodiments, the albumin binding protein comprises a VHH domain having an amino acid sequence comprising or consisting of SEQ ID NO: 101, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 128.

An amino acid sequence of exemplary VHH domains of an exemplary albumin binding protein is provided in TABLE 1. Consensus sequences representing CDRs (according to Kabat) of exemplary VHH domains along with allowable amino acid residues therein are provided in TABLE 2. CDRs (according to Kabat) of the exemplary VHH domains are provided in TABLE 3.

TABLE 1

| Exemplary Llama VHH Albumin Binding Protein | | |
| --- | --- | --- |
| Albumin Binding Protein | SEQ ID NO: | Amino Acid Sequence |
| VHH-1 | 1 | QVQLVESGGGLVQPGGSLRLSCAASGFTFGQFGMSWVRQAPAKGPE RVSAISSDGSGTIYADSVKGRFTISRDNAKNTLYLQMNSLKPEDTA VYYCTIGSSTTPSGPGQGTQVTVSS |
| VHH 2 | 75 | QVQLVESGGGLVQPGGSLRLSCAASGFTFGRFGMSWVRQAPGKGPE WVSAIDSGGADTRYAESVKGRFTISRDNAKKTLYLQMNSLKPEDTA VYYCTIGRSTSRGSQGTQVTVSS |
| VHH 3 | 76 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGQSTSRGSQGTQVTVSS |
| VHH 4 | 77 | QVQLQESGGGLVQPGGSLRLSCAASGFTFGSFGMSWVRQAPGKGPE WVSAIDSGGADTRYAESVKGRFTISRDNAKSTLYLQMNSLKPEDTA VYYCTIGRSSSRGSQGTQVTVSS |
| VHH 5 | 78 | EVQLVESGGGLVQPGGSLRLSCAASGFTFGSFGMSWVRQAPGKGPE WVSAIDSGGTDTRYAESIKGRFTISRDNAKKTLYLQMNSLKPEDTA VYYCTIGQSTSRGSQGTQVTVSS |
| VHH 6 | 79 | QVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGQSTSRGSQGTQVTVSS |
| VHH 7 | 80 | EVQLVESGGGLVQSGGSLRLSCAASGFTFGSFGMSWVRQAPGKGPE WVSAIDGGGADTRYAESVKGRFTISRDNAKKTLYLQMNSLKPEDTA VYYCTIGQSTSRGSQGTQVTVSS |
| VHH 8 | 81 | EVQLVESGGGLVQPGGSLRLSCAASGFTFGSFGMSWVRQAPGKGPE WVSAIDSSGADTRYAESVKGRFTISRDNAKKTLYLQMNSLKPEDTA VYYCTIGRSTSRRNQGTQVTVAS |
| VHH 9 | 82 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGRSTSRGSQGTQVTVSS |
| VHH 10 | 83 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGRSASRGSQGTQVTVSS |
| VHH 11 | 84 | QVQLVESGGGLVQPGGSLRLSCAASGFTFGSFGMSWVRQAPGKGPE WVSAIDSGGADTRYAETVKGRFTISRDNLKKTLYLQMNSLKPEDTA VYYCTIGRSTSRGSQGTQVTVSS |
| VHH 12 | 85 | QVQLVESGGGLVQPGGSLRLSCAASGFTFGSFGMSWVRQAPGKGPE WVSAIDSGGGDTRYSDSVKGRFAISRDNAKKTLYLQMNSLKPEDTA AYYCTIGRSTSRGSQGTQVTVSS |
| VHH 13 | 86 | EVQLVESGGGLVQAGGSLRLSCAASGFTFGSFGMSWVRQVPGKGPE WVSAIDSGGTDTRYAESIKGRFIISRDNAKKTLYLQMNSLKPEDTA VYYCTIGQSTSRGSQGTQVTVSS |
| VHH 14 | 87 | QVQLVESGGGLVQPGGSLRLSCAASGFTFGSFGMSWVRQAPGKGPE WVSAIDSGGGDTRYAESVKGRFTISRDNAKKTLYLQMNSLKPEDTA VYYCTIGRSTSRVGQGTQVTVSS |
| VHH 15 | 88 | QVQLQESGGGLVQPGGSLTLSCAASGFTFGSFGMSWVRQAPGKGPE WVSAIDSSGADTRYADSVKGRFTISRDNAKKTLYLQMNSLKPEDTA VYYCTIGRSTSRGSQGTQVTVSS |

TABLE 1-continued

| Exemplary Llama VHH Albumin Binding Protein | | |
|---|---|---|
| Albumin Binding Protein | SEQ ID NO: | Amino Acid Sequence |
| VHH 16 | 89 | EVQLVESGGGLVQPGGSLRLSCAASGFTFGSFGMSWVRQAPGKGPE WVSAIDSGGADTRYAESVKGRFTISRDNAKKTLYLQMNNLKPEDTA MYYCTIGRSTSRGSQGTQVTVSS |
| VHH 17 | 90 | QVQLQESGGGLVQPGDSLRLSCAASGFTFGSFGMSWVRQAPGREPE WVSAIDSGGADTRYAESVKGRFTISRDNAKKTLYLQMNTLKPEDTA VYYCTIGRSTSRGSQGTQVTVSS |
| VHH 18 | 91 | QVQLVESGGGLVQPGGSLRLSCAASGFTFGSFGMSWVRQAPGKGPE WVSAIDSGGTDTRYAESIKGRFTISRDNAKKTLYLQMNSLKPEDTA VYYCTIGQSTSRGSQGTQVTVSS |
| VHH 19 | 92 | QVQLVESGGGLVQPGGSLRLSCAASGFTFGSFGMSWVRQAPGKGPE WVSAIDSGGGVTLYAESVKGRFTISRDNAKKTLYLQMNSLKSEDTA VYYCTIGQSTSRGSQGTQVTVSS |
| VHH 20 | 93 | QVQLVESGGGLVQPGGSLRLSCAASGFTFGSFGMSWVRQAPGKGPE WVSAIDGGGADTRYAESVKGRFTISRDNAKKTLYLQMNSLKPEDTA VYYCTIGGSTSRGSQGTQVTVSS |
| VHH 21 | 94 | QVQLVESGGGLVQPGGSLRLSCAASGFSFGSFGMSWVRQAPGKGPE WVSAIDSGGADTRYAETVKGRFTISRDNAKKTLYLQMNSLKPEDTA VYYCTIGRSTSRGSQGTQVTVSS |
| VHH 22 | 95 | QVQLVESGGGLVQAGGSLRLSCAASGFTFGSFGMSWVRQAPGKGPE WVSAIDSGGVDTRYAESVKGRFTISRDNAKKTLYLQMNSLKPEDTA VYYCTIGQSTSRGSQGTQVTVSS |
| VHH 23 | 96 | QVQLQESGGGLVQPGGSLRLSCAASGFTFGSFGMSWVRQAPGKGPE WVSAIDSSGADTRYAESVKGRFTISRDNAKKTLYLQMNSLNPDDTA VYYCTIGQSISRGSQGTQVTVSS |
| VHH 24 | 97 | QVQLVESGGGLVQPGGSLRLSCAASGFTFGSFGMSWVRQAPGKGPE WVSAIDSSGADTIYAESVKGRFTIARDNAKKTLYLQMNSLKPEDTA VYYCTIGQSISRGSQGTQVTVSS |
| VHH 25 | 98 | EVQLVESGGGLVQSGGSLRLSCAASGFTFGSFGMSWVRQAPGKGPE WVSAVDSGGADTRYAESVKGRFTISRDNAKKTLYLQMNSLKPEDTA VYYCTIGQSTTRGSQGTQVTVSS |
| VHH 26 | 99 | EVQLVESGGGLVQPGGSLRLSCAASGFTFGSFGMGWSRQAPGKGPE WVAAINSGGDTTLYADSVKGRFTISRDNAKNTLYLEMNSLKPEDTA VYYCTIGRGSSRGSQGTQVTVSS |
| VHH 27 | 100 | QVQLVESGGGLVQPGGSLRLSCAASGFTFGSFGMSWVRQAPGKGPE WVSAIDSGGADTRYTESVKGRFTISRDNAKKTLYLQMNSLKPEDTA VYYCTIGRSISRGSQGTQVTVSS |
| VHH 28 | 101 | QVQLVESGGGLVQPGGSLRLSCAASGFSFGSFGMSWVRQAPGKGPE WVSAIDSGGADTRYAETVKGRFTISRDNAKKTLYLQMNSLKPEDTA VYYCTIGRSTTRGSQGTQVTVSS |

TABLE 2

| Consensus Sequences of Exemplary Llama VHH Kabat CDRs | | |
|---|---|---|
| CDR | Amino Acid Sequence[1] | Allowable Residues |
| Llama CDR1 | $X_1$FGMX$_5$ | $X_1$: R, S, or Q; $X_5$: S, or G |
| Llama CDR2 | A$X_{51}X_{52}X_{53}X_{54}$G$X_{56}X_{57}$T$X_{59}$YX$_{61}X_{62}X_{63}X_{64}$KG (SEQ ID NO: 102) | $X_{51}$: I or V; $X_{52}$: D, N, or S; $X_{53}$: S or G; $X_{54}$: G, S, or D; $X_{56}$: A, T, V, D, or G; $X_{57}$: D, V, or T; $X_{59}$: R, L, or I; $X_{61}$: A, S, or T; $X_{62}$: E or D; $X_{63}$: S or T; $X_{64}$: V or I |

TABLE 2-continued

Consensus Sequences of Exemplary Llama VHH Kabat CDRs

| CDR | Amino Acid Sequence[1] | Allowable Residues |
|---|---|---|
| Llama CDR3 | $GX_{99}X_{100}X_{101}X_{102}X_{103}X_{104}X_{105}$ | $X_{99}$: R, G, Q, or S; $X_{100}$: S or G; $X_{101}$: S, T, A, or I; $X_{102}$: S or T; $X_{103}$: R or P; $X_{104}$: S (SEQ ID NO: 4) or not part of Kabat CDR3 (SEQ ID NOs: 119-128); $X_{105}$: G (SEQ ID NO: 4) or not part of Kabat CDR3 (SEQ ID NOs: 119-128); |

[1]Residue numbers are based on N-to-C terminal residue positions in VHH domains with reference to those of SEQ ID NOs: 1-27.

TABLE 3

Exemplary Llama VHH CDRs

| Albumin Binding Protein | CDR1 | SEQ ID NO: | CDR2 | SEQ ID NO: | CDR3 | SEQ ID NO: |
|---|---|---|---|---|---|---|
| VHH-1 | QFGMS | 2 | AISSDGSGTIYADSVKG | 3 | GSSTTPSG | 4 |
| VHH 2 | RFGMS | 103 | AIDSGGADTRYAESVKG | 105 | GRSTSR | 119 |
| VHH 3 | SFGMS | 104 | AIDSGGADTRYAESVKG | 105 | GQSTSR | 120 |
| VHH 4 | SFGMS | 104 | AIDSGGADTRYAESVKG | 105 | GRSSSR | 121 |
| VHH 5 | SFGMS | 104 | AIDSGGTDTRYAESIKG | 106 | GQSTSR | 120 |
| VHH 6 | SFGMS | 104 | AIDSGGADTRYAESVKG | 105 | GQSTSR | 120 |
| VHH 7 | SFGMS | 104 | AIDGGGADTRYAESVKG | 107 | GQSTSR | 120 |
| VHH 8 | SFGMS | 104 | AIDSSGADTRYAESVKG | 108 | GRSTSR | 119 |
| VHH 9 | SFGMS | 104 | AIDSGGADTRYAESVKG | 105 | GRSTSR | 119 |
| VHH 10 | SFGMS | 104 | AIDSGGADTRYAESVKG | 105 | GRSASR | 122 |
| VHH 11 | SFGMS | 104 | AIDSGGADTRYAETVKG | 109 | GRSTSR | 119 |
| VHH 12 | SFGMS | 104 | AIDSGGGDTRYSDSVKG | 110 | GRSTSR | 119 |
| VHH 13 | SFGMS | 104 | AIDSGGTDTRYAESIKG | 106 | GQSTSR | 120 |
| VHH 14 | SFGMS | 104 | AIDSGGGDTRYAESVKG | 111 | GRSTSR | 119 |
| VHH 15 | SFGMS | 104 | AIDSSGADTRYADSVKG | 112 | GRSTSR | 119 |
| VHH 16 | SFGMS | 104 | AIDSGGADTRYAESVKG | 105 | GRSTSR | 119 |
| VHH 17 | SFGMS | 104 | AIDSGGADTRYAESVKG | 105 | GRSTSR | 119 |
| VHH 18 | SFGMS | 104 | AIDSGGTDTRYAESIKG | 106 | GQSTSR | 120 |
| VHH 19 | SFGMS | 104 | AIDSGGGVTLYAESVKG | 113 | GQSTSR | 120 |
| VHH 20 | SFGMS | 104 | AIDGGGADTRYAESVKG | 107 | GGSTSR | 123 |
| VHH 21 | SFGMS | 104 | AIDSGGADTRYAETVKG | 109 | GRSTSR | 119 |
| VHH 22 | SFGMS | 104 | AIDSGGVDTRYAESVKG | 114 | GQSTSR | 120 |
| VHH 23 | SFGMS | 104 | AIDSSGADTRYAESVKG | 108 | GQSISR | 124 |
| VHH 24 | SFGMS | 104 | AIDSSGADTIYAESVKG | 115 | GQSISR | 124 |
| VHH 25 | SFGMS | 104 | AVDSGGADTRYAESVKG | 116 | GQSTTR | 125 |
| VHH 26 | SFGMG | 129 | AINSGGDTTLYADSVKG | 117 | GRGSSR | 126 |
| VHH 27 | SFGMS | 104 | AIDSGGADTRYTESVKG | 118 | GRSISR | 127 |
| VHH 28 | SFGMS | 104 | AIDSGGADTRYAETVKG | 109 | GRSTTR | 128 |

Hummmization

Albumin binding proteins of the disclosure may be humanized. In some embodiments, humanization can be performed by, but not limited to, methods known to those of ordinary skill in the art. In some embodiments, humanization is performed by CDRH grafting using VH modeling. In some such embodiments, VH modeling is achieved using AlphaFold 2. As provided herein, humanized albumin binding protein VHH domains were generated using the llama-derived albumin binding protein VHH domain of TABLE 1 (SEQ ID NO: 1), having CDRs (according to Kabat) comprising consensus sequences according to those in TABLE 2 and as set forth in TABLE 3 (which discloses Kabat CDR1, CDR2, and CDR3 sequences).

Exemplary humanized VHH albumin binding proteins are set forth in TABLES 4-7. In some embodiments, humanized proteins of the present disclosure bind to human serum albumin with a stronger binding affinity than non-humanized binding proteins. Without wishing to be bound by theory, the disclosure contemplates that humanization of the sequences of TABLE 1 can, in some embodiments, confer one or more advantages including but not limited to stronger and/or more specific binding to human proteins and less immunogenicity in a human when administered for therapeutic uses.

Non-human derived (e.g., llama) albumin binding proteins can be humanized using one or more techniques for humanization. For example, albumin binding proteins having an amino acid sequence comprising or consisting of that set forth in TABLE 1 can be humanized. Humanization can be performed by suitable methods including, but not limited to, those known to a person of ordinary skill in the art. For example, in some embodiments. AlphaFold2 can be used to predict a VH model. In certain embodiments, homology can be leveraged to select a VH germline. Features taken into account for humanization can include homology and developability. For example, homology of human germline to parental sequence, especially framework regions, can be evaluated. Other considerations can include germline usage rate in existing humanized or human therapeutic monoclonal antibodies, and distribution of V region gene segments in the natural human antibody repertoire. In some embodiments, based on homology. VH germline usage rate in exemplary therapeutic monoclonal antibodies, and distributions of the VH gene in natural/endogenous human antibody repertoire, a germline can be selected for VH CDR grafting and humanization.

Exemplary humanized VHH albumin binding proteins are provided in TABLE 4. Consensus sequences of CDRs of the exemplary humanized VHH albumin binding proteins are provided in TABLE 5A and TABLE 6. CDRs of the humanized VHHs are provided in TABLES 5B and 6B.

Among other things, provided herein are humanized albumin binding proteins comprising or consisting of an antigen binding domain, which domain is, or is part of the variable region of a heavy chain only antibody (VHH). Provided herein, in certain embodiments, are albumin binding proteins comprising or consisting of a VHH domain selected from any of SEQ ID NOs: 7-16 and 130-140 as set forth in TABLE 4.

In some embodiments, the humanized albumin binding protein comprises or consists of a VHH domain comprising or consisting of an amino acid sequence of SEQ ID NO: 7. In some embodiments, the humanized albumin binding protein comprises or consists of a VHH domain comprising or consisting of an amino acid sequence of SEQ ID NO: 8. In some embodiments, the humanized albumin binding protein comprises or consists of a VHH domain comprising or consisting of an amino acid sequence of SEQ ID NO: 9. In some embodiments, the humanized albumin binding protein comprises or consists of a VHH domain comprising or consisting of an amino acid sequence of SEQ ID NO: 10. In some embodiments, the humanized albumin binding protein comprises or consists of a VHH domain comprising or consisting of an amino acid sequence of SEQ ID NO: 11. In some embodiments, the humanized albumin binding protein comprises or consists of a VHH domain comprising or consisting of an amino acid sequence of SEQ ID NO: 12. In some embodiments, the humanized albumin binding protein comprises or consists of a VHH domain comprising or consisting of an amino acid sequence of SEQ ID NO: 13. In some embodiments, the humanized albumin binding protein comprises or consists of a VHH domain comprising or consisting of an amino acid sequence of SEQ ID NO: 14. In some embodiments, the humanized albumin binding protein comprises or consists of a VHH domain comprising or consisting of an amino acid sequence of SEQ ID NO: 15. In some embodiments, the humanized albumin binding protein comprises or consists of a VHH domain comprising or consisting of an amino acid sequence of SEQ ID NO: 16. In some embodiments, the humanized albumin binding protein comprises or consists of a VHH domain comprising or consisting of an amino acid sequence of SEQ ID NO: 130. In some embodiments, the humanized albumin binding protein comprises or consists of a VHH domain comprising or consisting of an amino acid sequence of SEQ ID NO: 131. In some embodiments, the humanized albumin binding protein comprises or consists of a VHH domain comprising or consisting of an amino acid sequence of SEQ ID NO: 132. In some embodiments, the humanized albumin binding protein comprises or consists of a VHH domain comprising or consisting of an amino acid sequence of SEQ ID NO: 133. In some embodiments, the humanized albumin binding protein comprises or consists of a VHH domain comprising or consisting of an amino acid sequence of SEQ ID NO: 134. In some embodiments, the humanized albumin binding protein comprises or consists of a VHH domain comprising or consisting of an amino acid sequence of SEQ ID NO: 135. In some embodiments, the humanized albumin binding protein comprises or consists of a VHH domain comprising or consisting of an amino acid sequence of SEQ ID NO: 136. In some embodiments, the humanized albumin binding protein comprises or consists of a VHH domain comprising or consisting of an amino acid sequence of SEQ ID NO: 137. In some embodiments, the humanized albumin binding protein comprises or consists of a VHH domain comprising or consisting of an amino acid sequence of SEQ ID NO: 138. In some embodiments, the humanized albumin binding protein comprises or consists of a VHH domain comprising or consisting of an amino acid sequence of SEQ ID NO: 139. In some embodiments, the humanized albumin binding protein comprises or consists of a VHH domain comprising or consisting of an amino acid sequence of SEQ ID NO: 140.

In some embodiments, an albumin binding protein of the present disclosure may have one or more amino acid modifications to one or more regions (e.g., CDRs, FR regions) relative to a protein comprising or consisting of any of the amino acid sequences disclosed in TABLE 4. For example, in some embodiments, the VHH may have one, two, three, four, five, six, seven, eight, nine, ten or more substitutions (e.g., amino acid substitutions, deletions, etc.) in one or more framework regions (independently or cumulatively across framework regions). In certain embodiments, the VHH may have no more than four, three, two, or one substitutions in one or more framework regions (independently or cumulatively). In some embodiments, the VHH may have no more than four, three, two, or one substitutions in any given framework region. In some embodiments, the VHH may have no more than four, three, two, or one substitutions across all framework regions relative to any of those disclosed in TABLE 4. In certain embodiments, the VHH has one or more additional amino acids (e.g., relative to the amino acid sequences set forth in any one of SEQ ID NOs: 7-16 and 130-140) on its N- and/or C-terminus. For example, in some embodiments, a VHH may have a C-terminal extension comprising at least one, two, three, or four amino acids. In some embodiments, a VHH may have a N-terminal extension comprising at least one, two, three, or four amino acids.

In certain embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in any one of SEQ ID NOs: 7-16 and 130-140. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 7. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 8. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 9. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 10. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 11. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 12. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 13. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 14. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 15. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 16. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 130. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 131. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 132. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 133. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 134. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 135. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 136. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 137. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 138. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 139. In some embodiments, the humanized albumin binding protein comprises or consists of a VHH domain comprising each of a complementarity determining region 1 (CDR1), a complementarity determining region 2 (CDR2), and a complementarity determining region 3 (CDR3), as set forth in SEQ ID NO: 140.

In some embodiments, the albumin binding protein comprises a humanized heavy chain variable region (VHH) comprising a CDR1, a CDR2, and a CDR3 as listed in TABLE 5 and TABLE 6.

In certain embodiments, the disclosure provides a humanized VHH domain comprising (a) a CDR1 comprising or consisting of an amino acid sequence of SEQ ID NO: 2; (b) a CDR2 comprising or consisting of an amino acid sequence represented of SEQ ID NO: 57, where $X_{55}$ can be G, A, or S; and (c) a CDR3 comprising or consisting of an amino acid sequence of SEQ ID NO: 4.

In certain embodiments, the VHH domain of the humanized albumin binding proteins comprises (i) a CDR1 having an amino acid sequence according to SEQ ID NO: 2, (ii) a CDR2 having an amino acid sequence according to any one of SEQ ID NOs: 3, 19, or 20, and (iii) a CDR3 having an amino acid sequence according to SEQ ID NO: 4.

In some embodiments, the humanized albumin binding protein comprises a VHH domain comprising or consisting of (a) a CDR1 having an amino acid sequence comprising or consisting of SEQ ID NO: 2; (b) a CDR2 having an amino acid sequence comprising or consisting of any of SEQ ID NOs: 3, 19, or 20; and (c) a CDR3 having an amino acid sequence comprising or consisting of SEQ ID NO: 4.

In some embodiments, the humanized albumin binding protein comprises a VHH domain comprising or consisting of (a) a CDR1 having an amino acid sequence of SEQ ID NO: 2, (b) a CDR2 having an amino acid sequence of SEQ ID NO: 3, and (c) a CDR3 having an amino acid sequence of SEQ ID NO: 4.

In some embodiments, the humanized albumin binding protein comprises a VHH domain comprising or consisting of (a) a CDR1 having an amino acid sequence of SEQ ID NO: 2, (b) a CDR2 having an amino acid sequence of SEQ ID NO: 19, and (c) a CDR3 having an amino acid sequence of SEQ ID NO: 4.

In some embodiments, the humanized albumin binding protein comprises a VHH domain comprising or consisting of (a) a CDR1 having an amino acid sequence of SEQ ID NO: 2, (b) a CDR2 having an amino acid sequence of SEQ ID NO: 20, and (c) a CDR3 having an amino acid sequence of SEQ ID NO: 4.

In some embodiments, the humanized albumin binding protein comprises a VHH domain having an amino acid sequence comprising or consisting of any of SEQ ID NOs: 7-16, having three CDR sequences therein, wherein: (a) CDR1 can comprise or consist of an amino acid sequence of SEQ ID NO: 2; (b) CDR2 can comprise or consist of an amino acid sequence represented by SEQ ID NO: 57, where $X_{55}$ can be G, A, or S; and (c) CDR3 can comprise or consist of an amino acid sequence of SEQ ID NO: 4.

In some embodiments, the humanized albumin binding protein comprises a VHH domain having an amino acid sequence comprising or consisting of any of SEQ ID NOs: 7-16, having three CDR sequences therein wherein: (a) CDR1 can have an amino acid sequence comprising or consisting of SEQ ID NO: 2, (b) CDR2 can have an amino acid sequence comprising or consisting of any of SEQ ID NOs: 3, 19, or 20, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 7, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 8, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 9, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 10, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 11, having three CDR sequences therein wherein: (a) CDR1 can have an amino acid sequence comprising or consisting of SEQ ID NO: 2, (b) CDR2 can have an amino acid sequence comprising or consisting of SEQ ID NO: 19, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 12, having three CDR sequences therein wherein: (a) CDR1 can have an amino acid sequence comprising or consisting of SEQ ID NO: 2, (b) CDR2 can have an amino acid sequence comprising or consisting of SEQ ID NO: 20, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 13, having three CDR sequences therein wherein: (a) CDR1 can have an amino acid sequence comprising or consisting of SEQ ID NO: 2, (b) CDR2 can have an amino acid sequence comprising or consisting of SEQ ID NO: 20, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 14, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 15, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 16, having three CDR sequences therein wherein: (a) CDR1 can have an amino acid sequence comprising or consisting of SEQ ID NO: 2, (b) CDR2 can have an amino acid sequence comprising or consisting of SEQ ID NO: 3, and (c) CDR3 can have an amino acid sequence comprising or consisting of SEQ ID NO: 4.

In some embodiments, the humanized albumin binding protein comprises a VHH domain having an amino acid sequence comprising or consisting of SEQ ID NO: 130, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 131, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 132, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 133, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 134, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 135, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 136, having three CDR sequences therein wherein: (a) CDR1 can have an amino acid sequence comprising or consisting of SEQ ID NO: 104, (b) CDR2 can have an amino acid sequence comprising or consisting of SEQ ID NO: 105, and (c) CDR3 can have an amino acid sequence comprising or consisting of SEQ ID NO: 122.

In some embodiments, the humanized albumin binding protein comprises a VHH domain having an amino acid sequence comprising or consisting of SEQ ID NO: 137, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

In some embodiments, the humanized albumin binding protein comprises a VHH domain having an amino acid sequence comprising or consisting of SEQ ID NO: 138, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

In some embodiments, the humanized albumin binding protein comprises a VHH domain having an amino acid sequence comprising or consisting of SEQ ID NO: 139, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

In some embodiments, the humanized albumin binding protein comprises a VHH domain having an amino acid sequence comprising or consisting of SEQ ID NO: 140, having three CDR sequences therein wherein: (a) CDR1 can have an amino acid sequence comprising or consisting of SEQ ID NO: 104, (b) CDR2 can have an amino acid sequence comprising or consisting of SEQ ID NO: 109, and (c) CDR3 can have an amino acid sequence comprising or consisting of SEQ ID NO: 119.

Amino acid sequences of exemplary humanized VHH albumin binding proteins are provided in TABLE 4. Consensus sequences exemplary humanized VHH albumin binding protein CDRs along with allowable amino acid residues at a variable position therein is provided in TABLE 5A and TABLE 6. CDRs of exemplary humanized VHH binding proteins and albumin binding VHH control are provided in TABLE 5B and TABLE 7.

In some embodiments, an albumin binding protein comprises a heavy chain variable region (VHH) that comprises an amino acid sequence at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100%) identical to the VHH domain of an albumin binding protein disclosed in TABLE 1 or TABLE 4. In some embodiments, an albumin binding protein comprises a heavy chain variable region (VHH) that comprises an amino acid sequence at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100%) identical to any one of SEQ ID NOs: 7-16 or 130-140.

In some such embodiments, the CDRs of any such protein are identical to any of those set forth in TABLE 3, TABLE 5B or TABLE 7. In some embodiments, the CDRs may correspond to those in TABLE 2, TABLE 3, TABLE 5A, and TABLE 6, but according to other CDR definitions and/or numbering schemes (e.g., Chothia, IMGT, etc, as described herein). In some embodiments, an albumin binding protein comprises a heavy chain variable region (VHH) that comprises an amino acid sequence at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100%) identical to any one of (i) SEQ ID NOs: 7-16, provided that the heavy chain variable region (VHH) comprises a CDR1 of SEQ ID NO: 2, a CDR2 of one of SEQ ID NOs: 3, 19, or 20, and a CDR3 of SEQ ID NO: 4 or (ii) SEQ ID NOs: 130-140, provided that the heavy chain variable region (VHH) comprises a CDR1 of SEQ ID NO: 104, a CDR2 of either SEQ ID NOs: 105 or 109, and a CDR3 of either SEQ ID NOs: 119 or 122.

TABLE 4

| Exemplary Humanized VHH Albumin Binding Proteins | | |
| --- | --- | --- |
| Albumin Binding Protein | SEQ ID NO: | Amino Acid Sequence |
| VHH 1-1 | 7 | EVQLLESGGGLVQPGGSLRLSCAASGFTFGQFGMSWVRQA PGKGPERVSAISSDGSGTIYADSVKGRFTISRDNSKNTLY LQMNSLRPEDTAVYYCTIGSSTTPSGPGQGTLVTVSS |
| VHH 1-2 | 8 | EVQLLESGGGLVQPGGSLRLSCAASGFTFSQFGMSWVRQA PGKGPERVSAISSDGSGTIYADSVKGRFTISRDNSKNTLY LQMNSLRPEDTAVYYCTIGSSTTPSGPGQGTLVTVSS |
| VHH 1-3 | 9 | QVQLVESGGGLVQPGGSLRLSCAASGFTFGQFGMSWVRQA PAKGPERVSAISSSGSGTIYADSVKGRFTISRDNAKNTLY LQMNSLKPEDTAVYYCTIGSSTTPSGPGQGTQVTVSS |
| VHH 1-4 | 10 | QVQLVESGGGLVQPGGSLRLSCAASGFTFGQFGMSWVRQA PAKGPERVSAISSGGSGTIYADSVKGRFTISRDNAKNTLY LQMNSLKPEDTAVYYCTIGSSTTPSGPGQGTQVTVSS |
| VHH 1-5 | 11 | QVQLVESGGGLVQPGGSLRLSCAASGFTFGQFGMSWVRQA PAKGPERVSAISSDASGTIYADSVKGRFTISRDNAKNTLY LQMNSLKPEDTAVYYCTIGSSTTPSGPGQGTQVTVSS |
| VHH 1-6 | 12 | QVQLVESGGGLVQPGGSLRLSCAASGFTFGQFGMSWVRQA PAKGPERVSAISSDSSGTIYADSVKGRFTISRDNAKNTLY LQMNSLKPEDTAVYYCTIGSSTTPSGPGQGTQVTVSS |
| VHH 1-7 | 13 | EVQLVESGGGLVQPGGSLRLSCAASGFTFGQFGMSWVRQA PGKGLEWVSAISSDGSGTIYADSVKGRFTISRDNSKNTLY LQMNSLRAEDTAVYYCTIGSSTTPSGWGQGTTVTVSS |
| VHH 1-8 | 14 | EVQLVESGGGLVQPGGSLRLSCAASGFTFGQFGMSWVRQA PGKGLEWVSAISSDGSGTIYADSVKGRFTISRDNSKNTLY LQMNSLRAEDTAVYYCTIGSSTTPSGPGQGTTVTVSS |
| VHH 1-9 | 15 | EVQLVESGGGLVQPGGSLRLSCAASGFTFGQFGMSWERQA PGKEREFVSAISSDGSGTIYADSVKGRFTISRDNSKNTLY LQMNSLRAEDTAVYYCTIGSSTTPSGWGQGTTVTVSS |
| VHH 1-10 | 16 | EVQLVESGGGLVQPGGSLRLSCAASGFTFGQFGMSWERQA PGKEREFVSAISSDGSGTIYADSVKGRFTISRDNSKNTLY LQMNSLRAEDTAVYYCTIGSSTTPSGPGQGTTVTVSS |
| VHH 9-1 | 130 | EVQLLESGGGLVQPGGSLRLSCAASGFTFGSFGMSWVRQA PGKGPEWVSAIDSGGADTRYAESVKGRFTISRDNSKNTLY LQMNSLRPEDTAVYYCTIGRSASRGSQGTLVTVSS |
| VHH 9-2 | 131 | EVQLLESGGGLVQPGGSLRLSCAASGFTFSSFGMSWVRQA PGKGPEWVSAIDSGGADTRYAESVKGRFTISRDNSKNTLY LQMNSLRPEDTAVYYCTIGRSASRGSQGTLVTVSS |
| VHH 9-3 | 132 | EVQLLESGGGLVQPGGSLRLSCAASGFTFGSFGMSWVRQA PGKGPEWVSAIDSGGADTRYAESVKGRFTISRDNSKNTLY LQMNSLRPEDTAVYYCTIGRSASRSSQGTLVTVSS |
| VHH 9-4 | 133 | EVQLVESGGGLVQPGGSLRLSCAASGFTFGSFGMSWVRQA PGKGLEWVSAIDSGGADTRYAESVKGRFTISRDNSKNTLY LQMNSLRAEDTAVYYCTIGRSASRWGQGTTVTVSS |

TABLE 4-continued

| Exemplary Humanized VHH Albumin Binding Proteins | | |
|---|---|---|
| Albumin Binding Protein | SEQ ID NO: | Amino Acid Sequence |
| VHH 9-5 | 134 | EVQLVESGGGLVQPGGSLRLSCAASGFTFGSFGMSWVRQA PGKGLEWVSAIDSGGADTRYAESVKGRFTISRDNSKNTLY LQMNSLRAEDTAVYYCTIGRSASRGGQGTTVTSS |
| VHH 9-6 | 135 | EVQLVESGGGLVQPGGSLRLSCAASGFTFGSFGMSWERQA PGKEREFVSAIDSGGADTRYAESVKGRFTISRDNSKNTLY LQMNSLRAEDTAVYYCTIGRSASRWGQGTTVTSS |
| VHH 9-7 | 136 | EVQLVESGGGLVQPGGSLRLSCAASGFTFGSFGMSWERQA PGKEREFVSAIDSGGADTRYAESVKGRFTISRDNSKNTLY LQMNSLRAEDTAVYYCTIGRSASRGGQGTTVTSS |
| VHH 20-1 | 137 | EVQLLESGGGLVQPGGSLRLSCAASGFSFGSFGMSWVRQA PGKGPEWVSAIDSGGADTRYAETVKGRFTISRDNSKNTLY LQMNSLRPEDTAVYYCTIGRSTSRGSQGTLVTVSS |
| VHH 20-2 | 138 | EVQLLESGGGLVQPGGSLRLSCAASGFTFGSFGMSWVRQA PGKGPEWVSAIDSGGADTRYAETVKGRFTISRDNSKNTLY LQMNSLRPEDTAVYYCTIGRSTSRGSQGTLVTVSS |
| VHH 20-3 | 139 | EVQLLESGGGLVQPGGSLRLSCAASGFTFSSFGMSWVRQA PGKGPEWVSAIDSGGADTRYAETVKGRFTISRDNSKNTLY LQMNSLRPEDTAVYYCTIGRSTSRGSQGTLVTVSS |
| VHH 20-4 | 140 | EVQLLESGGGLVQPGGSLRLSCAASGFSFGSFGMSWVRQA PGKGPEWVSAIDSGGADTRYAETVKGRFTISRDNSKNTLY LQMNSLRPEDTAVYYCTIGRSTSRSSQGTLVTVSS |

TABLE 5A

| Consensus Sequences of Exemplary Humanized VHH Albumin Binding Protein Kabat CDRs | | | |
|---|---|---|---|
| CDR | SEQ ID NO: | Amino Acid Sequence[2] | Allowable Residues |
| Humanized CDR1 | 2 | QFGMS | None |
| Humanized CDR2 | 57 | AISSD$X_{55}$SGTIYADVKG | X55: G, A, or S |
| Humanized CDR3 | 4 | GSSTTPSG | None |

TABLE 5B

| Kabat CDRs of Exemplary Humanized VHH Albumin Binding Proteins & VHH Albumin Binding Control | | | | | | |
|---|---|---|---|---|---|---|
| Albumin Binding Protein | CDR1 | SEQ ID NO: | CDR2 | SEQ ID NO: | CDR3 | SEQ ID NO: |
| VHH 1-1 | QFGMS | 2 | AISSDGSGTIYADSVKG | 3 | GSSTTPSG | 4 |
| VHH 1-2 | QFGMS | 2 | AISSDGSGTIYADSVKG | 3 | GSSTTPSG | 4 |
| VHH 1-3 | QFGMS | 2 | AISSDGSGTIYADSVKG | 3 | GSSTTPSG | 4 |
| VHH 1-4 | QFGMS | 2 | AISSDGSGTIYADSVKG | 3 | GSSTTPSG | 4 |
| VHH 1-5 | QFGMS | 2 | AISSDASGTIYADSVKG | 19 | GSSTTPSG | 4 |
| VHH 1-6 | QFGMS | 2 | AISSDSSGTIYADSVKG | 20 | GSSTTPSG | 4 |
| VHH 1-7 | QFGMS | 2 | AISSDSSGTIYADSVKG | 20 | GSSTTPSG | 4 |
| VHH 1-8 | QFGMS | 2 | AISSDGSGTIYADSVKG | 3 | GSSTTPSG | 4 |

TABLE 5B-continued

Kabat CDRs of Exemplary Humanized VHH
Albumin Binding Proteins & VHH Albumin Binding Control

| Albumin Binding Protein | CDR1 | SEQ ID NO: | CDR2 | SEQ ID NO: | CDR3 | SEQ ID NO: |
|---|---|---|---|---|---|---|
| VHH 1-9 | QFGMS | 2 | AISSDGSGTIYADSVKG | 3 | GSSTTPSG | 4 |
| VHH 1-10 | QFGMS | 2 | AISSDGSGTIYADSVKG | 3 | GSSTTPSG | 4 |

[2]Residue numbers are based on N-to-C terminal residue positions in VHH domains with reference to those of SEQ ID NOs: 7-16.

TABLE 6

Consensus Sequences of Exemplary Humanized
VHH Albumin Binding Protein Kabat CDRs

| CDR | SEQ ID NO: | Amino Acid Sequence[3] | Allowable Residues |
|---|---|---|---|
| Humanized CDR1 | 104 | SFGMS | None |
| Humanized CDR2 | 141 | AIDSGGADTRYAEX$_{63}$VKG | X$_{63}$: S or T |
| Humanized CDR3 | 142 | GRSX$_{101}$SR | X$_{101}$: T or A |

TABLE 7

Kabat CDRs of Exemplary Humanized VHH
Albumin Binding Proteins & VHH Albumin Binding Control

| Albumin Binding Protein | CDR1 | SEQ ID NO: | CDR2 | SEQ ID NO: | CDR3 | SEQ ID NO: |
|---|---|---|---|---|---|---|
| VHH 9-1 | SFGMS | 104 | AIDSGGADTRYAESVKG | 105 | GRSASR | 122 |
| VHH 9-2 | SFGMS | 104 | AIDSGGADTRYAESVKG | 105 | GRSASR | 122 |
| VHH 9-3 | SFGMS | 104 | AIDSGGADTRYAESVKG | 105 | GRSASR | 122 |
| VHH 9-4 | SFGMS | 104 | AIDSGGADTRYAESVKG | 105 | GRSASR | 122 |
| VHH 9-5 | SFGMS | 104 | AIDSGGADTRYAESVKG | 105 | GRSASR | 122 |
| VHH 9-6 | SFGMS | 104 | AIDSGGADTRYAESVKG | 105 | GRSASR | 122 |
| VHH 9-7 | SFGMS | 104 | AIDSGGADTRYAESVKG | 105 | GRSASR | 122 |
| VHH 20-1 | SFGMS | 104 | AIDSGGADTRYAETVKG | 109 | GRSTSR | 119 |
| VHH 20-2 | SFGMS | 104 | AIDSGGADTRYAETVKG | 109 | GRSTSR | 119 |
| VHH 20-3 | SFGMS | 104 | AIDSGGADTRYAETVKG | 109 | GRSTSR | 119 |
| VHH 20-4 | SFGMS | 104 | AIDSGGADTRYAETVKG | 109 | GRSTSR | 119 |
| VHH Control | SFGMS | 18 | SISGSGSDTLYADSVKG | 21 | GGSLSR | 22 |

In some embodiments, the disclosure provides a nucleic acid molecule encoding an albumin binding protein provided herein. In some embodiments, a host cell comprises the polynucleotide encoding the albumin binding protein. Polynucleotides encoding desired albumin binding proteins can be incorporated (ligated) into expression vectors, which can be introduced into host cells through conventional transfection or transformation techniques. Exemplary host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells.

In some embodiments, an albumin binding protein of the disclosure binds to albumin with a binding affinity stronger than about 10 µM, about 7.5 µM, about 5 µM, about 2.5 µM,

[3]Residue numbers are based on N-to-C terminal residue positions in VHH domains with reference to those of SEQ ID NOs: 130-140.

about 1 µM, about 0.75 µM, about 0.5 µM, about 0.25 µM, about 0.1 µM, about 75 nM, about 50) nM, about 25 nM, about 10 nM, about 9) nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, about 0.01 nM, or about 0.001 nM.

In some embodiments, the binding affinity for albumin is stronger than about 0.1 µM, about 75 nM, about 50 nM, about 25 nM, about 10 nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, or about 0.01 nM.

In some embodiments, the albumin binding protein binds to albumin with a KD of less than or equal to about $1 \times 10^{-6}$ M, $1 \times 10^{-7}$ M, $1 \times 10^{-8}$ M, $1 \times 10^{-9}$ M, or less at pH 6.0 or pH 7.4 as measured by surface plasmon resonance (SPR).

In some embodiments, the binding affinity of the albumin binding protein for albumin is stronger at pH 6.0 than at pH 7.4. In some embodiments, the binding affinity is stronger at pH 7.4 than at pH 6.0. In some embodiments, the binding affinity is substantially unchanged at pH 6.0 as compared to pH 7.4.

In some embodiments, an albumin binding protein of the disclosure binds to serum albumin from multiple species (e.g., human, cynomolgus monkey, mouse, rat, etc.). In some embodiments, an albumin binding protein of the disclosure has been humanized and binds to human serum albumin at a greater affinity than to serum albumin from, e.g., monkey, mouse, rat, etc.

In some embodiments, the albumin binding proteins are characterized by a half-life of at least about 3, 7, 14, 21, 28, 35, 42, 49, 56, 63, 70, 77, 84, 91, 98 or more days. In some embodiments, the half-life is in a range of about 3 days to about 98 days, about 7 days to about 91 days, about 14 days to about 84 days, about 21 days to about 77 days, about 28 days to about 70 days, about 35 days to about 63 days, about 42 days to about 56 days, about 3 days to about 42 days, about 7 days to about 49 days, about 14 days to about 56 days, about 5, 10, 15, 20, 25, 30, 35, 40, 45, 50, 55, 60, or more days, etc. In some embodiments, the half-life is in a range of about 14 days to about 56 days. In some embodiments, the half-life is at least about 84 days. In some embodiments, the half-life is at least about 56 days. In some embodiments, the half life is at least about 28 days. In some embodiments, the half-life is at least about 14 days. In some embodiments, the half-life is at least about 7 days.

Methods of measuring half-life are known in the art. In some embodiments, the half-life is measured in a mammal. In some embodiments, the mammal is a non-human primate. In some embodiments, the mammal is a human. In some embodiments, the half-life is measured in a human to whom the composition has been previously administered. In some embodiments, the half-life is measured following intravenous administration. In some embodiments, the half-life is measured following subcutaneous administration.

In some embodiments, an albumin binding protein of the disclosure is formulated into a composition comprising one or more additional components (e.g., as a fusion protein), examples of which are provided and described herein.

Fusion Proteins

Provided herein are fusion proteins comprising an albumin binding protein of the disclosure ("D1") and at least one additional component ("D2"). In some embodiments, D1 and D2 are linked by a linker (L).

In some embodiments, the fusion proteins comprising albumin binding proteins provided herein are characterized by an extended half-life (e.g., serum half-life) as compared to a comparator, such as a therapeutic molecule that is not linked to an albumin binding protein as provided herein and/or, e.g., a reference albumin binding protein (e.g., as in TABLE 5 and/or SEQ ID NO: 33 or 45).

Fusions of the disclosure may be generated in different arrangements. For example, in some embodiments, a fusion protein can have, in N-to-C terminal direction, an arrangement (Orientation I), comprising D1-L-D2, wherein D1 comprises or consists of an albumin binding protein of the disclosure (comprising or consisting of a VHH); L is a linker; and D2 comprises or consists of at least one additional component.

In certain embodiments, a fusion protein can have, in N-to-C terminal direction, an arrangement (Orientation II), comprising D2-L-D1, wherein D1 comprises or consists of an albumin binding protein of the disclosure (comprising or consisting of a VHH); L is a linker; and D2 comprises or consists of at least one additional component.

In certain embodiments, the at least one additional component (D2) can comprise or consist of a second antigen binding protein or domain and/or a non-antigen binding moiety. In some embodiments, the second antigen binding protein or domain can be a therapeutic molecule. A therapeutic molecule may be an antigen binding molecule or a non-antigen binding moiety, and can be intended for use to achieve a particular effect (e.g., to treat) when contacting a cell and/or when administered to a subject in need thereof.

In some embodiments, the second antigen binding protein may comprise or consist of a single chain antibody or binding fragment thereof (e.g., scFv (e.g., a bispecific scFv), e.g., a single heavy chain, a single light chain, a variable heavy-chain domain (e.g., a VHH), a variable light-chain domain, a variable NAR domain, a single chain polypeptide), an F(ab'), an F(ab')2 (e.g., a bi-specific F(ab')2), an F(Ab')3 (e.g., a tri-specific F(Ab')3), an Fv, a DARPin, an Fc domain (e.g., an entire Fc, a modified Fc domain, an Fc domain with one or more substitutions relative to wild-type, an Fc fragment, etc.), a minibody, a diabody, a dAb fragment, an antibody (e.g., a monoclonal antibody), a multi-specific binding protein (e.g., bispecific antibody), and combinations thereof. In some embodiments, the second antigen binding protein (D2) may be a variable heavy chain domain comprising or consisting of a VHH domain. In some such embodiments, the VHH domain may be the same or different as the albumin binding protein of D1. In some embodiments, D2 may comprise or consist of a non-antigen binding moiety selected from a detectable tag such as a His tag, a Flag tag, a fluorescent tag, an Fc domain (e.g., an Fc fragment, etc.). In some embodiments, a D2 comprising or consisting of an Fc fragment does not bind an Fc antigen (e.g., an Fc receptor, etc.). In some embodiments, the Fc fragment may only have a small set of components (e.g., not all CH regions, partial CH regions, etc.) as compared to a wild-type Fc and/or may have one or more substitutions as compared to a wild-type Fc or fragment thereof.

In certain embodiments, an albumin binding protein fusion may further comprise one, two, three, four or more additional antigen binding proteins or non-antigen binding moieties (e.g., $D1-L-D_n$ or $D_n-D1-L-$), wherein n is selected from 1, 2, 3, 4, or more and wherein each $D_n$ domain may be the same or different from another $D_n$ domain in the same fusion.

In some embodiments, a fusion protein of the disclosure binds to albumin with a binding affinity stronger than about 10 µM, about 7.5 µM, about 5 µM, about 2.5 µM, about 1 µM, about 0.75 µM, about 0.5 µM, about 0.25 µM, about 0.1 µM, about 75 nM, about 50 nM, about 25 nM, about 10 nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, about 0.01 nM, or about 0.001 nM.

In some embodiments, the binding affinity of the fusion protein is stronger than about 0.1 μM, about 75 nM, about 50 nM, about 25 nM, about 10 nM, about 9 nM, about 8 nM, about 7 nM, about 6 nM, about 5 nM, about 4 nM, about 3 nM, about 2 nM, about 1 nM, about 0.75 nM, about 0.5 nM, about 0.25 nM, about 0.1 nM, or about 0.01 nM.

In some embodiments, the fusion protein binds to albumin with a KD of less than or equal to about $1 \times 10^{-6}$ M, $1 \times 10^{-7}$ M, $1 \times 10^{-8}$ M, $1 \times 10^{-9}$ M, or less at pH 6.0 or pH 7.4 as measured by surface plasmon resonance (SPR).

In some embodiments, the fusion protein binds (e.g., to albumin) with a stronger affinity when arranged in a configuration comprising D1-L-D2 as compared to D2-L-D1 when measured by SPR. In some embodiments, the fusion protein binds (e.g., to albumin) with a stronger affinity when arranged in a configuration comprising D2-L-D1 as compared to D1-L-D2 when measured by SPR.

In some embodiments, the binding affinity of the fusion protein for albumin is stronger at pH 6.0 than at pH 7.4. In some embodiments, the binding affinity is stronger at pH 7.4 than at pH 6.0. In some embodiments, the binding affinity is substantially unchanged at pH 6.0 as compared to pH 7.4.

In some embodiments, the albumin binding affinity of the fusion protein in orientation I is stronger than that of the fusion protein in orientation II at pH 6.0 and/or pH 7.4. In some embodiments, the albumin binding affinity of the fusion protein in orientation I is substantially unchanged as compared to that of the albumin binding protein in orientation II at pH 6.0 and/or pH 7.4. In some embodiments, the albumin binding affinity of the fusion protein in orientation II is stronger than that of the fusion protein in orientation I at pH 6.0 and/or pH 7.4.

In some embodiments, the fusion proteins are characterized by a half-life of at least about 3, 7, 14, 21, 28, 35, 42, 49, 56, 63, 70, 77, 84, 91, 98 or more days. In some embodiments, the half-life is in a range of about 3 days to about 98 days, about 7 days to about 91 days, about 14 days to about 84 days, about 21 days to about 77 days, about 28 days to about 70 days, about 35 days to about 63 days, about 42 days to about 56 days, about 3 days to about 42 days, about 7 days to about 49 days, about 14 days to about 56 days, about 5, 10, 15, 20, 25, 30, 35, 40, 45, 50, 55, 60, or more days, etc. In some embodiments, the half-life is in a range of about 14 days to about 56 days. In some embodiments, the half-life is at least about 84 days. In some embodiments, the half-life is at least about 56 days. In some embodiments, the half life is at least about 28 days. In some embodiments, the half-life is at least about 14 days. In some embodiments, the half-life is at least about 7 days. In some embodiments, the half-life of the fusion proteins comprising D1 and D2 is increased when D1 is linked to D2 as compared to the half-life of D2 alone (not linked to D1).

In some embodiments, the half-life of D2 in the fusion protein is increased at least about 1.05-fold, 1.1-fold, 1.15-fold, 1.2-fold, 1.25-fold, 1.3-fold, 1.35-fold, 1.4-fold, 1.45-fold. 1.50-fold, 1.55-fold, 1.6-fold, 1.65-fold, 1.7-fold, 1.75-fold, 1.8-fold, 1.85-fold, 1.9-fold, 1.95-fold, 2-fold, 2.5-fold, 3-fold, 3.5-fold, 4-fold, 4.5-fold, 5-fold, 6-fold, 7-fold, 8-fold, 9-fold, 10-fold, 15-fold, 20-fold, 25-fold, 30-fold, 40-fold, 50-fold, 75-fold, 100-fold, 200-fold, 250-fold. 300-fold, 350-fold, 400-fold, 450-fold, 500-fold, 550-fold, 600-fold, 650-fold, 700-fold, 750)-fold, 1.000-fold, 1.250-fold, 1.500-fold, 1.750-fold, 2.000-fold, 2.250-fold, 2.500-fold, 2.750)-fold, 3.000-fold, 3.250-fold, 3.500-fold, 3.750-fold, 4.000-fold, 4.250-fold, 4,500-fold, 4.750-fold, 5.000-fold or greater as compared to D2 alone (not in the fusion protein with D1).

Methods of measuring half-life include, but are not limited to, those well-known in the art. In some embodiments, the half-life is measured in a mammal. In some embodiments, the mammal is a non-human primate. In some embodiments, the mammal is a human. In some embodiments, the half-life is measured in a human to whom the composition has been previously administered. In some embodiments, the half-life is measured following intravenous administration. In some embodiments, the half-life is measured following subcutaneous administration.

In some embodiments, the fusion proteins comprising albumin binding proteins provided herein have a half-life that is at least 10% longer than a comparator (e.g., the at least one additional component (D2) not linked to an albumin binding protein, e.g., an antibody, e.g., an antibody fragment, e.g., a reference albumin binding protein and/or fusion thereof, etc.). In some embodiments, the comparator comprises the same complementarity determining regions and variable regions but different FR regions as the albumin binding protein (D1) in the fusion. In some embodiments, the comparator comprises the D2 alone (not fused to D1). In some embodiments, the half-life of the albumin binding proteins described herein is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% longer than the half-life of the comparator. In some embodiments, the half-life of the albumin binding proteins described herein is longer than the half-life of the comparator by at least about 1.05-fold, 1.1-fold, 1.15-fold, 1.2-fold, 1.25-fold. 1.3-fold, 1.35-fold, 1.4-fold, 1.45-fold, 1.50-fold, 1.55-fold, 1.6-fold, 1.65-fold, 1.7-fold, 1.75-fold, 1.8-fold, 1.85-fold, 1.9-fold, 1.95-fold, 2-fold, 2.5-fold, 3-fold, 3.5-fold, 4-fold, 4.5-fold, 5-fold, 6-fold, 7-fold, 8-fold, 9-fold, 10-fold, 15-fold, 20-fold, 25-fold, 30-fold, 40-fold, 50-fold. 75-fold, 100-fold, 200-fold, 250-fold, 300-fold, 350-fold, 400-fold, 450-fold, 500-fold, 550-fold. 600-fold, 650-fold, 700-fold, 750-fold, 1.000-fold, 1.250-fold, 1.500-fold, 1.750-fold, 2.000-fold, 2.250-fold, 2.500-fold, 2.750-fold, 3.000-fold, 3.250-fold, 3.500-fold, 3.750-fold, 4.000-fold, 4.250-fold, 4.500-fold, 4.750-fold, 5.000-fold or greater as compared to D2 alone (not linked to D1).

In some embodiments, the disclosure provides a polynucleotide encoding a fusion protein comprising an albumin binding protein provided herein, a linker, and at least one additional component. In some embodiments, a host cell comprises the polynucleotide encoding the fusion. In some embodiments, more than one host cell comprises, independently, separate components encoding the albumin binding protein (D1) and the at least one additional component (D2), which may be chemically conjugated to one another after each component is expressed. Polynucleotides encoding desired albumin binding proteins or fusions thereof can be incorporated (ligated) into expression vectors, which can be introduced into host cells through conventional transfection or transformation techniques. Exemplary host cells are *E. coli* cells. Chinese hamster ovary (CHO) cells, human embryonic kidney 293 (HEK 293) cells. HeLa cells, baby hamster kidney (BHK) cells, monkey kidney cells (COS), human hepatocellular carcinoma cells (e.g., Hep G2), and myeloma cells.

In certain embodiments, the disclosure provides a polynucleotide encoding a fusion protein comprising, from N-to-C terminus: (a) D1-L-D2; or (b) D2-L-D1, wherein, in each instance, D1 can comprise or consist of an albumin binding protein provided herein; L is a linker; and D2 can comprise or consist of at least one additional component. In some embodiments, the at least one additional component can comprise or consist of a therapeutic molecule or a detectable molecule. In some embodiments, the linker is selected from those provided herein (e.g., TABLE 8).

Exemplary fusion proteins demonstrating linking of at least one additional component to an albumin binding protein as provided herein are provided in Example 2. TABLES 9 and 10 and Example 5, TABLES 13, 14, and 15.

Linkers

Compositions provided herein can include one or more linkers. For example, in some embodiments, one or more components of a composition may be covalently bonded (e.g., conjugated, joined, attached, cross-linked) or otherwise associated (e.g., non-covalently bound) to one another by one or more linkers, thus, in each embodiment, "linking" the components. In some embodiments, an albumin binding protein, D1. (e.g., a VHH as provided herein) may be linked to one additional components, D2. (e.g., an antigen binding protein or non-antigen binding protein) via a linker.

In certain embodiments, a composition provided herein may comprise one or more linkers (L). For example, a composition comprising an albumin binding protein (D1) may be linked to at least one additional component (D2) (e.g., an antigen binding protein, a non-antigen binding moiety, etc.). In some embodiments, the linking is by a linker (L). In certain embodiments, the linker links the C-terminus of D1 to the N-terminus of D2 (D1-L-D2). In certain embodiments, the linker links the C-terminus of D2 to the N-terminus of D1 (D2-L-D1). As is understood to those of skill in the art, such compositions may be produced as genetic fusion proteins or as fusions that are conjugated together separately (e.g., after expression of each of D1 and D2).

In certain embodiments, linkers can be non-covalent. For example, a non-covalent linker can refer to the linking of two entities (e.g., D1 and/or D2 as provided herein, e.g., proteins, fragments thereof, non-antigen binding moieties, e.g., molecules, e.g., chemical moieties, etc.) by a non-covalent interaction or bond. By way of non-limiting example, non-covalent interactions or bonds can include hydrogen bonds, electrostatic bonds or interactions, halogen bonds, pi stacking, and van der Waals interactions.

In certain embodiments, linkers may be synthetic compound linkers such as, for example, chemical cross-linking agents. In some embodiments, a chemical cross-linking agent is selected from N-hydroxy succinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxy carbonyloxy)ethyl]sulfone (BSOCOES), and bis[2-(sulfosuccinimidooxy carbonyloxy)ethyl]sulfone (sulfo-BSOCOES). Given context, other appropriate chemical crosslinking agents will be known to those of skill in the art.

In certain embodiments, linkers may be peptide linkers (e.g., comprising amino acid residues and peptide bonds). In some embodiments, a peptide linker includes one or more peptide bonds. In some embodiments, a peptide linker includes one or more disulfide bonds. In some embodiments, a peptide linker results in one or more disulfide bonds (e.g., a peptide linker may comprise a cysteine residue which may pair with another cysteine residue outside of the linker that links to form a disulfide bond).

In some embodiments, the peptide linker comprises a flexible peptide linker. In some embodiments, the peptide linker comprises a rigid peptide linker. In some embodiments, the peptide linker comprises a cleavable peptide linker. In some embodiments, peptide linkers can be part of a fusion molecule or fusion protein, including, for example, the exemplary fusion proteins provided herein. Fusion (e.g., of two components) can refer to linking of two proteins (e.g., a protein, protein fragment, polypeptide) by a peptide bond or a peptide linker such that the two components (e.g., D1 and/or D2 as provided herein, proteins, fragments thereof, non-antigen binding moieties, etc.) are fused. For example, in some embodiments, an albumin binding protein as provided herein is fused to at least one additional component by a peptide linker, such as exemplary peptide linkers provided in TABLE 8.

In certain embodiments, two proteins can be directly and contiguously fused together by a peptide bond. In some embodiments, two proteins can be indirectly and non-contiguously fused through a peptide linker. In some embodiments, one protein is fused to a peptide linker by a peptide bond at a first position, and a second protein is fused to a peptide linker by a peptide bond at a second position. In some embodiments the linker (e.g., linker subunit, such as, for example GGGGS (SEQ ID NO: 58)) is repeated once. In some embodiments the linker is repeated more than once (e.g., GGGGSGGGGS (SEQ ID NO: 61)).

In some embodiments, a peptide linker can be a single amino acid residue or greater in length. In some embodiments, the peptide linker has at least one amino acid residue. In some embodiments, the linker has 2, 3, 4, 5, 6, 7, 8, 9, 10, 11, 12, 13, 14, 15, 16, 17, 18, 19, 20, 21, 22, 23, 24, 25, or more amino acid residues in length. In some embodiments, the linker has 2, 3, 4, 5, 6, 7, 8, 9, or 10 amino acids in length.

In some embodiments, the linker comprises at least 5 to about 50 amino acids. In some embodiments, the linker comprises about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about 5 to about 15 amino acids, about 5 to about 10 amino acids, about 10 to about 50 amino acids, about 15 to about 50 amino acids, about 20 to about 50 amino acids, about 25 to about 50 amino acids, about 30 to about 50 amino acids, about 35 to about 50 amino acids, about 40 to about 50 amino acids, or about 45 to about 50 amino acids.

In some embodiments, the linker comprises a sequence according to any set forth in TABLE 8.

In some embodiments, the linker comprises a sequence according to any one of SEQ ID NOs: 58-73.

In some embodiments, the linker comprises a sequence selected from the group consisting of $(GS)_n$ (SEQ ID NO: 232), $(G2S)_n$ (SEQ ID NO: 233), $(G3S)_n$ (SEQ ID NO: 234), $(G4S)_n$ (SEQ ID NO: 235), and $(G)_n$ (SEQ ID NO: 236), and wherein n is an integer from 2 to 20. In some embodiments, n is an integer from 2 to 18, from 2 to 16, from 2 to 14, from 2 to 12, from 2 to 10, from 2 to 8, from 2 to 6, from 2 to 4, from 4 to 20, from 6 to 20, from 8 to 20, from 10 to 20, from 12 to 20, from 14 to 20, from 16 to 20, or from 18 to 20.

In some embodiments, the linker comprises a sequence of GGGGG (SEQ ID NO: 68). In some embodiments, the linker comprises a sequence consisting of (GGGGG)n, and wherein n is an integer from 2 to 6 (SEQ ID NO: 237).

In some embodiments, the linker comprises a sequence selected from GGSGGD (SEQ ID NO: 69) or GGSGGE (SEQ ID NO: 70). In some embodiments, the linker comprises a sequence selected from the group consisting of (GGSGGD)n or (GGSGGE)$_n$, and wherein n is an integer from 2 to 6 (SEQ ID NO: 238-239).

In some embodiments, the linker comprises a sequence selected from the group consisting of GGGSGSGGGGS (SEQ ID NO: 71) and GGGGGPGGGGP (SEQ ID NO: 72). In some embodiments, the linker comprises a sequence selected from the group consisting of (GGGSGSGGGGS)$_n$ and (GGGGGPGGGGP)$_n$, and wherein n is an integer from 1 to 3 (SEQ ID NO: 240-241).

In some embodiments, the linker comprises a sequence selected from the group consisting of (GX)n, (GGX)n, (GGGX)n, (GGGGX)n, and (GzX)n, wherein z is between 1 and 20, and wherein n is at least 8. In some embodiments, z is between 2 and 18, 2 and 16, 2 and 14, 2 and 12, 2 and 10, 2 and 8, 2 and 6, 2 and 4, 4 and 20, 6 and 20, 8 and 20, 10 and 20, 12 and 20, 14 and 20, 16 and 20, or 18 and 20. In some embodiments, X is serine, aspartic acid, glutamic acid, threonine, alanine, or proline.

For example, in some embodiments, a linker may include a series of residues (e.g., alanine residues) alone or in addition to another linker (e.g., a G4S linker (SEQ ID NO: 58)). In some such embodiments, a linker comprises a sequence of GGGGSGGGSAAA (SEQ ID NO: 73).

In some embodiments, the linker is a G4S (SEQ ID NO: 58) linker. In some embodiments, the linker is a G4S multimer, with 2, 3, 4, 5, or more repeats of SEQ ID NO: 58. For example, in some embodiments, a linker comprises a peptide linker selected from GSGGGGS (SEQ ID NO: 60), GGGGSGGGGS ((G4S)$_2$; SEQ ID NO: 61), GGGGSGGGGSGGGGS ((G4S)$_3$; SEQ ID NO: 62), GGGGSGGGGSGGGGSGGGGS ((G4S)$_4$, SEQ ID NO: 63), GGGGSGGGGSGGGGSGGGGSGGGGS ((G4S)$_5$, SEQ ID NO: 64), and combinations thereof. In some embodiments, a linker comprises a peptide linker selected from GG, GGG, GGS, GGGS (SEQ ID NO: 67), GSGGS (SEQ ID NO: 59), GGGGSSA (SEQ ID NO: 65), GSGGGGSGGGGS (SEQ ID NO: 66) and combinations thereof.

TABLE 8

Exemplary Linker Sequences

| SEQ ID NO: | LINKER SEQUENCE |
|---|---|
| 58 | GGGGS |
| 59 | GSGGS |
| 60 | GSGGGGS |
| 61 | GGGGSGGGGS |
| 62 | GGGGSGGGGSGGGGS |
| 63 | GGGGSGGGGSGGGGSGGGGS |
| 64 | GGGGSGGGGSGGGGSGGGGSGGGGS |
| 65 | GGGGSSA |
| 66 | GSGGGGSGGGGS |
| 67 | GGGS |

TABLE 8-continued

Exemplary Linker Sequences

| SEQ ID NO: | LINKER SEQUENCE |
|---|---|
| 68 | GGGGG |
| 69 | GGSGGD |
| 70 | GGSGGE |
| 71 | GGGSGSGGGGS |
| 72 | GGGGGPGGGGP |
| 73 | GGGGSGGGSAAA |

PHARMACEUTICAL COMPOSITIONS

The present disclosure also features pharmaceutical compositions that contain a therapeutically effective amount of the albumin binding proteins or fusions thereof as provided herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249: 1527-1533, 1990).

A pharmaceutical composition in accordance with the disclosure may comprise an albumin binding protein as provided herein or fusion protein comprising two domains, D1 and D2, wherein D1 comprises or consists of an albumin binding protein of the disclosure and D2 comprises or consists of at least one additional component. In some embodiments, the at least one additional component comprises or consists of an antigen binding protein or a non-antigen binding moiety. In certain embodiments, D1 and D2 are linked by a linker (L) in an orientation (N-to-C terminus) of D1-L-D2 or D2-L-D1. In some embodiments, a fusion protein may further comprise additional components, in addition to D2, wherein each additional component may be the same or different from D2 and may be linked to one or more components through a linker (e.g., as provided herein, e.g., as in TABLE 8, etc.).

In some embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclo-dextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, *Remington's Pharmaceutical Sciences,* 18th ed. (Mack Publishing Company, 1990)).

In some embodiments, a pharmaceutical composition is citrate-free.

In some embodiments, a pharmaceutical composition may contain nanoparticles, e.g., polymeric nanoparticles, liposomes, or micelles.

In some embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxy butyric acid. Sustained release compositions may also include liposomes that can be prepared by any of several methods known in the art.

Pharmaceutical compositions containing an albumin binding protein or fusion thereof as provided herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In some embodiments, the albumin binding protein disclosed herein is administered intravenously or subcutaneously. In some embodiments, the albumin binding protein or fusion thereof is administered intravenously. In some embodiments, the albumin binding protein or fusion thereof is administered subcutaneously.

Useful formulations can be prepared by methods known in the pharmaceutical art. For example, see *Remington's Pharmaceutical Sciences,* 18th ed. (Mack Publishing Company. 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose. In some embodiments, the formulation for parenteral administration is citrate-free.

For intravenous or subcutaneous administration, suitable carriers include physiological saline, bacteriostatic water, Cremophor ELTM (BASF. Parsippany. NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

An intravenous or subcutaneous drug delivery formulation may be contained in a syringe, pen, or bag. In some embodiments, the bag is connected to a channel comprising a tube and/or a needle. In some embodiments, the formulation is a lyophilized formulation or a liquid formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration.

A polyol, which acts as a tonicifier and may stabilize the albumin binding protein, may also be included in the formulation. The polyol is added to the formulation in an amount which may vary with respect to the desired isotonicity of the formulation. In some embodiments, the aqueous formulation is isotonic. The amount of polyol added may also be altered with respect to the molecular weight of the polyol. For example, a lower amount of a monosaccharide (e.g., mannitol) is added, compared to a disaccharide (such as trehalose). In some embodiments, the polyol which is used in the formulation as a tonicity agent is mannitol.

A detergent or surfactant may also be added to the formulation. Exemplary detergents include nonionic detergents such as polysorbates (e.g., polysorbates 20, 80, etc.) or poloxamers (e.g., poloxamer 188). The amount of detergent added is such that it reduces aggregation of the formulated antibody and/or minimizes the formation of particulates in the formulation and/or reduces adsorption. In some embodiments, the formulation may include a surfactant which is a polysorbate. In some embodiments, the formulation may contain the detergent polysorbate 80 or Tween 80. Tween 80 is a term used to describe polyoxyethylene (20) sorbitan-monooleate (see Fiedler, Lexikon der Hifsstoffe, Editio Cantor Verlag Aulendorf, 4th edi., 1996).

In embodiments, the albumin binding protein or fusion thereof of the present disclosure is formulated as a liquid formulation. In some embodiments, the liquid formulation is prepared in combination with a sugar at stabilizing levels. In some embodiments, the liquid formulation is prepared in an aqueous carrier. In some embodiments, a stabilizer is added in an amount no greater than that which may result in a viscosity undesirable or unsuitable for intravenous administration. In some embodiments, the sugar is disaccharides, e.g., sucrose. In some embodiments, the liquid formulation may also include one or more of a buffering agent, a surfactant, and a preservative.

In some embodiments, the pH of the liquid formulation is set by addition of a pharmaceutically acceptable acid and/or base. In some embodiments, the pharmaceutically acceptable acid is hydrochloric acid. In some embodiments, the base is sodium hydroxide.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution. Ringer's solution or dextrose solution.

A preservative may be optionally added to the formulations herein to reduce bacterial action. The addition of a preservative may, for example, facilitate the production of a multi-use (multiple-dose) formulation.

The albumin binding protein or fusion thereof may be lyophilized to produce a lyophilized formulation including the proteins and a lyoprotectant. The lyoprotectant may be sugar, e.g., disaccharides. In some embodiments, the lyoprotectant is sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In some embodiments, the protein to sucrose or maltose weight ratio is of from 1:2 to 1:5. In some embodiments, the pH of the formulation, prior to lyophilization, is set by addition of a pharmaceutically acceptable acid and/or base. In some embodiments, the pharmaceutically acceptable acid is hydrochloric acid. In some embodiments, the pharmaceutically acceptable base is sodium hydroxide.

Methods of Preparation and Characterization

Described herein, in certain embodiments, are methods of making and characterizing albumin binding proteins and fusions thereof.

The albumin binding proteins described above can be made using recombinant DNA technology well known to a skilled person in the art. For example, one or more isolated polynucleotides encoding the albumin binding protein can be ligated to other appropriate nucleotide sequences, including, for example, constant region coding sequences, and expression control sequences, to produce conventional gene expression constructs (i.e., expression vectors) encoding the desired albumin binding proteins. Production of defined gene constructs is within routine skill in the art.

Polynucleotides encoding desired albumin binding proteins can be incorporated (ligated) into expression vectors, which can be introduced into host cells through conventional transfection or transformation techniques. Exemplary host cells are E. coli cells, Chinese hamster ovary (CHO) cells, human embryonic kidney 293 (HEK 293) cells, HeLa cells; baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode albumin binding proteins.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an albumin binding protein or portion thereof, the expression vector optionally contains sequences encoding all or part of a constant region, enabling an entire, or a part of, a heavy or light chain to be expressed. The gene construct can be introduced into eukaryotic host cells using conventional techniques.

In some embodiments, in order to express an albumin binding protein, an N-terminal signal sequence is included in the protein construct. Exemplary N-terminal signal sequences include signal sequences from interleukin-2, CD-5, IgG kappa light chain, trypsinogen, serum albumin, and prolactin.

After transfection, single clones can be isolated for cell bank generation using methods known in the art, such as limited dilution, ELISA, FACS, microscopy, or Clonepix. Clones can be cultured under conditions suitable for bioreactor scale-up and maintained expression of the albumin binding proteins.

The albumin binding proteins and fusions thereof can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

Albumin binding proteins and fusions thereof may be humanized as described and provided herein, in accordance with methods known to those of skill in the art. Methods of characterization, such as those used herein, are also known to those of skill in the art, including, but not limited to, for example, those used in Example 4, such as Affinity-capture self-interaction nanoparticle spectroscopy (AC-SINs), Protein thermal stability test by Static Light Scattering (SLS) and Differential Scanning Fluorimetry (DSF), and Polyreactive ELISA analyses.

Those of ordinary skill in the art will be familiar with methods of amino acid diversification and/or substitution (e.g., in CDRs, in FRs, etc.). Albumin binding proteins with diverse CDRs and/or FRs relative to those provided herein can be prepared and produced using methods provided herein and/or methods known to those of skill in the art to produce binding proteins that bind to an epitope of albumin.

In certain embodiments, the disclosure provides a method of generating a fusion protein comprising linking an albumin binding protein (D1) as provided herein (e.g., see TABLES 1-7) to at least one additional component (D2).

Methods of Use

Provided herein, in certain embodiments, are methods of using albumin binding proteins and fusions thereof.

In some aspects, the disclosure provides methods of using an albumin binding protein provided herein in a fusion protein. The method can comprise linking an albumin binding protein (D1) as provided herein (e.g., see TABLES 1-7) to at least one additional component (D2). In certain embodiments, when D2 is linked to D1 it shows one or more improvements on measures of half-life.

In some aspects, the disclosure provides methods of increasing half-life of a molecule (e.g., of a therapeutic molecule). In some embodiments, a method of increasing a half-life of a therapeutic molecule comprises administering a fusion protein an albumin binding protein (D1) as provided herein (see, e.g., TABLES 1-7) linked to at least one additional component comprising or consisting of a therapeutic molecule (D2), wherein a half-life of the therapeutic molecule is greater when administered as the fusion protein comprising D1 and D2 than when administered as D2 alone (not in a fusion protein with D1; not linked to D1). In some aspects, the disclosure provides a method of increasing a half-life of a therapeutic molecule in a subject in need thereof, the method comprising administering an effective amount of a fusion protein comprising an albumin binding protein (D1) as provided herein (see, e.g., TABLES 1-7) linked to at least one additional component comprising or consisting of a therapeutic molecule (D2), wherein a half-life of the therapeutic molecule is greater when administered as the fusion protein comprising D1 and D2 than when administered as D2 alone (not in a fusion protein with D1; not linked to D1). In certain embodiments, the effective amount is lower when the subject is administered the fusion protein as compared to D2 alone. In certain embodiments, the frequency of administration is reduced when the subject is administered the fusion protein as compared to D2 alone (not in a fusion protein with D1; not linked to D1).

In some embodiments, half-life extension of the therapeutic molecule (D2) in the fusion protein is increased at least about 1.05-fold, 1.1-fold, 1.15-fold, 1.2-fold, 1.25-fold, 1.3-fold. 1.35-fold, 1.4-fold, 1.45-fold, 1.50-fold, 1.55-fold, 1.6-fold, 1.65-fold, 1.7-fold, 1.75-fold, 1.8-fold, 1.85-fold, 1.9-fold, 1.95-fold, 2-fold, 2.5-fold, 3-fold, 3.5-fold, 4-fold, 4.5-fold, 5-fold, 6-fold, 7-fold, 8-fold, 9-fold, 10-fold, 15-fold, 20-fold, 25-fold, 30-fold, 40-fold, 50-fold, 75-fold. 100-fold, 200-fold, 250-fold, 300-fold, 350-fold, 400-fold, 450-fold, 500-fold, 550-fold, 600-fold, 650-fold, 700-fold, 750-fold, 1.000-fold, 1.250-fold, 1.500-fold, 1.750-fold, 2.000-fold. 2.250)-fold, 2.500-fold, 2.750)-fold, 3.000-fold, 3.250-fold, 3.500-fold, 3.750-fold, 4.000-fold. 4.250-fold, 4.500-fold, 4.750-fold, 5.000-fold or greater as to D2 alone (not in the fusion protein; not linked to D1).

In some aspects, the disclosure provides a method of treating a subject in need thereof, the method comprising administering an effective amount of a fusion protein comprising an albumin binding protein (D1) according to the disclosure (see, e.g., TABLES 1-7) linked to at least one additional component (D2) comprising or consisting of a therapeutic molecule, wherein a half-life of the therapeutic molecule is greater when administered as the fusion protein comprising D1 and D2 than when administered as D2 alone (not as a fusion comprising D1 linked to D2).

In some aspects, the disclosure provides a method of increasing a half-life of a therapeutic molecule, the method comprising linking an albumin binding protein (D1) provided herein (see, e.g., TABLES 1-7) to at least one additional component (D2) comprising or consisting of a therapeutic molecule, wherein the half-life of the therapeutic molecule after the linking is greater than before the linking.

In certain embodiments, administration of the fusion protein is subcutaneous. In certain embodiments, administration of the albumin binding protein is intravenous.

In one aspect, the disclosure provides a method of treating a disease or disorder in a patient in need thereof, the method comprising subcutaneously or intravenously administering to the patient an effective amount of a pharmaceutical composition comprising an albumin binding protein (D1) as provided herein (see, e.g., TABLES 1-7) and at least one additional component (D2). In some embodiments, the additional component comprises a therapeutic molecule. In some embodiments, the patient is treated in a manner that is improved when compared to administration of the therapeutic molecule alone (not in the fusion) as compared to administration with the fusion.

Described herein, in certain embodiments, are methods of treating a disease or disorder in a patient in need thereof. In some embodiments, the disease or disorder is an albumin-mediated disease or disorder in a patient in need of treatment, the method comprising subcutaneously or intravenously administering to the patient an effective amount of an albumin binding protein comprising sequences selected from any of TABLES 1-7, wherein the albumin binding protein may further have one or more components (D2) as described herein.

The albumin binding proteins may have one or more modifications (e.g., amino acid modifications) relative to a protein comprising the amino acid sequences of those disclosed in TABLES 1, 2 and 3 and/or one or more modifications to one or more amino acids in any heavy chain region (e.g., CDR, FR), such as provided herein. In some embodiments, the albumin binding protein comprises or consists of a sequence set forth in any of TABLES 1-7.

In some embodiments, one or more amino acids may be modified relative to those set forth in TABLES 1-7.

Further provided herein, in certain embodiments, are methods of treating a disease or disorder in a patient in need thereof, the method comprising subcutaneously or intravenously administering to the patient an effective amount of a fusion protein comprising an albumin binding protein of the disclosure, wherein the albumin binding protein specifically binds to an epitope of albumin.

In some embodiments, administration of the albumin binding protein or fusion thereof is intravenous, intratumoral, intramuscular, subcutaneous, intralesional, intraintestinal, intracolonic, intrarectal, intrapouch, or intraperitoneal. In some embodiments, administration of the albumin binding protein or fusion thereof is through a parenteral route such as intravenous, intramuscular, subcutaneous, intraarterial, or intraperitoneal administration. In some embodiments, administration of the albumin binding protein or fusion thereof is intravenous or subcutaneous. In some embodiments, administration of the albumin binding protein or fusion thereof is intravenous. In some embodiments, administration of the albumin binding protein or fusion thereof is subcutaneous.

The disclosure now being generally described, will be more readily understood by reference to the following examples, which are included merely for purposes of illustration of certain aspects and embodiments of the present disclosure, and is not intended to limit the disclosure.

EXAMPLES

Example 1: Synthesis, Expression, & Purification of Albumin Binding Proteins This Example describes gene synthesis and expression, as well as purification of llama-derived albumin binding proteins. To begin, llamas were immunized with human albumin to generate VHH single domain antibodies against albumin. Phage display screening was conducted using the immune repertoire of immunized llamas cloned into an immune phage library which was selected used human and cynomolgus serum albumin proteins. The amino acid sequences of the resulting VHHs were determined using standard sequencing approaches.

Gene Synthesis and Plasmid Construction

The coding sequences for albumin binding proteins were generated by DNA synthesis and PCR, subsequently subcloned into pcDNA3.1-based plasmid for protein expression in a mammalian cell system. The gene sequences in the expression vectors were confirmed by DNA sequencing.

Expression of Antibodies

Transient expression of antibodies was performed using the ExpiCHO™ Expression System (ThermoFisher, Cat. No. A29133). The ExpiCHO-S cells were expanded from a working cell bank and passaged in ExpiCHO expression media according to the manufacturer's instructions. The mixtures for transfection were prepared following the protocol instructions described in the ExpiCHO-S system manual. (Catalog Number A29133, Publication Number MAN0014337, Revision D.0). ExpiCHO cells were cultured for 14 days and the harvest was performed by filtration using 0.22 μm filtration units and DE as filter aid (Sartorius, Cat. No. SDLV-0150-05E0-2) after which they were processed immediately. The conditioned medium was harvested for protein purification.

Purification of Antibodies

Produced antibodies were captured from clarified supernatants using a HiTrap MabSelect PrismA 25 mL column (Cytiva, Cat. Nr. 17-5498-54) on an ÄKTA Pure 25 FPLC system. The column equilibration and protein binding were performed using 20 mM sodium phosphate with 150 mM NaCl pH 7.4 and for protein elution, it was used 100 mM sodium citrate with 150 mM NaCl pH 3.5. After elution, the peak corresponding to affinity purified antibodies was immediately neutralized with 30% of 1 M Tris pH 8.0. To polish the sample and to achieve a high purity >95% monomeric form, protein samples were loaded onto a HiLoad 26/600 Superdex 200 pg (Cytiva, Cat. Nr. 28-9893-36) on an ÄKTA Pure 25 FPLC system. The fractions corresponding to the monomeric antibody form were pooled from a 96 deep well plate into a 50 ml falcon tube and filtered through a 0.22 μm PES membrane (Fisher brand, Cat. Nr. 15206869, Lot Nr. 2103171806) in a laminar flow chamber. Protein samples were transferred to 50 kDa MWCO spin concentrators (Amicon 50K Cat. Nr. UFC905024; Lot Nr. 0000187574) for concentration and each round of centrifugation was 10 min at 4000×g, and it was repeated until the desired concentration was achieved.

SEC-HPLC Analysis

Analytical SEC-HPLC was performed on purified antibodies using Thermo Vanquish Flex UHPLC system (ThermoFisher) using a TSKgel Super SW mAb HTP (4.6 mm×15.0 cm) column (Tosoh Bioscience, Cat. Nr. 00228559). Approximately 10 μg of sample was loaded. The mobile phase was 200 mM sodium phosphate, 0.05% sodium azide, pH 6.7 with a flow rate of 0.35 ml/min for 10 min 25° C. The resulting selected VHH sequence is shown in TABLE 1.

Example 2: Generation of Exemplary Fusion Proteins

This Example describes generation of exemplary fusion proteins as proof-of-concept and developability of exemplary VHH albumin binding proteins. Fusions of llama-derived VHH albumin binding proteins were made with (1) wild-type IgG1 Fc (SEQ ID NO: 56); or (2) with a His tag (HHHHHHHH: SEQ ID NO: 74).

The N-terminus of the Fc of SEQ ID NO: 56 was linked to the C-terminus of the exemplary VHH albumin binding proteins via a G4S linker (SEQ ID NO: 58), according to an orientation, from N-to-C terminus of D1-L-D2, wherein D1 was an exemplary VHH albumin binding protein, L was an exemplary linker, and D2 was an exemplary second binding protein. The His tag of SEQ ID NO: 74 was linked to the C-terminus of the exemplary VHH albumin binding protein of SEQ ID NO: 1 and 75-101 by a GG linker. Exemplary VHH-L-Fc fusion proteins are set forth in TABLE 9. Exemplary VHH-His tag fusion proteins are set forth in TABLE 10.

TABLE 9

Exemplary VHH-Fc Fusion Proteins

| VHH Albumin Binding Protein Domain (D1) | SEQ ID NO: | Amino Acid Sequence of Fc Fusion (D1-L-D2) |
|---|---|---|
| VHH 1 | 5 | QVQLVESGGGLVQPGGSLRLSCAASGFTFGQFGMSWVRQAPAKGPER VSAISSDGSGTIYADSVKGRFTISRDNAKNTLYLQMNSLKPEDTAVY YCTIGSSTTPSGPGQGTQVTVSSGGGGSDKTHTCPPCPAPELLGGPS VFLFPPKPKDTLMISRTPEVTCVVVDVSHEDPEVKFNWYVDGVEVHN AKTKPREEQYNSTYRVVSVLTVLHQDWLNGKEYKCKVSNKALPAPIE KTISKAKGQPREPQVYTLPPSRDELTKNQVSLTCLVKGFYPSDIAVE WESNGQPENNYKTTPPVLDSDGSFFLYSKLTVDKSRWQQGNVFSCSV MHEALHNHYTQKSLSLSPG |
| VHH 2 | 143 | QVQLVESGGGLVQPGGSLRLSCAASGFTFGRFGMSWVRQAPGKGPEW VSAIDSGGADTRYAESVKGRFTISRDNAKKTLYLQMNSLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 3 | 144 | EVQLVESGGGLVQPGGSLRLSCAASGFTFGSFGMSWVRQAPGKGPEW VSAIDSGGADTRYAESVKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 4 | 145 | QVQLQESGGGLVQPGGSLRLSCAASGFTFGSFGMSWVRQAPGKGPEW VSAIDSGGADTRYAESVKGRETISRDNAKSTLYLQMNSLKPEDTAVY YCTIGRSSSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE |

TABLE 9-continued

Exemplary VHH-Fc Fusion Proteins

| VHH Albumin Binding Protein Domain (D1) | SEQ ID NO: | Amino Acid Sequence of Fc Fusion (D1-L-D2) |
|---|---|---|
| | | SNGQPENNYKTTPPVLDSDGSFFLYSKLTVDKSRWQQGNVFSCSVMH EALHNHYTQKSLSLSPG |
| VHH 5 | 146 | EVQLVESGGGLVQPGGSLRLSCAASGFTFGSFGMSWVRQAPGKGPEW VSAIDSGGTDTRYAESIKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 6 | 147 | QVQLVESGGGLVQPGGSLRLSCAASGFTFGSFGMSWVRQAPGKGPEW VSAIDSGGADTRYAESVKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 7 | 148 | EVQLVESGGGLVQSGGSLRLSCAASGFTFGSFGMSWVRQAPGKGPEW VSAIDGGGADTRYAESVKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 8 | 149 | EVQLVESGGGLVQPGGSLRLSCAASGFTFGSFGMSWVRQAPGKGPEW VSAIDSSGADTRYAESVKGRFTISRDNAKKTLYLQMNSLKPEDTAVY YCTIGRSTSRRNQGTQVTVASGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 9 | 150 | EVQLVESGGGLVQPGGSLRLSCAASGFTFGSFGMSWVRQAPGKGPEW VSAIDSGGADTRYAESVKGRFTISRDNAKKTLYLQMNSLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 10 | 151 | EVQLVESGGGLVQPGGSLRLSCAASGFTFGSFGMSWVRQAPGKGPEW VSAIDSGGADTRYAESVKGRFTISRDNAKKTLYLQMNSLKPEDTAVY YCTIGRSASRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 11 | 152 | QVQLVESGGGLVQPGGSLRLSCAASGFTFGSFGMSWVRQAPGKGPEW VSAIDSGGADTRYAETVKGRFTISRDNLKKTLYLQMNSLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 12 | 153 | QVQLVESGGGLVQPGGSLRLSCAASGFTFGSFGMSWVRQAPGKGPEW VSAIDSGGGDTRYSDSVKGRFAISRDNAKKTLYLQMNSLKPEDTAAY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |

TABLE 9-continued

Exemplary VHH-Fc Fusion Proteins

| VHH Albumin Binding Protein Domain (D1) | SEQ ID NO: | Amino Acid Sequence of Fc Fusion (D1-L-D2) |
|---|---|---|
| VHH 13 | 154 | EVQLVESGGGLVQAGGSLRLSCAASGFTFGSFGMSWVRQVPGKGPEW VSAIDSGGTDTRYAESIKGRFIISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 14 | 155 | QVQLVESGGGLVQPGGSLRLSCAASGFTFGSFGMSWVRQAPGKGPEW VSAIDSGGGDTRYAESVKGRFTISRDNAKKTLYLQMNSLKPEDTAVY YCTIGRSTSRVGQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 15 | 156 | QVQLQESGGGLVQPGGSLTLSCAASGFTFGSFGMSWVRQAPGKGPEW VSAIDSSGADTRYADSVKGRFTISRDNAKKTLYLQMNSLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 16 | 157 | EVQLVESGGGLVQPGGSLRLSCAASGFTFGSFGMSWVRQAPGKGPEW VSAIDSGGADTRYAESVKGRFTISRDNAKKTLYLQMNNLKPEDTAMY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 17 | 158 | QVQLQESGGGLVQPGDSLRLSCAASGFTFGSFGMSWVRQAPGREPEW VSAIDSGGADTRYAESVKGRFTISRDNAKKTLYLQMNTLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 18 | 159 | QVQLVESGGGLVQPGGSLRLSCAASGFTFGSFGMSWVRQAPGKGPEW VSAIDSGGTDTRYAESIKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 19 | 160 | QVQLVESGGGLVQPGGSLRLSCAASGFTFGSFGMSWVRQAPGKGPEW VSAIDSGGGVTLYAESVKGRFTISRDNAKKTLYLQMNSLKSEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 20 | 161 | QVQLVESGGGLVQPGGSLRLSCAASGFTFGSFGMSWVRQAPGKGPEW VSAIDGGGADTRYAESVKGRFTISRDNAKKTLYLQMNSLKPEDTAVY YCTIGGSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |

TABLE 9-continued

Exemplary VHH-Fc Fusion Proteins

| VHH Albumin Binding Protein Domain (D1) | SEQ ID NO: | Amino Acid Sequence of Fc Fusion (D1-L-D2) |
|---|---|---|
| VHH 21 | 162 | QVQLVESGGGLVQPGGSLRLSCAASGFSFGSFGMSWVRQAPGKGPEW VSAIDSGGADTRYAETVKGRFTISRDNAKKTLYLQMNSLKPEDTAVY YCTIGRSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 22 | 163 | QVQLVESGGGLVQAGGSLRLSCAASGFTFGSFGMSWVRQAPGKGPEW VSAIDSGGVDTRYAESVKGRFTISRDNAKKTLYLQMNSLKPEDTAVY YCTIGQSTSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 23 | 164 | QVQLQESGGGLVQPGGSLRLSCAASGFTFGSFGMSWVRQAPGKGPEW VSAIDSSGADTRYAESVKGRFTISRDNAKKTLYLQMNSLNPDDTAVY YCTIGQSISRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 24 | 165 | QVQLVESGGGLVQPGGSLRLSCAASGFTFGSFGMSWVRQAPGKGPEW VSAIDSSGADTIYAESVKGRETIARDNAKKTLYLQMNSLKPEDTAVY YCTIGQSISRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 25 | 166 | EVQLVESGGGLVQSGGSLRLSCAASGFTFGSFGMSWVRQAPGKGPEW VSAVDSGGADTRYAESVKGRETISRDNAKKTLYLQMNSLKPEDTAVY YCTIGQSTTRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 26 | 167 | EVQLVESGGGLVQPGGSLRLSCAASGFTFGSFGMGWSRQAPGKGPEW VAAINSGGDTTLYADSVKGRFTISRDNAKNTLYLEMNSLKPEDTAVY YCTIGRSSRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 27 | 168 | QVQLVESGGGLVQPGGSLRLSCAASGFTFGSFGMSWVRQAPGKGPEW VSAIDSGGADTRYTESVKGRFTISRDNAKKTLYLQMNSLKPEDTAVY YCTIGRSISRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |
| VHH 28 | 169 | QVQLVESGGGLVQPGGSLRLSCAASGFSFGSFGMSWVRQAPGKGPEW VSAIDSGGADTRYAETVKGRFTISRDNAKKTLYLQMNSLKPEDTAVY YCTIGRSTTRGSQGTQVTVSSGGGGSDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKT ISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPG |

TABLE 10

Exemplary VHH-His tag Fusion Proteins

| VHH Albumin Binding Protein Portion (D1) | SEQ ID NO: | Amino Acid Sequence of Fc Fusion (D1-L-D2) |
|---|---|---|
| VHH 1 | 6 | QVQLVESGGGLVQPGGSLRLSCAASGFTFGQFGMSWVRQAPAKGPE RVSAISSDGSGTIYADSVKGRFTISRDNAKNTLYLQMNSLKPEDTA VYYCTIGSSTTPSGPGQGTQVTVSSGGHHHHHHHH |
| VHH 2 | 170 | QVQLVESGGGLVQPGGSLRLSCAASGFTFGRFGMSWVRQAPGKGPE WVSAIDSGGADTRYAESVKGRFTISRDNAKKTLYLQMNSLKPEDTA VYYCTIGRSTSRGSQGTQVTVSSGGHHHHHHHH |
| VHH 3 | 171 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGQSTSRGSQGTQVTVSSGGHHHHHHHH |
| VHH 4 | 172 | QVQLQESGGGLVQPGGSLRLSCAASGFTFGSFGMSWVRQAPGKGPE WVSAIDSGGADTRYAESVKGRFTISRDNAKSTLYLQMNSLKPEDTA VYYCTIGRSSSRGSQGTQVTVSSGGHHHHHHHH |
| VHH 5 | 173 | EVQLVESGGGLVQPGGSLRLSCAASGFTFGSFGMSWVRQAPGKGPE WVSAIDSGGTDTRYAESIKGRFTISRDNAKKTLYLQMNSLKPEDTA VYYCTIGQSTSRGSQGTQVTVSSGGHHHHHHHH |
| VHH 6 | 174 | QVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGQSTSRGSQGTQVTVSSGGHHHHHHHH |
| VHH 7 | 175 | EVQLVESGGGLVQSGGSLRLSCAASGFTFGSFGMSWVRQAPGKGPE WVSAIDGGGADTRYAESVKGRFTISRDNAKKTLYLQMNSLKPEDTA VYYCTIGQSTSRGSQGTQVTVSSGGHHHHHHHH |
| VHH 8 | 176 | EVQLVESGGGLVQPGGSLRLSCAASGFTFGSFGMSWVRQAPGKGPE WVSAIDSSGADTRYAESVKGRFTISRDNAKKTLYLQMNSLKPEDTA VYYCTIGRSTSRRNQGTQVTVASGGHHHHHHHH |
| VHH 9 | 177 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGRSTSRGSQGTQVTVSSGGHHHHHHHH |
| VHH 10 | 178 | EVQLVESGGGLVQPGGSLRLSCAASGFTFGSFGMSWVRQAPGKGPE WVSAIDSGGADTRYAESVKGRFTISRDNAKKTLYLQMNSLKPEDTA VYYCTIGRSASRGSQGTQVTVSSGGHHHHHHHH |
| VHH 11 | 179 | QVQLVESGGGLVQPGGSLRLSCAASGFTFGSFGMSWVRQAPGKGPE WVSAIDSGGADTRYAETVKGRFTISRDNLKKTLYLQMNSLKPEDTA VYYCTIGRSTSRGSQGTQVTVSSGGHHHHHHHH |
| VHH 12 | 180 | QVQLVESGGGLVQPGGSLRLSCAASGFTFGSFGMSWVRQAPGKGPE WVSAIDSGGGDTRYSDSVKGREAISRDNAKKTLYLQMNSLKPEDTA AYYCTIGRSTSRGSQGTQVTVSSGGHHHHHHHH |
| VHH 13 | 181 | EVQLVESGGGLVQAGGSLRLSCAASGFTFGSFGMSWVRQVPGKGPE WVSAIDSGGTDTRYAESIKGRFIISRDNAKKTLYLQMNSLKPEDTA VYYCTIGQSTSRGSQGTQVTVSSGGHHHHHHHH |
| VHH 14 | 182 | QVQLVESGGGLVQPGGSLRLSCAASGFTFGSFGMSWVRQAPGKGPE WVSAIDSGGGDTRYAESVKGRFTISRDNAKKTLYLQMNSLKPEDTA VYYCTIGRSTSRVGQGTQVTVSSGGHHHHHHHH |
| VHH 15 | 183 | QVQLQESGGGLVQPGGSLTLSCAASGFTFGSFGMSWVRQAPGKGPE WVSAIDSSGADTRYADSVKGRFTISRDNAKKTLYLQMNSLKPEDTA VYYCTIGRSTSRGSQGTQVTVSSGGHHHHHHHH |
| VHH 16 | 184 | EVQLVESGGGLVQPGGSLRLSCAASGFTFGSFGMSWVRQAPGKGPE WVSAIDSGGADTRYAESVKGRFTISRDNAKKTLYLQMNNLKPEDTA MYYCTIGRSTSRGSQGTQVTVSSGGHHHHHHHH |
| VHH 17 | 185 | QVQLQESGGGLVQPGDSLRLSCAASGFTFGSFGMSWVRQAPGREPE WVSAIDSGGADTRYAESVKGRFTISRDNAKKTLYLQMNTLKPEDTA VYYCTIGRSTSRGSQGTQVTVSSGGHHHHHHHH |
| VHH 18 | 186 | QVQLVESGGGLVQPGGSLRLSCAASGFTFGSFGMSWVRQAPGKGPE WVSAIDSGGTDTRYAESIKGRFTISRDNAKKTLYLQMNSLKPEDTA VYYCTIGQSTSRGSQGTQVTVSSGGHHHHHHHH |

TABLE 10-continued

Exemplary VHH-His tag Fusion Proteins

| VHH Albumin Binding Protein Portion (D1) | SEQ ID NO: | Amino Acid Sequence of Fc Fusion (D1-L-D2) |
|---|---|---|
| VHH 19 | 187 | QVQLVESGGGLVQPGGSLRLSCAASGFTFGSFGMSWVRQAPGKGPE WVSAIDSGGGVTLYAESVKGRETISRDNAKKTLYLQMNSLKSEDTA VYYCTIGQSTSRGSQGTQVTVSSGGHHHHHHHH |
| VHH 20 | 188 | QVQLVESGGGLVQPGGSLRLSCAASGFTFGSFGMSWVRQAPGKGPE WVSAIDGGGADTRYAESVKGRFTISRDNAKKTLYLQMNSLKPEDTA VYYCTIGGSTSRGSQGTQVTVSSGGHHHHHHHH |
| VHH 21 | 189 | QVQLVESGGGLVQPGGSLRLSCAASGFSFGSFGMSWVRQAPGKGPE WVSAIDSGGADTRYAETVKGRFTISRDNAKKTLYLQMNSLKPEDTA VYYCTIGRSTSRGSQGTQVTVSSGGHHHHHHHH |
| VHH 22 | 190 | QVQLVESGGGLVQAGGSLRLSCAASGFTFGSFGMSWVRQAPGKGPE WVSAIDSGGVDTRYAESVKGRFTISRDNAKKTLYLQMNSLKPEDTA VYYCTIGQSTSRGSQGTQVTVSSGGHHHHHHHH |
| VHH 23 | 191 | QVQLQESGGGLVQPGGSLRLSCAASGFTFGSFGMSWVRQAPGKGPE WVSAIDSSGADTRYAESVKGRFTISRDNAKKTLYLQMNSLNPDDTA VYYCTIGQSISRGSQGTQVTVSSGGHHHHHHHH |
| VHH 24 | 192 | QVQLVESGGGLVQPGGSLRLSCAASGFTFGSFGMSWVRQAPGKGPE WVSAIDSSGADTIYAESVKGRFTIARDNAKKTLYLQMNSLKPEDTA VYYCTIGQSISRGSQGTQVTVSSGGHHHHHHHH |
| VHH 25 | 193 | EVQLVESGGGLVQSGGSLRLSCAASGFTFGSFGMSWVRQAPGKGPE WVSAVDSGGADTRYAESVKGRFTISRDNAKKTLYLQMNSLKPEDTA VYYCTIGQSTTRGSQGTQVTVSSGGHHHHHHHH |
| VHH 26 | 194 | EVQLVESGGGLVQPGGSLRLSCAASGFTFGSFGMGWSRQAPGKGPE WVAAINSGGDTTLYADSVKGRFTISRDNAKNTLYLEMNSLKPEDTA VYYCTIGRGSSRGSQGTQVTVSSGGHHHHHHHH |
| VHH 27 | 195 | QVQLVESGGGLVQPGGSLRLSCAASGFTFGSFGMSWVRQAPGKGPE WVSAIDSGGADTRYTESVKGRFTISRDNAKKTLYLQMNSLKPEDTA VYYCTIGRSISRGSQGTQVTVSSGGHHHHHHHH |
| VHH 28 | 196 | QVQLVESGGGLVQPGGSLRLSCAASGFSFGSFGMSWVRQAPGKGPE WVSAIDSGGADTRYAETVKGRFTISRDNAKKTLYLQMNSLKPEDTA VYYCTIGRSTTRGSQGTQVTVSSGGHHHHHHHH |

Example 3: Albumin Binding Protein VHH Fusion Binding Kinetics to Serum Albumin Using Surface Plasmon Resonance (SPR)

This Example describes binding kinetics of VHH sequences provided by Example 1 and set forth in TABLE 1, which were made into exemplary fusion proteins as set forth in TABLE 9 of Example 2. The albumin binding VHH-Fc fusions of SEQ ID NOs: 5 and 143-169 were evaluated for binding kinetics to human, cynomolgus, mouse, and rat serum albumin at pH 6.0 (human, cynomolgus, rat, and mouse) and pH 7.4 (human and cynomolgus). A control VHH albumin binding domain of SEQ ID NO: 17 (EVQLLESGGGLVQPGGSLRLS-CAASGFTFRSFGMSWVRQAPGKGPEWVSSIS-GSGSDTLYADSV KGRFTISRDNSKNT-LYLQMNSLRPEDTAVYYCTIGGSLSRSSQGTLVTVSS), comprising a CDR1 of SEQ ID NO: 18, a CDR2 of SEQ ID NO: 21, and SEQ ID NO: 22, was fused to the wt Fc IgG1 of SEQ ID NO: 56 (DKTHTCPPCPA-PELLGGPSVFLFPPKPKDTLMISRTPE-VTCVVVDVSHEDPEVKENWYVDGVEV HNAKTKPREEQYN-STYRVVSVLTVLHQDWLNGKEYKCKVSNKALPA-PIEKTISKAKGQPREPQV YTLPPSRDELTKNQVSLT-CLVKGFYPSDIAVEWESNGQPENNYKTT PPVLDSDGS FFLYSKLTV DKSRWQQGNVFSCSVMHEALHNHYTQKSLSLSPG), with the linker of SEQ ID NO: 58, for a VHH-Fc fusion control (SEQ ID NO: 33).

A Biacore 8K SPR system (GE HealthCare) equipped with CM5 Sensor Chip (Cytiva, Cat. Nr. 29149603) immobilized with an anti-human Fc specific antibody by amine coupling, was used to determine the binding kinetic rate and affinity constants of Fc-fused anti-albumin VHHs at 25° C., and in a running buffer of 1xHBS-EP+ pH 6.0 or pH 7.4 (10 mM HEPES, 150 mM NaCl, 3 mM EDTA, 0.05% Surfactant P20) (Cytiva, Cat. BR100669). Following a stabilization period in running buffer, the anti-albumin mAb constructs at 20 nM were captured onto flow cell 2 (active) for 60 sec at a flow rate of 30 μL/min.

Recombinant human, cynomolgus, mouse and rat serum albumin proteins were prepared at concentrations of 0, 31.25, 62.5, 125, 250, and 500 nM and injected over flow cell 1 (reference) and flow cell 2 (active) for 120 sec at a flow rate of 30 μL/min. Samples were injected in a multicycle manner over freshly captured mAb, by regenerating the capture surfaces with injection of 10 mM glycine pH 1.5 for 30 sec at a flow rate of 30 μL/min.

The data were processed and analyzed with Biacore Insight Evaluation Software Version 2.0.15.12933 (GE Healthcare) as follows. Responses from flow cell 1 (reference) were subtracted from the responses from flow cell 2 (active). The responses from the two buffer blank injections were then subtracted from the reference subtracted data (2-1) to yield double-referenced data, which were fit to a 1:1 binding model to determine the apparent association (ka)

and dissociation rate constants (kd). Their ratio provided the apparent equilibrium dissociation constant or affinity constant (KD=kd/ka). Kinetics are shown in TABLES 11A (human and cynomolgus serum albumin at pH 6.0 and pH 7.4) and 11B (mouse and rat serum albumin at pH 6.0).

TABLE 11A

| | Binding Kinetics Of Exemplary VHH-Fc Fusions (Human/Cynomolgus serum albumin) | | | | | | | |
| --- | --- | --- | --- | --- | --- | --- | --- | --- |
| | Human | | | | Cynomolgus | | | |
| | pH level | | | | | | | |
| | pH 6.0 | | | pH 7.4 | pH 6.0 | | | pH 7.4 |
| | Measurement | | | | | | | |
| SEQ ID NO: | ka (1/Ms) | kd (1/s) | KD (M) | KD (M) | ka (1/Ms) | kd (1/s) | KD (M) | KD (M) |
| 5 | 2.01E+05 | 4.81E−03 | 2.39E−08 | 4.47E−08 | 1.22E+05 | 4.47E−03 | 3.66E−08 | 4.41E−08 |
| 143 | 1.18E+05 | 2.22E−03 | 1.88E−08 | 5.16E−08 | 9.20E+04 | 4.00E−03 | 4.35E−08 | 9.15E−08 |
| 144 | 1.12E+05 | 1.17E−03 | 1.05E−08 | 2.81E−08 | 8.62E+04 | 2.11E−03 | 2.44E−08 | 5.30E−08 |
| 145 | 1.70E+05 | 3.34E−03 | 1.97E−08 | 5.63E−08 | 1.89E+05 | 9.77E−03 | 5.18E−08 | 1.07E−07 |
| 146 | 1.09E+05 | 8.73E−04 | 7.97E−09 | 2.34E−08 | 8.34E+04 | 1.62E−03 | 1.95E−08 | 4.04E−08 |
| 147 | 1.06E+05 | 1.25E−03 | 1.18E−08 | 3.07E−08 | 8.21E+04 | 2.19E−03 | 2.67E−08 | 5.39E−08 |
| 148 | 6.62E+04 | 1.18E−03 | 1.78E−08 | 2.39E−08 | 6.33E+04 | 2.13E−03 | 3.37E−08 | 4.51E−08 |
| 149 | 8.41E+04 | 2.14E−03 | 2.54E−08 | 4.25E−08 | 7.97E+04 | 3.93E−03 | 4.94E−08 | 8.11E−08 |
| 150 | 1.53E+05 | 2.89E−03 | 1.90E−08 | 5.01E−08 | 1.30E+05 | 6.11E−03 | 4.70E−08 | 9.24E−08 |
| 151 | 1.69E+05 | 3.51E−03 | 2.07E−08 | — | 1.80E+05 | 1.02E−02 | 5.64E−08 | |
| 152 | 1.48E+05 | 2.93E−03 | 1.98E−08 | 5.36E−08 | 1.39E+05 | 6.78E−03 | 4.88E−08 | 9.90E−08 |
| 153 | 1.52E+05 | 3.37E−03 | 2.21E−08 | 6.07E−08 | 1.64E+05 | 9.31E−03 | 5.68E−08 | 1.16E−07 |
| 154 | 1.08E+05 | 9.15E−04 | 8.46E−09 | 2.25E−08 | 8.25E+04 | 1.67E−03 | 2.02E−08 | 4.09E−08 |
| 155 | 1.39E+05 | 2.69E−03 | 1.93E−08 | 5.16E−08 | 1.18E+05 | 5.93E−03 | 5.03E−08 | 9.53E−08 |
| 156 | 7.44E+04 | 2.28E−03 | 3.06E−08 | 3.79E−08 | 7.46E+04 | 4.11E−03 | 5.51E−08 | 7.07E−08 |
| 157 | 1.55E+05 | 3.12E−03 | 2.02E−08 | 5.32E−08 | 1.38E+05 | 6.95E−03 | 5.05E−08 | 1.02E−07 |
| 158 | 1.96E+05 | 2.78E−03 | 1.42E−08 | 4.39E−08 | 1.46E+05 | 5.82E−03 | 3.98E−08 | 8.20E−08 |
| 159 | 1.17E+05 | 9.76E−04 | 8.36E−09 | 2.26E−08 | 8.82E+04 | 1.74E−03 | 1.97E−08 | 4.34E−08 |
| 160 | 1.03E+05 | 1.32E−03 | 1.28E−08 | 3.36E−08 | 7.93E+04 | 2.23E−03 | 2.81E−08 | 6.06E−08 |
| 161 | 1.49E+05 | 2.94E−03 | 1.98E−08 | 5.54E−08 | 1.04E+05 | 3.85E−03 | 3.68E−08 | 8.07E−08 |
| 162 | 1.44E+05 | 2.84E−03 | 1.97E−08 | 5.37E−08 | 1.40E+05 | 6.62E−03 | 4.74E−08 | 9.90E−08 |
| 163 | 6.18E+04 | 1.29E−03 | 2.09E−08 | 2.88E−08 | 5.92E+04 | 0.00214 | 3.63E−08 | 5.15E−08 |
| 33 | 1.27E+05 | 4.55E−04 | 3.58E−09 | 1.21E−08 | 8.77E+04 | 5.43E−04 | 6.19E−09 | 1.38E−08 |

TABLE 11B

| | Binding Kinetics Of Exemplary VHH-Fc Fusions (mouse/rat serum albumin at pH 6.0) | | | | | |
| --- | --- | --- | --- | --- | --- | --- |
| | Mouse | | | Rat | | |
| SEQ ID NO: | Measurement | | | | | |
| | ka (1/Ms) | kd (1/s) | KD (M) | ka (1/Ms) | kd (1/s) | KD (M) |
| 5 | 8.55E+04 | 1.50E−03 | 1.75E−08 | N/D | N/D | — |
| 143 | 1.31E+05 | 1.87E−02 | 1.43E−07 | 6.61E+04 | 9.08E−02 | 1.37E−06 |
| 144 | 1.01E+05 | 1.07E−03 | 1.06E−08 | N/D | N/D | — |
| 145 | 1.56E+05 | 2.62E−02 | 1.68E−07 | 4.11E+04 | 9.42E−02 | 2.29E−06 |
| 146 | 1.14E+05 | 7.99E−04 | 7.01E−09 | N/D | N/D | — |
| 147 | 1.07E+05 | 1.01E−03 | 9.44E−09 | N/D | N/D | — |
| 148 | 9.90E+04 | 4.48E−02 | 4.53E−07 | N/D | N/D | — |
| 149 | 1.39E+05 | 2.31E−02 | 1.66E−07 | 8.47E+04 | 1.32E−01 | 1.56E−06 |
| 150 | 1.58E+05 | 2.52E−02 | 1.59E−07 | 5.98E+04 | 9.41E−02 | 1.57E−06 |
| 151 | 1.50E+05 | 2.76E−02 | 1.84E−07 | 4.40E+04 | 1.56E−01 | 3.55E−06 |
| 152 | 1.48E+05 | 2.41E−02 | 1.63E−07 | 4.59E+04 | 9.13E−02 | 1.99E−06 |
| 153 | 1.53E+05 | 2.91E−02 | 1.90E−07 | 1.07E+04 | 1.35E−01 | 1.26E−05 |
| 154 | 1.22E+05 | 7.96E−04 | 6.52E−09 | N/D | N/D | |
| 155 | 1.09E+05 | 1.62E−02 | 1.49E−07 | 9.22E+04 | 1.11E−01 | 1.20E−06 |
| 156 | 8.78E+04 | 2.33E−02 | 2.65E−07 | N/D | N/D | — |
| 157 | 1.64E+05 | 2.76E−02 | 1.68E−07 | 4.82E+04 | 1.18E−01 | 2.45E−06 |
| 158 | 1.51E+05 | 2.42E−02 | 1.60E−07 | 6.23E+04 | 8.62E−02 | 1.38E−06 |
| 159 | 1.21E+05 | 9.05E−04 | 7.48E−09 | N/D | N/D | — |
| 160 | 1.35E+05 | 1.86E−02 | 1.38E−07 | N/D | N/D | — |

TABLE 11B-continued

Binding Kinetics Of Exemplary VHH-Fc Fusions
(mouse/rat serum albumin at pH 6.0)

| SEQ | Mouse | | | Rat | | |
| | | | Measurement | | | |
| ID NO: | ka (1/Ms) | kd (1/s) | KD (M) | ka (1/Ms) | kd (1/s) | KD (M) |
|---|---|---|---|---|---|---|
| 161 | 1.55E+05 | 3.09E−02 | 1.99E−07 | N/D | N/D | — |
| 162 | 1.51E+05 | 2.45E−02 | 1.62E−07 | 4.77E+04 | 8.02E−02 | 1.68E−06 |
| 163 | 9.25E+04 | 3.77E−02 | 4.08E−07 | N/D | N/D | — |
| 33 | 1.14E+05 | 6.31E−03 | 5.54E−08 | 2.03E+05 | 9.35E−02 | 4.61E−07 |

*N/D = not determined;
"—" no value due to very weak signals.

Example 4: VHH Fusion Characterization and Identification of Humanization Development Candidates This Example shows production and characterization of albumin binding VHH-Fc fusions of SEQ ID NOs: 5 and 143-169 and the albumin binding VHH-Fc fusion control (SEQ ID NO: 33). Protein yield (in mg/L) was measured, and characterization performed on AC-SINS, SLS and DSF, and Polyreactive ELISA assays as described herein.

AC-SINS (Affinity-Capture Self-Interaction Nanoparticle Spectroscopy)

Briefly, gold nanoparticles (15705; Ted Pella Inc.) were coated with 80% capturing anti-human goat IgG Fc (109-005-098; Jackson ImmunoResearch) and 20% with polyclonal goat nonspecific antibody (005-000-003; Jackson ImmunoResearch). The VHH fusions were then incubated with the particles for 2 h and the maximum wavelength shift was measured using Molecular Devices SpectraMax M2 with SoftMax Pro6 software. The wavelength shift ($\Delta\lambda_{max}$) of test samples away from the PBS sample were recorded for self-interacting assessment. Data are shown in TABLE 12.

Protein Thermal Stability Test by Static Light Scattering (SLS) and Differential Scanning Fluorimetry (DSF)

Albumin binding VHH fusion proteins in 20 mM sodium acetate pH 5.5 were loaded into a UNi (Unchained Labs). Samples were subjected to a thermal ramp from 20-95° C., with a ramp rate of 0.3° C./minute and ratio of the 330/350 nm fluorescence intensity and SLS at 266 nm against temperature were collected and UNCLE software was used to measure the peak of the 2nd derivatives of fluorescence ratio for the inflection points ($T_m$) of the transition curves, and SLS signal at 266 nm against temperature was used to determine Tagg. Data are shown in TABLE 12.

Polyreactive ELISA

In brief, dsDNA (1 μg/mL, D4522; Sigma) and insulin (5 μg/mL, 19278; Sigma) were coated onto ELISA plates (3369; Corning) individually at 50 μL per well overnight at 4° C. Plates were blocked with PBS with 0.5% BSA at room temperature (RT) for 1 h, followed by three washes with PBST (PBS plus 0.1% Tween 20). Fifty microliters of 100 nM testing VHH fusion solution was added to each well and incubated at RT for 1 h followed by six washes with 100 μL of PBS. Fifty microliters of diluted anti-human IgG-HRP conjugate (81-7120; ZyMax) was added to the wells and incubated for 1 h followed by six washes. Finally, 50 μL of TMB substrate (34021; Fisher Scientific) was added to each well and incubated for 10-15 min. The reactions were stopped by adding 50 μL of 2 M sulfuric acid to each well. The absorbance was read at 450 nm and DNA or insulin score determined by normalizing absorbance by control wells with no test antibody. Data are shown in TABLE 12.

Based on the results of these characterization experiments, the fusion proteins VHH-1 (SEQ ID NO: 1; VHH-Fc Fusion SEQ ID NO: 5), VHH-9 (SEQ ID NO: 83; VHH-Fc Fusion SEQ ID NO: 151), and VHH-20 (SEQ ID NO: 94; VHH-Fc Fusion SEQ ID NO: 162) were selected for humanization.

TABLE 12

Yield And Developability Characterization

| SEQ ID NO: | Yield (mg/L) | AC-SINS ($\Delta\lambda$max, nm) | SLS and DSF | | Polyreactive ELISA | |
| | | | T M1 ± 1 SD (° C.) | Tagg266 (° C.) | DNA Score | Insulin Score |
|---|---|---|---|---|---|---|
| 33 | — | 2 | 60.80 ± 0.11 | 68.10 ± 0.51 | 3 | 1 |
| 5 | 930.1 | 0 | 55.4 | 68.6 | 1 | 1 |
| 143 | 331.8 | 7 | 58.10 ± 0.32 | 75.50 ± 0.42 | 4 | 4 |
| 144 | 463.1 | −1 | 58.10 ± 0.12 | 68.90 ± 0.65 | 2 | 1 |
| 145 | 540 | 1 | 55.30 ± 0.15 | 69.20 ± 0.26 | 2 | 1 |
| 146 | 446 | 0 | 57.10 ± 0.15 | 68.70 ± 0.52 | 2 | 1 |
| 147 | 491.4 | 3 | 58.20 ± 0.06 | 71.30 ± 1.22 | 3 | 1 |
| 148 | 368.5 | −1 | 57.00 ± 0.55 | 69.60 ± 1.21 | 2 | 1 |
| 149 | 267.1 | 0 | 56.40 ± 0.17 | 75.00 ± 0.19 | 2 | 2 |
| 150 | 455.8 | −1 | 58.00 ± 0.24 | 72.10 ± 0.34 | 3 | 1 |
| 151 | 412.8 | 1 | 55.40 ± 0.15 | 73.50 ± 0.16 | 4 | 1 |
| 152 | 585.6 | 1 | 57.00 ± 0.31 | 73.50 ± 0.44 | 3 | 1 |
| 153 | 80 | −1 | 53.20 ± 0.31 | 75.00 ± 0.34 | 1 | 1 |
| 154 | 942.6 | 1 | 57.9 | 69.8 | 1 | 1 |
| 155 | 190.6 | 0 | 59.00 ± 0.29 | 74.80 ± 0.26 | 2 | 1 |
| 156 | 660.3 | 1 | 58.70 ± 0.20 | 73.00 ± 0.81 | 2 | 1 |

TABLE 12-continued

| | | AC-SINS | SLS and DSF | | Polyreactive ELISA | |
|---|---|---|---|---|---|---|
| | | | | | | |
| SEQ ID NO: | Yield (mg/L) | (Δλmax, nm) | T M1 ± 1 SD (° C.) | Tagg266 (° C.) | DNA Score | Insulin Score |
| 157 | 493.1 | 0 | 58.80 ± 0.17 | 74.30 ± 0.08 | 3 | 1 |
| 158 | 632.5 | 0 | 56 | 69.1 | 1 | 1 |
| 159 | 648.2 | 0 | 56.80 ± 0.10 | 70.50 ± 1.30 | 2 | 1 |
| 160 | 322.3 | 0 | 57.50 ± 0.21 | 69.80 ± 0.89 | 2 | 1 |
| 161 | 603.4 | 1 | 57.00 ± 0.16 | 72.00 ± 0.37 | 2 | 1 |
| 162 | 554.4 | −1 | 58.90 ± 0.12 | 74.70 ± 0.20 | 3 | 1 |
| 163 | 717.6 | 0 | 60.2 | 74.7 | 1 | 1 |

Example 5: Humanization and Fusions

This Example describes humanization of VHH binding domains selected in Example 4: VHH-1 (SEQ ID NO: 1; VHH-Fc Fusion SEQ ID NO: 5), VHH-9 (SEQ ID NO: 83; VHH-Fc Fusion SEQ ID NO: 151), and VHH-20 (SEQ ID NO: 94; VHH-Fc Fusion SEQ ID NO: 162).

Selected sequences were humanized by VH CDR grafting. AlphaFold2 was utilized to predict the VH model. Features taken into account for humanization include homology and developability. That is, homology (of human germline to parental sequence) is evaluated, and germline usage rate in existing humanized or human therapeutic monoclonal antibodies, and distribution of V region gene segments in the natural human antibody repertoire are considered. Here, IGHV3-23*04 was selected as the germline for VH CDR grafting for VHH-1, VHH-9, and VHH-20 humanization. Humanized variants were formatted into two fusion orientations, each comprising an Fc component (D2) and an albumin binding protein component (D1), linked by a linker, L: (a) Orientation I: D1-L-D2 (albumin binding protein-linker-Fc) and (b) Orientation II: D2-L-D1 (Fc-linker-albumin binding protein). The fusion proteins were tested via SPR kinetic screening to confirm their antigen binding strength. The linker in the Orientation I and Orientation II fusions was a G4S linker of SEQ ID NO: 58.

Resulting VHH sequences are set forth in TABLE 4, with CDRs set forth in TABLE 5B and TABLE 7. As in Example 3, Fc fusions and his-tag fusions were generated with the humanized VHH proteins.

The Fc fusions were as follows: the VHH domains were fused to a wild-type IgG1 Fc of SEQ ID NO: 56 in one of two orientations: (a) Orientation I: C-terminus of the albumin binding VHH domain of any of SEQ ID NOs: 7-16 and 130-140 linked to the N-terminus of the Fc domain of SEQ ID NO: 56 through a linker of SEQ ID NO: 58 or (b) Orientation II: C-terminus of Fc domain of SEQ ID NO: 56 linked to the N-terminus of the albumin binding VHH domain of any of SEQ ID NOs: 7-16 and 130-140 through a linker of SEQ ID NO: 58. A control VHH albumin binding domain (SEQ ID NO: 17) that binds to human, cynomolgus, and mouse albumin was used to create control fusion proteins: (1) a control VHH-Fc fusion of SEQ ID NO: 33, and (2) a control Fc-VHH fusion of Orientation II (SEQ ID NO: 45, DKTHTCPPCPA-PELLGGPSVFLFPPKPKDTLMISRTPE-VTCVVVDVSHEDPEVKENWYVDGVEV HNAKTKPREEQYN-STYRVVSVLTVLHQDWLNGKEYKCKVSNKALPA-PIEKTISKAKGQPREPQV YTLPPSRDELTKNQVSLT-CLVKGFYPSDIAVEWESNGQPENNYKTTPPVLDSDGS FFLYSKLTV DKSRWQQGNVFSCSVMHEALHN-HYTQKSLSLSPGGGGGSEVQLLESGG-GLVQPGGSLRLSCAAS GFTFRSFGMSWVRQAPGKG-PEWVSSISGSGSDTLYADSVKGRFTISRDNSKNTLYLQ MNSLRPE DTAVYYCTIGGSLSRSSQGTLVTVSS) that were also used in subsequent characterization experiments.

His-tag fusions were made by fusing a his-tag (HHHHHHHH, SEQ ID NO: 74) to the albumin binding VHH domains of each of SEQ ID NOs: 7-16 and 130-140).

The llama (non-humanized) sequences of VHH-1 (SEQ ID NO: 1), VHH-9 (SEQ ID NO: 83), and VHH-20 (SEQ ID NO: 94) was also used to generate an Fc fusion of Orientation II (see TABLE 14, SEQ ID NOs: 34, 208, and 217). The fusion proteins are set forth in TABLE 13 (VHH-Fc fusions), TABLE 14 (Fc-VHH fusions), and TABLE 15 (VHH-His tag fusions).

TABLE 13

| Humanized VHH Albumin Binding Protein Domain (D1) | SEQ ID NO: | Amino Acid Sequence of Fc Fusion (D1-L-D2) |
|---|---|---|
| VHH 1-1 | 23 | EVQLLESGGGLVQPGGSLRLSCAASGFTFGQFGMSWVRQAPGKGPERVSAI SSDGSGTIYADSVKGRFTISRDNSKNTLYLQMNSLRPEDTAVYYCTIGSST TPSGPGQGTLVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-2 | 24 | EVQLLESGGGLVQPGGSLRLSCAASGFTFSQFGMSWVRQAPGKGPERVSAI SSDGSGTIYADSVKGRFTISRDNSKNTLYLQMNSLRPEDTAVYYCTIGSST TPSGPGQGTLVTVSSGGGGSDKTHTCPPCPAPELLGGPSVFLFPPKPKDTL |

TABLE 13-continued

Exemplary Humanized VHH-Fc Fusion Proteins

| Humanized VHH Albumin Binding Protein Domain (D1) | SEQ ID NO: | Amino Acid Sequence of Fc Fusion (D1-L-D2) |
|---|---|---|
| | | MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-3 | 25 | QVQLVESGGGLVQPGGSLRLSCAASGFTFGQFGMSWVRQAPAKGPERVSAI SSSGSGTIYADSVKGRFTISRDNAKNTLYLQMNSLKPEDTAVYYCTIGSST TPSGPGQGTQVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-4 | 26 | QVQLVESGGGLVQPGGSLRLSCAASGFTFGQFGMSWVRQAPAKGPERVSAI SSGGSGTIYADSVKGRFTISRDNAKNTLYLQMNSLKPEDTAVYYCTIGSST TPSGPGQGTQVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-5 | 27 | QVQLVESGGGLVQPGGSLRLSCAASGFTFGQFGMSWVRQAPAKGPERVSAI SSDASGTIYADSVKGRETISRDNAKNTLYLQMNSLKPEDTAVYYCTIGSST TPSGPGQGTQVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-6 | 28 | QVQLVESGGGLVQPGGSLRLSCAASGFTFGQFGMSWVRQAPAKGPERVSAI SSDSSGTIYADSVKGRETISRDNAKNTLYLQMNSLKPEDTAVYYCTIGSST TPSGPGQGTQVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-7 | 29 | EVQLVESGGGLVQPGGSLRLSCAASGFTFGQFGMSWVRQAPGKGLEWVSAI SSDGSGTIYADSVKGRFTISRDNSKNTLYLQMNSLRAEDTAVYYCTIGSST TPSGWGQGTTVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-8 | 30 | EVQLVESGGGLVQPGGSLRLSCAASGFTFGQFGMSWVRQAPGKGLEWVSAI SSDGSGTIYADSVKGRFTISRDNSKNTLYLQMNSLRAEDTAVYYCTIGSST TPSGPGQGTTVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-9 | 31 | EVQLVESGGGLVQPGGSLRLSCAASGFTFGQFGMSWFRQAPGKEREFVSAI SSDGSGTIYADSVKGRFTISRDNSKNTLYLQMNSLRAEDTAVYYCTIGSST TPSGWGQGTTVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 1-10 | 32 | EVQLVESGGGLVQPGGSLRLSCAASGFTFGQFGMSWFRQAPGKEREFVSAI SSDGSGTIYADSVKGRFTISRDNSKNTLYLQMNSLRAEDTAVYYCTIGSST TPSGPGQGTTVTVSSGGGGSDKTHTCPPCPAPELLGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSF FLYSKLTVDKSRWQQGNVFSCSVMHEALHNHYTQKSLSLSPG |
| VHH 9-1 | 197 | EVQLLESGGGLVQPGGSLRLSCAASGFTFGSFGMSWVRQAPGKGPEWVSAI DSGGADTRYAESVKGRFTISRDNSKNTLYLQMNSLRPEDTAVYYCTIGRSA SRGSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS |

TABLE 13-continued

Exemplary Humanized VHH-Fc Fusion Proteins

| Humanized VHH Albumin Binding Protein Domain (D1) | SEQ ID NO: | Amino Acid Sequence of Fc Fusion (D1-L-D2) |
|---|---|---|
| | | VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-2 | 198 | EVQLLESGGGLVQPGGSLRLSCAASGFTFSSFGMSWVRQAPGKGPEWVSAI DSGGADTRYAESVKGRFTISRDNSKNTLYLQMNSLRPEDTAVYYCTIGRSA SRGSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-3 | 199 | EVQLLESGGGLVQPGGSLRLSCAASGFTFGSFGMSWVRQAPGKGPEWVSAI DSGGADTRYAESVKGRFTISRDNSKNTLYLQMNSLRPEDTAVYYCTIGRSA SRSSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-4 | 200 | EVQLVESGGGLVQPGGSLRLSCAASGFTFGSFGMSWVRQAPGKGLEWVSAI DSGGADTRYAESVKGRFTISRDNSKNTLYLQMNSLRAEDTAVYYCTIGRSA SRWGQGTTVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-5 | 201 | EVQLVESGGGLVQPGGSLRLSCAASGFTFGSFGMSWVRQAPGKGLEWVSAI DSGGADTRYAESVKGRFTISRDNSKNTLYLQMNSLRAEDTAVYYCTIGRSA SRGGQGTTVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-6 | 202 | EVQLVESGGGLVQPGGSLRLSCAASGFTFGSFGMSWFRQAPGKEREFVSAI DSGGADTRYAESVKGRFTISRDNSKNTLYLQMNSLRAEDTAVYYCTIGRSA SRWGQGTTVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 9-7 | 203 | EVQLVESGGGLVQPGGSLRLSCAASGFTFGSFGMSWFRQAPGKEREFVSAI DSGGADTRYAESVKGRFTISRDNSKNTLYLQMNSLRAEDTAVYYCTIGRSA SRGGQGTTVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 20-1 | 204 | EVQLLESGGGLVQPGGSLRLSCAASGFSFGSFGMSWVRQAPGKGPEWVSAI DSGGADTRYAETVKGRFTISRDNSKNTLYLQMNSLRPEDTAVYYCTIGRST SRGSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG |
| VHH 20-2 | 205 | EVQLLESGGGLVQPGGSLRLSCAASGFTFGSFGMSWVRQAPGKGPEWVSAI DSGGADTRYAETVKGRFTISRDNSKNTLYLQMNSLRPEDTAVYYCTIGRST SRGSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVESCSVMHEALHNHYTQKSLSLSPG |
| VHH 20-3 | 206 | EVQLLESGGGLVQPGGSLRLSCAASGFTFSSFGMSWVRQAPGKGPEWVSAI DSGGADTRYAETVKGRFTISRDNSKNTLYLQMNSLRPEDTAVYYCTIGRST SRGSQGTLVTVSSGGGGSDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR |

TABLE 13-continued

| Exemplary Humanized VHH-Fc Fusion Proteins | | |
| --- | --- | --- |
| Humanized<br>VHH Albumin<br>Binding Protein<br>Domain (D1) | SEQ<br>ID NO: | Amino Acid Sequence of Fc Fusion (D1-L-D2) |
| | | DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG |
| VHH 20-4 | 207 | EVQLLESGGGLVQPGGSLRLSCAASGFSFGSFGMSWVRQAPGKGPEWVSAI<br>DSGGADTRYAETVKGRFTISRDNSKNTLYLQMNSLRPEDTAVYYCTIGRST<br>SRSSQGTLVTVSSGGGGSDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG |
| VHH-Fc control | 33 | EVQLLESGGGLVQPGGSLRLSCAASGFTFRSFGMSWVRQAPGKGPEWVSSI<br>SGSGSDTLYADSVKGRFTISRDNSKNTLYLQMNSLRPEDTAVYYCTIGGSL<br>SRSSQGTLVTVSSGGGGSDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG |

TABLE 14

| Exemplary Humanized VHH-Fc Fusion Proteins | | |
| --- | --- | --- |
| Humanized VHH<br>Albumin Binding<br>Protein Domain (D1) | SEQ<br>ID NO: | Amino Acid Sequence of Fc Fusion (D2-L-D1) |
| VHH 1 | 34 | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKN<br>QVSLTCLVKGFYPSDIAVEWESNGQPENNYKTTPPVLDSDGSFFLYS<br>KLTVDKSRWQQGNVFSCSVMHEALHNHYTQKSLSLSPGGGGGSQVQL<br>VESGGGLVQPGGSLRLSCAASGFTFGQFGMSWVRQAPAKGPERVSAI<br>SSDGSGTIYADSVKGRFTISRDNAKNTLYLQMNSLKPEDTAVYYCTI<br>GSSTTPSGPGQGTQVTVSS |
| VHH 1-1 | 35 | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKN<br>QVSLTCLVKGFYPSDIAVEWESNGQPENNYKTTPPVLDSDGSFFLYS<br>KLTVDKSRWQQGNVFSCSVMHEALHNHYTQKSLSLSPGGGGGSEVQL<br>LESGGGLVQPGGSLRLSCAASGFTFGQFGMSWVRQAPGKGPERVSAI<br>SSDGSGTIYADSVKGRFTISRDNSKNTLYLQMNSLRPEDTAVYYCTI<br>GSSTTPSGPGQGTLVTVSS |
| VHH 1-2 | 36 | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKN<br>QVSLTCLVKGFYPSDIAVEWESNGQPENNYKTTPPVLDSDGSFFLYS<br>KLTVDKSRWQQGNVFSCSVMHEALHNHYTQKSLSLSPGGGGGSEVQL<br>LESGGGLVQPGGSLRLSCAASGFTFSQFGMSWVRQAPGKGPERVSAI<br>SSDGSGTIYADSVKGRFTISRDNSKNTLYLQMNSLRPEDTAVYYCTI<br>GSSTTPSGPGQGTLVTVSS |
| VHH 1-3 | 37 | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKN<br>QVSLTCLVKGFYPSDIAVEWESNGQPENNYKTTPPVLDSDGSFFLYS<br>KLTVDKSRWQQGNVFSCSVMHEALHNHYTQKSLSLSPGGGGGSQVQL<br>VESGGGLVQPGGSLRLSCAASGFTFGQFGMSWVRQAPAKGPERVSAI<br>SSSGSGTIYADSVKGRFTISRDNAKNTLYLQMNSLKPEDTAVYYCTI<br>GSSTTPSGPGQGTQVTVSS |
| VHH 1-4 | 38 | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKN<br>QVSLTCLVKGFYPSDIAVEWESNGQPENNYKTTPPVLDSDGSFFLYS |

TABLE 14-continued

Exemplary Humanized VHH-Fc Fusion Proteins

| Humanized VHH Albumin Binding Protein Domain (D1) | SEQ ID NO: | Amino Acid Sequence of Fc Fusion (D2-L-D1) |
| --- | --- | --- |
| | | KLTVDKSRWQQGNVFSCSVMHEALHNHYTQKSLSLSPGGGGGSQVQL VESGGGLVQPGGSLRLSCAASGFTFGQFGMSWVRQAPAKGPERVSAI SSGGSGTIYADSVKGRFTISRDNAKNTLYLQMNSLKPEDTAVYYCTI GSSTTPSGPGQGTQVTVSS |
| VHH 1-5 | 39 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSQVQL VESGGGLVQPGGSLRLSCAASGFTFGQFGMSWVRQAPAKGPERVSAI SSDASGTIYADSVKGRFTISRDNAKNTLYLQMNSLKPEDTAVYYCTI GSSTTPSGPGQGTQVTVSS |
| VHH 1-6 | 40 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSQVQL VESGGGLVQPGGSLRLSCAASGFTFGQFGMSWVRQAPAKGPERVSAI SSDSSGTIYADSVKGRFTISRDNAKNTLYLQMNSLKPEDTAVYYCTI GSSTTPSGPGQGTQVTVSS |
| VHH 1-7 | 41 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGQFGMSWVRQAPGKGLEWVSAI SSDGSGTIYADSVKGRFTISRDNSKNTLYLQMNSLRAEDTAVYYCTI GSSTTPSGWGQGTTVTVSS |
| VHH 1-8 | 42 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGQFGMSWVRQAPGKGLEWVSAI SSDGSGTIYADSVKGRFTISRDNSKNTLYLQMNSLRAEDTAVYYCTI GSSTTPSGPGQGTTVTVSS |
| VHH 1-9 | 43 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGQFGMSWFRQAPGKEREFVSAI SSDGSGTIYADSVKGRFTISRDNSKNTLYLQMNSLRAEDTAVYYCTI GSSTTPSGWGQGTTVTVSS |
| VHH 1-10 | 44 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGQFGMSWFRQAPGKEREFVSAI SSDGSGTIYADSVKGRFTISRDNSKNTLYLQMNSLRAEDTAVYYCTI GSSTTPSGPGQGTTVTVSS |
| VHH 9 | 208 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGSFGMSWVRQAPGKGPEWVSAI DSGGADTRYAESVKGRFTISRDNAKKTLYLQMNSLKPEDTAVYYCTI GRSASRGSQGTQVTVSS |
| VHH 9-1 | 209 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFGSFGMSWVRQAPGKGPEWVSAI |

TABLE 14-continued

Exemplary Humanized VHH-Fc Fusion Proteins

| Humanized VHH Albumin Binding Protein Domain (D1) | SEQ ID NO: | Amino Acid Sequence of Fc Fusion (D2-L-D1) |
|---|---|---|
| | | DSGGADTRYAESVKGRFTISRDNSKNTLYLQMNSLRPEDTAVYYCTI GRSASRGSQGTLVTVSS |
| VHH 9-2 | 210 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFSSFGMSWVRQAPGKGPEWVSAI DSGGADTRYAESVKGRFTISRDNSKNTLYLQMNSLRPEDTAVYYCTI GRSASRGSQGTLVTVSS |
| VHH 9-3 | 211 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFGSFGMSWVRQAPGKGPEWVSAI DSGGADTRYAESVKGRFTISRDNSKNTLYLQMNSLRPEDTAVYYCTI GRSASRSSQGTLVTVSS |
| VHH 9-4 | 212 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGSFGMSWVRQAPGKGLEWVSAI DSGGADTRYAESVKGRFTISRDNSKNTLYLQMNSLRAEDTAVYYCTI GRSASRWGQGTTVTVSS |
| VHH 9-5 | 213 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGSFGMSWVRQAPGKGLEWVSAI DSGGADTRYAESVKGRFTISRDNSKNTLYLQMNSLRAEDTAVYYCTI GRSASRGGQGTTVTVSS |
| VHH 9-6 | 214 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGSFGMSWFRQAPGKEREFVSAI DSGGADTRYAESVKGRFTISRDNSKNTLYLQMNSLRAEDTAVYYCTI GRSASRWGQGTTVTVSS |
| VHH 9-7 | 215 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL VESGGGLVQPGGSLRLSCAASGFTFGSFGMSWFRQAPGKEREFVSAI DSGGADTRYAESVKGRFTISRDNSKNTLYLQMNSLRAEDTAVYYCTI GRSASRGGQGTTVTVSS |
| VHH 20 | 216 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSQVQL VESGGGLVQPGGSLRLSCAASGFSFGSFGMSWVRQAPGKGPEWVSAI DSGGADTRYAETVKGRFTISRDNAKKTLYLQMNSLKPEDTAVYYCTI GRSTSRGSQGTQVTVSS |
| VHH 20-1 | 217 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFSFGSFGMSWVRQAPGKGPEWVSAI DSGGADTRYAETVKGRFTISRDNSKNTLYLQMNSLRPEDTAVYYCTI GRSTSRGSQGTLVTVSS |

TABLE 14-continued

Exemplary Humanized VHH-Fc Fusion Proteins

| Humanized VHH Albumin Binding Protein Domain (D1) | SEQ ID NO: | Amino Acid Sequence of Fc Fusion (D2-L-D1) |
|---|---|---|
| VHH 20-2 | 218 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFGSFGMSWVRQAPGKGPEWVSAI DSGGADTRYAETVKGRFTISRDNSKNTLYLQMNSLRPEDTAVYYCTI GRSTSRGSQGTLVTVSS |
| VHH 20-3 | 219 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFSSFGMSWVRQAPGKGPEWVSAI DSGGADTRYAETVKGRFTISRDNSKNTLYLQMNSLRPEDTAVYYCTI GRSTSRGSQGTLVTVSS |
| VHH 20-4 | 220 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFSFGSFGMSWVRQAPGKGPEWVSAI DSGGADTRYAETVKGRFTISRDNSKNTLYLQMNSLRPEDTAVYYCTI GRSTSRSSQGTLVTVSS |
| Fc-VHH Control | 45 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGGGGGSEVQL LESGGGLVQPGGSLRLSCAASGFTFRSFGMSWVRQAPGKGPEWVSSI SGSGSDTLYADSVKGRFTISRDNSKNTLYLQMNSLRPEDTAVYYCTI GGSLSRSSQGTLVTVSS |

TABLE 15

Exemplary Humanized VHH-His tag Fusion Proteins

| Humanized VHH Albumin Binding Protein Domain (D1) | SEQ ID NO: | Amino Acid Sequence of His Tag Fusion (D1-GG-His) |
|---|---|---|
| VHH 1-1 | 46 | EVQLLESGGGLVQPGGSLRLSCAASGFTFGQFGMSWVRQAPGKG PERVSAISSDGSGTIYADSVKGRFTISRDNSKNTLYLQMNSLRP EDTAVYYCTIGSSTTPSGPGQGTLVTVSSGGHHHHHHHH |
| VHH 1-2 | 47 | EVQLLESGGGLVQPGGSLRLSCAASGFTFSQFGMSWVRQAPGKG PERVSAISSDGSGTIYADSVKGRFTISRDNSKNTLYLQMNSLRP EDTAVYYCTIGSSTTPSGPGQGTLVTVSSGGHHHHHHHH |
| VHH 1-3 | 48 | QVQLVESGGGLVQPGGSLRLSCAASGFTFGQFGMSWVRQAPAKG PERVSAISSSGSGTIYADSVKGRFTISRDNAKNTLYLQMNSLKP EDTAVYYCTIGSSTTPSGPGQGTQVTVSSGGHHHHHHHH |
| VHH 1-4 | 49 | QVQLVESGGGLVQPGGSLRLSCAASGFTFGQFGMSWVRQAPAKG PERVSAISSGGSGTIYADSVKGRFTISRDNAKNTLYLQMNSLKP EDTAVYYCTIGSSTTPSGPGQGTQVTVSSGGHHHHHHHH |
| VHH 1-5 | 50 | QVQLVESGGGLVQPGGSLRLSCAASGFTFGQFGMSWVRQAPAKG PERVSAISSDASGTIYADSVKGRFTISRDNAKNTLYLQMNSLKP EDTAVYYCTIGSSTTPSGPGQGTQVTVSSGGHHHHHHHH |
| VHH 1-6 | 51 | QVQLVESGGGLVQPGGSLRLSCAASGFTFGQFGMSWVRQAPAKG PERVSAISSDSSGTIYADSVKGRFTISRDNAKNTLYLQMNSLKP EDTAVYYCTIGSSTTPSGPGQGTQVTVSSGGHHHHHHHH |

TABLE 15-continued

Exemplary Humanized VHH-His tag Fusion Proteins

| Humanized VHH Albumin Binding Protein Domain (D1) | SEQ ID NO: | Amino Acid Sequence of His Tag Fusion (D1-GG-His) |
|---|---|---|
| VHH 1-7 | 52 | EVQLVESGGGLVQPGGSLRLSCAASGFTFGQFGMSWVRQAPGKG LEWVSAISSDGSGTIYADSVKGRFTISRDNSKNTLYLQMNSLRA EDTAVYYCTIGSSTTPSGWGQGTTVTVSSGGHHHHHHHH |
| VHH 1-8 | 53 | EVQLVESGGGLVQPGGSLRLSCAASGFTFGQFGMSWVRQAPGKG LEWVSAISSDGSGTIYADSVKGRFTISRDNSKNTLYLQMNSLRA EDTAVYYCTIGSSTTPSGPGQGTTVTVSSGGHHHHHHHH |
| VHH 1-9 | 54 | EVQLVESGGGLVQPGGSLRLSCAASGFTFGQFGMSWERQAPGKE REFVSAISSDGSGTIYADSVKGRFTISRDNSKNTLYLQMNSLRA EDTAVYYCTIGSSTTPSGWGQGTTVTVSSGGHHHHHHHH |
| VHH 1-10 | 55 | EVQLVESGGGLVQPGGSLRLSCAASGFTFGQFGMSWERQAPGKE REFVSAISSDGSGTIYADSVKGRFTISRDNSKNTLYLQMNSLRA EDTAVYYCTIGSSTTPSGPGQGTTVTVSSGGHHHHHHHH |
| VHH 9-1 | 221 | EVQLLESGGGLVQPGGSLRLSCAASGFTFGSFGMSWVRQAPGKG PEWVSAIDSGGADTRYAESVKGRFTISRDNSKNTLYLQMNSLRP EDTAVYYCTIGRSASRGSQGTLVTVSSGGHHHHHHHH |
| VHH 9-2 | 222 | EVQLLESGGGLVQPGGSLRLSCAASGFTFSSFGMSWVRQAPGKG PEWVSAIDSGGADTRYAESVKGRFTISRDNSKNTLYLQMNSLRP EDTAVYYCTIGRSASRGSQGTLVTVSSGGHHHHHHHH |
| VHH 9-3 | 223 | EVQLLESGGGLVQPGGSLRLSCAASGFTFGSFGMSWVRQAPGKG PEWVSAIDSGGADTRYAESVKGRFTISRDNSKNTLYLQMNSLRP EDTAVYYCTIGRSASRSSQGTLVTVSSGGHHHHHHHH |
| VHH 9-4 | 224 | EVQLVESGGGLVQPGGSLRLSCAASGFTFGSFGMSWVRQAPGKG LEWVSAIDSGGADTRYAESVKGRFTISRDNSKNTLYLQMNSLRA EDTAVYYCTIGRSASRWGQGTTVTVSSGGHHHHHHHH |
| VHH 9-5 | 225 | EVQLVESGGGLVQPGGSLRLSCAASGFTFGSFGMSWVRQAPGKG LEWVSAIDSGGADTRYAESVKGRFTISRDNSKNTLYLQMNSLRA EDTAVYYCTIGRSASRGGQGTTVTVSSGGHHHHHHHH |
| VHH 9-6 | 226 | EVQLVESGGGLVQPGGSLRLSCAASGFTFGSFGMSWFRQAPGKE REFVSAIDSGGADTRYAESVKGRFTISRDNSKNTLYLQMNSLRA EDTAVYYCTIGRSASRWGQGTTVTVSSGGHHHHHHHH |
| VHH 9-7 | 227 | EVQLVESGGGLVQPGGSLRLSCAASGFTFGSFGMSWFRQAPGKE REFVSAIDSGGADTRYAESVKGRFTISRDNSKNTLYLQMNSLRA EDTAVYYCTIGRSASRGGQGTTVTVSSGGHHHHHHHH |
| VHH 20-1 | 228 | EVQLLESGGGLVQPGGSLRLSCAASGFSFGSFGMSWVRQAPGKG PEWVSAIDSGGADTRYAETVKGRFTISRDNSKNTLYLQMNSLRP EDTAVYYCTIGRSTSRGSQGTLVTVSSGGHHHHHHHH |
| VHH 20-2 | 229 | EVQLLESGGGLVQPGGSLRLSCAASGFTFGSFGMSWVRQAPGKG PEWVSAIDSGGADTRYAETVKGRFTISRDNSKNTLYLQMNSLRP EDTAVYYCTIGRSTSRGSQGTLVTVSSGGHHHHHHHH |
| VHH 20-3 | 230 | EVQLLESGGGLVQPGGSLRLSCAASGFTFSSFGMSWVRQAPGKG PEWVSAIDSGGADTRYAETVKGRFTISRDNSKNTLYLQMNSLRP EDTAVYYCTIGRSTSRGSQGTLVTVSSGGHHHHHHHH |
| VHH 20-4 | 231 | EVQLLESGGGLVQPGGSLRLSCAASGFSFGSFGMSWVRQAPGKG PEWVSAIDSGGADTRYAETVKGRFTISRDNSKNTLYLQMNSLRP EDTAVYYCTIGRSTSRSSQGTLVTVSSGGHHHHHHHH |

Example 6: Humanized Albumin Binding Protein VHH Fusion Binding Kinetics to Serum Albumin Using Surface Plasmon Resonance (Spr)

This Example describes binding kinetics of VHH sequences provided by Example 5 and set forth in TABLES 4-7, which were made into exemplary fusion proteins as set forth in TABLE 13 and TABLE 14 of Example 5, were evaluated for binding kinetics. Albumin binding VHH-Fc of SEQ ID NOs: 5, 23, 25-32, 143-169, and 197-207 and Fc-VHH fusions of SEQ ID NOs: 34, 35, 37-44, and 208-220 were evaluated for binding kinetics to human serum albumin at pH 6.0 and pH 7.4. The control VHH-Fc of SEQ ID NO: 33 and the control Fc-VHH of SEQ ID NO: 45 were also measured.

Similar to Example 3, a Biacore 8K SPR system (GE HealthCare) equipped with CM5 Sensor Chip (Cytiva, Cat. Nr. 29149603) immobilized with an anti-human Fc specific antibody by amine coupling, was used to determine the binding kinetic rate and affinity constants of Fc-fused anti-albumin VHHs at 25 C and in a running buffer of 1xHBS-EP+pH 6.0 or pH 7.4 (10 mM HEPES, 150 mM NaCl, 3 mM EDTA, 0.05% Surfactant P20) (Cytiva, Cat. BR100669). Following a stabilization period in running buffer, the anti-albumin mAb constructs at 20 nM were captured onto flow cell 2 (active) for 60 sec at a flow rate of 30 µL/min.

Recombinant human serum albumin proteins were prepared at concentrations of 0, 31.25, 62.5, 125, 250, and 500 nM and injected over flow cell 1 (reference) and flow cell 2 (active) for 120 sec at a flow rate of 30 µL/min. Samples were injected in a multi-cycle manner over freshly captured mAb, by regenerating the capture surfaces with injection of 10 mM glycine pH 1.5 for 30 sec at a flow rate of 30 µL/min.

The data were processed and analyzed with Biacore Insight Evaluation Software Version 2.0.15.12933 (GE Healthcare) as follows. Responses from flow cell 1 (reference) were subtracted from the responses from flow cell 2 (active). The responses from the two buffer blank injections were then subtracted from the reference subtracted data (2-1) to yield double-referenced data, which were fit to a 1:1 binding model to determine the apparent association (ka) and dissociation rate constants (kd). Their ratio provided the apparent equilibrium dissociation constant or affinity constant (KD=kd/ka). Kinetics are shown in TABLES 16A (VHH-Fc pH 6.0 and pH 7.4) and 16B (Fc-VHH at pH 6.0 and pH 7.4).

TABLE 16A

Binding Kinetics Of Exemplary Humanized VHH-Fc
Fusions (Human serum albumin)

| SEQ ID | Human pH level | | | | | |
| | pH 6.0 | | | pH 7.4 | | |
| | Measurement | | | | | |
| NO: | ka (1/Ms) | kd (1/s) | KD (M) | ka (1/Ms) | kd (1/s) | KD (M) |
|---|---|---|---|---|---|---|
| 5 | 1.11E+06 | 1.22E−02 | 1.10E−08 | 8.03E+05 | 8.61E−03 | 1.07E−08 |
| 25 | 4.68E+05 | 1.76E−02 | 3.75E−08 | 6.07E+05 | 4.62E−03 | 7.61E−09 |
| 26 | 3.57E+05 | 1.30E−02 | 3.64E−08 | N/A | N/A | N/A |
| 27 | 5.03E+05 | 1.15E−02 | 2.28E−08 | 6.56E+05 | 4.07E−03 | 6.21E−09 |
| 28 | 7.15E+05 | 7.14E−03 | 9.99E−09 | 6.66E+05 | 4.21E−03 | 6.32E−09 |
| 29 | 8.48E+04 | 3.68E−03 | 4.34E−08 | N/A | N/A | N/A |
| 30 | 2.06E+05 | 1.37E−02 | 6.67E−08 | 1.46E+05 | 1.64E−03 | 1.13E−08 |
| 31 | N/A | N/A | N/A | N/A | N/A | N/A |
| 32 | 4.16E+05 | 1.00E−02 | 2.40E−08 | N/D | N/D | N/D |
| 23 | N/D | N/D | N/D | N/D | N/D | N/D |
| 200 | 9.65E+04 | 3.30E−03 | 3.42E−08 | N/A | N/A | N/A |
| 201 | 2.30E+05 | 6.38E−03 | 2.77E−08 | 1.56E+05 | 1.58E−04 | 1.01E−09 |
| 202 | 1.99E+05 | 5.25E−03 | 2.63E−08 | N/A | N/A | N/A |
| 203 | 4.39E+05 | 3.93E−03 | 8.94E−09 | N/A | N/A | N/A |
| 197 | N/D | N/D | N/D | N/D | N/D | N/D |
| 204 | N/D | N/D | N/D | N/D | N/D | N/D |

*N/A - no binding;
N/D = not determined.

TABLE 16B

Binding Kinetics Of Exemplary Humanized Fc-VHH Fusions
(Human serum albumin)

| SEQ ID | Human pH level | | | | | |
| | pH 6.0 | | | pH 7.4 | | |
| | Measurement | | | | | |
| NO: | ka (1/Ms) | kd (1/s) | KD (M) | ka (1/Ms) | kd (1/s) | KD (M) |
|---|---|---|---|---|---|---|
| 34 | 2.95E+05 | 1.94E−02 | 6.57E−08 | 2.61E+05 | 9.61E−03 | 3.68E−08 |
| 37 | N/A | N/A | N/A | N/A | N/A | N/A |
| 38 | N/A | N/A | N/A | N/A | N/A | N/A |
| 39 | 1.57E+05 | 1.67E−02 | 1.06E−07 | 8.58E+04 | 7.78E−03 | 9.07E−08 |
| 40 | 7.22E+04 | 5.98E−03 | 8.27E−08 | 5.63E+04 | 4.03E−03 | 7.16E−08 |
| 41 | N/A | N/A | N/A | N/A | N/A | N/A |
| 42 | 6.62E+04 | 9.43E−03 | 1.42E−07 | N/A | N/A | N/A |
| 43 | N/A | N/A | N/A | N/A | N/A | N/A |
| 44 | 1.77E+05 | 8.04E−03 | 4.53E−08 | N/A | N/A | N/A |
| 35 | 7.05E+04 | 1.43E−02 | 2.03E−07 | 1.43E+05 | 2.13E−02 | 1.49E−07 |
| 208 | 1.61E+05 | 1.33E−02 | 8.25E−08 | 2.80E+05 | 1.36E−03 | 4.88E−09 |
| 212 | N/A | N/A | N/A | N/A | N/A | N/A |
| 213 | N/A | N/A | N/A | N/A | N/A | N/A |

TABLE 16B-continued

Binding Kinetics Of Exemplary Humanized Fc-VHH Fusions
(Human serum albumin)

| SEQ ID | Human pH level | | | | | |
|---|---|---|---|---|---|---|
| | pH 6.0 | | | pH 7.4 | | |
| | | | Measurement | | | |
| NO: | ka (1/Ms) | kd (1/s) | KD (M) | ka (1/Ms) | kd (1/s) | KD (M) |
| 214 | N/A | N/A | N/A | N/A | N/A | N/A |
| 215 | N/A | N/A | N/A | N/A | N/A | N/A |
| 209 | 2.33E+06 | 3.88E−01 | 1.67E−07 | 4.14E+04 | 1.32E−02 | 3.18E−07 |
| 217 | 1.43E+05 | 2.61E−02 | 1.82E−07 | 1.98E+05 | 6.06E−02 | 3.06E−07 |

*N/A - no binding;
N/D = not determined.

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

What is claimed is:

1. A humanized albumin binding protein comprising: a VHH domain, the VHH domain comprising three complementarity determining regions (CDRs), CDR1, CDR2, and CDR3 therein, each having an amino acid sequence, wherein:
   (a) the amino acid sequence of CDR1 comprises SEQ ID NO: 104;
   (b) the amino acid sequence of CDR2 comprises SEQ ID NO: 109; and
   (c) the amino acid sequence of CDR3 comprises SEQ ID NO: 119.

2. The humanized albumin binding protein of claim 1, wherein the VHH domain has an amino acid sequence comprising an amino acid sequence selected from the group consisting of SEQ ID NOs: 137-140.

3. The humanized albumin binding protein of claim 1, further comprising an antigen represented by D2, wherein D2 is a binding protein or a non-antigen binding moiety, wherein D2 is linked to the humanized albumin binding protein of claim 1 according to a formula, from N-to-C terminus represented by: (a) D1-L-D2, or (b) D2-L-D1, wherein L is a peptide linker and D1 is the humanized albumin binding protein of claim 1.

4. The humanized albumin binding protein of claim 3, wherein the peptide linker has an amino acid sequence comprising an amino acid sequence selected from the group consisting of SEQ ID NOs: 58-73.

5. The humanized albumin binding protein of claim 3, wherein D2 is selected from the group consisting of a single chain antibody or binding fragment thereof, an scFv, a bispecific scFv, a single heavy chain, a single light chain, a variable heavy-chain domain, a VHH, a variable light-chain domain, a variable NAR domain, a single chain polypeptide, a F(ab'), a F(ab')2, a bi-specific F(ab')2, a F(Ab')3, a tri-specific F(Ab') 3, an Fv, a designed ankyrin repeat protein, an Fc domain, an entire Fc, a modified Fc domain, an Fc domain with one or more substitutions relative to wild-type, an Fc fragment, a minibody, a diabody, a dAb fragment, an antibody, a monoclonal antibody, a multispecific binding protein, and a bispecific antibody.

6. A humanized albumin binding protein comprising a VHH domain, wherein the VHH domain has an amino acid sequence comprising an amino acid sequence selected from the group consisting of SEQ ID NOs: 137-140.

7. The humanized albumin binding protein of claim 6, further comprising an antigen represented by D2, wherein D2 is a binding protein or a non-antigen binding moiety, wherein D2 is linked to the humanized albumin binding protein of claim 6 according to a formula, from N-to-C terminus represented by: (a) D1-L-D2, or (b) D2-L-D1, wherein L is a peptide linker and D1 is the humanized albumin binding protein of claim 6.

8. The humanized albumin binding protein of claim 7, wherein the peptide linker has an amino acid sequence comprising an amino acid sequence selected from the group consisting of SEQ ID NOs: 58-73.

9. The humanized albumin binding protein of claim 7, wherein D2 is selected from the group consisting of a single chain antibody or binding fragment thereof, an scFv, a bispecific scFv, a single heavy chain, a single light chain, a variable heavy-chain domain, a VHH, a variable light-chain domain, a variable NAR domain, a single chain polypeptide, a F(ab'), a F(ab')2, a bi-specific F(ab')2, a F(Ab')3, a tri-specific F(Ab')3, an Fv, a designed ankyrin repeat protein, an Fc domain, an entire Fc, a modified Fc domain, an Fc domain with one or more substitutions relative to wild-type, an Fc fragment, a minibody, a diabody, a dAb fragment, an antibody, a monoclonal antibody, a multispecific binding protein, and a bispecific antibody.

160

* * * * *